US011124567B2

(12) United States Patent
Dennis et al.

(10) Patent No.: US 11,124,567 B2
(45) Date of Patent: Sep. 21, 2021

(54) ANTI-TREM2 ANTIBODIES AND METHODS OF USE THEREOF

(71) Applicant: Denali Therapeutics Inc., South San Francisco, CA (US)

(72) Inventors: Mark S. Dennis, South San Francisco, CA (US); Zhenyu Gu, South San Francisco, CA (US); Mihalis S. Kariolis, South San Francisco, CA (US); Cathal S. Mahon, South San Francisco, CA (US); Kathryn M. Monroe, South San Francisco, CA (US); Joshua I. Park, South San Francisco, CA (US); Rachel Prorok, South San Francisco, CA (US); Adam P. Silverman, South San Francisco, CA (US); Bettina Van Lengerich, South San Francisco, CA (US)

(73) Assignee: Denali Therapeutics Inc., South San Francisco, CA (US)

( * ) Notice: Subject to any disclaimer, the term of this patent is extended or adjusted under 35 U.S.C. 154(b) by 0 days.

(21) Appl. No.: 17/151,006

(22) Filed: Jan. 15, 2021

(65) Prior Publication Data

US 2021/0214438 A1    Jul. 15, 2021

Related U.S. Application Data

(63) Continuation of application No. PCT/US2021/013200, filed on Jan. 13, 2021.

(60) Provisional application No. 62/960,663, filed on Jan. 13, 2020, provisional application No. 63/070,728, filed on Aug. 26, 2020, provisional application No. 63/091,717, filed on Oct. 14, 2020.

(51) Int. Cl.
*C07K 16/28* (2006.01)
*A61K 39/00* (2006.01)

(52) U.S. Cl.
CPC .... *C07K 16/2803* (2013.01); *A61K 2039/505* (2013.01); *C07K 2317/565* (2013.01); *C07K 2319/30* (2013.01)

(58) Field of Classification Search
None
See application file for complete search history.

(56) References Cited

U.S. PATENT DOCUMENTS

| 8,231,878 | B2 | 7/2012 | Colonna et al. | |
|---|---|---|---|---|
| 8,981,061 | B2 | 3/2015 | Colonna et al. | |
| 9,663,587 | B2 | 5/2017 | Hsieh et al. | |
| 10,457,717 | B2 * | 10/2019 | Chen | C07K 14/70582 |
| 10,870,837 | B2 | 12/2020 | Henry et al. | |
| 2020/0216522 | A1 * | 7/2020 | Chen | A61P 25/28 |
| 2020/0223935 | A1 * | 7/2020 | Chen | C07K 16/005 |
| 2020/0262890 | A1 * | 8/2020 | Chen | C07K 14/70582 |
| 2020/0277373 | A1 * | 9/2020 | Chen | C07K 16/40 |
| 2020/0289627 | A1 * | 9/2020 | Dennis | C07K 14/705 |
| 2020/0369746 | A1 * | 11/2020 | Chen | A61K 47/6849 |
| 2021/0070881 | A1 * | 3/2021 | Dennis | C07K 16/40 |

FOREIGN PATENT DOCUMENTS

| CN | 105218669 | A | 6/2016 | |
|---|---|---|---|---|
| KR | 10-2156165 | B1 | 9/2020 | |
| WO | 2014/178820 | A1 | 11/2014 | |
| WO | 2015/033223 | A2 | 3/2015 | |
| WO | 2016/023019 | A2 | 2/2016 | |
| WO | 2016/049641 | A1 | 3/2016 | |
| WO | 2017/058866 | A1 | 4/2017 | |
| WO | 2017/062672 | A2 | 4/2017 | |
| WO | 2017/147509 | A1 | 8/2017 | |
| WO | 2017/189959 | A1 | 11/2017 | |
| WO | 2018/015573 | A2 | 1/2018 | |
| WO | 2018/119351 | A1 | 6/2018 | |
| WO | 2018/134815 | A2 | 6/2018 | |
| WO | 2018/195506 | A1 | 10/2018 | |
| WO | 2019/021233 | A1 | 1/2019 | |
| WO | 2019/028292 | A1 | 2/2019 | |
| WO | 2019/055841 | A1 | 3/2019 | |
| WO | 2019/079529 | A1 | 4/2019 | |
| WO | 2019/118513 | A1 | 6/2019 | |
| WO | 2019/140050 | A1 | 7/2019 | |
| WO | 2019/246071 | A1 | 12/2019 | |
| WO | 2020/011968 | A1 | 1/2020 | |
| WO | 2020/037150 | A2 | 2/2020 | |
| WO | 2020/041604 | A1 | 2/2020 | |
| WO | 2020/055975 | A1 | 3/2020 | |
| WO | 2020/079580 | A1 | 4/2020 | |
| WO | 2020/112889 | A2 | 6/2020 | |
| WO | 2020/121195 | A1 | 6/2020 | |
| WO | 2020/123511 | A2 | 6/2020 | |
| WO | 2020/123664 | A1 | 6/2020 | |
| WO | 2020/172450 | A1 | 8/2020 | |
| WO | 2020/172457 | A1 | 8/2020 | |
| WO | WO-2020172450 | A1 * | 8/2020 | ............. A61P 25/28 |
| WO | WO-2020172457 | A1 * | 8/2020 | ......... C07K 16/2803 |
| WO | 2020/194317 | A1 | 10/2020 | |
| WO | 2020/206320 | A1 | 10/2020 | |

OTHER PUBLICATIONS

Gen Bank Accession No. AWK57454.1; May 2018; 2 pages.*
Gen Bank Accession No. P01834.2; Mar. 2017; 6 pages.*
U.S. Appl. No. 16/646,536, dated Mar. 2020, Chen.*
U.S. Appl. No. 16/543,332, US-2020-0223935.
U.S. Appl. No. 16/646,536, US-2020-0277373.
U.S. Appl. No. 16/782,669, US-2020-0369746.
U.S. Appl. No. 16/782,984, US-2020-0289627.
U.S. Appl. No. 16/921,506, unpublished.
U.S. Appl. No. 17/102,138, unpublished.
U.S. Appl. No. 17/159,038, unpublished.

(Continued)

*Primary Examiner* — Ilia I Ouspenski
(74) *Attorney, Agent, or Firm* — Kilpatrick Townsend & Stockton LLP

(57) ABSTRACT

In one aspect, antibodies that specifically bind to a human triggering receptor expressed on myeloid cells 2 (TREM2) protein are provided. In some embodiments, the antibody decreases levels of soluble TREM2 (sTREM2). In some embodiments, the antibody enhances TREM2 activity.

31 Claims, 32 Drawing Sheets

Specification includes a Sequence Listing.

(56) References Cited

OTHER PUBLICATIONS

U.S. Appl. No. 17/174,231, unpublished.
U.S. Appl. No. 17/178,595, unpublished.
U.S. Appl. No. 17/253,391, unpublished.
PCT/US2021/018705, unpublished.
Cheng et al., "TREM2-activating antibodies abrogate the negative pleiotropic effects of the Alzheimer's disease variant Trem$^{2R47H}$ on murine myeloid cell function", J. Biol. Chem., 2018, vol. 293, Issue 32, pp. 12620-12633.
Hsieh et al., "A Role for TREM2 Ligands in the Phagocytosis of Apoptotic Neuronal Cells by Microglia", J. Neurochem, 2009, 109(4), pp. 1144-1156.
Jiang et al., "Upregulation of TREM2 Ameliorates Neuropathology and Rescues Spatial Cognitive Impairment in a Transgenic Mouse Model of Alzheimer's Disease", Neuropsychopharmacology, 2014, 39, pp. 2949-2962.
Lewcock et al., "Emerging Microglia Biology Defines Novel Therapeutic Approaches for Alzheimer's Disease", Neuron, Dec. 9, 2020, 108(5), pp. 801-821.
Nugent et al., "TREM2 Regulates Microglial Cholesterol Metabolism upon Chronic Phagocytic Challenge", Neuron, Mar. 4, 2020, 105(5), pp. 1-18. e1-e9.
Piccio et al., "Blockade of TREM-2 exacerbates experimental autoimmune encephalomyelitis", Eur. J. Immunol., 2007, 37, pp. 1290-1301.
Schlepckow et al., "Enhancing Protective Microglial Activities with a Dual Function TREM2 Antibody to the Stalk Region", EMBO Mol Med., Apr. 7, 2020, 12(4):e11227, pp. 1-22.
Sudom et al., "Molecular basis for the loss-of-function effects of the Alzheimer's disease—associated R47H variant of the immune receptor TREM2", J. Biol. Chem., 2018, vol. 293, Issue 32, pp. 12634-12646.
Kariolis et al., "Brain delivery of therapeutic proteins using an Fc fragment blood-brain barrier transport vehicle in mice and monkeys", Sci. Transl. Med., 2020, vol. 12, Issue 545, eaay1359, pp. 1-13.
"TREM2 in Neurodegenerative Diseases", Molecular Neurodegeneration, vol. 12, Aug. 2, 2017, pp. 1-33. Available Online at https://molecularneurodegeneration.biomedcentral.com/track/pdf/10.1186/s13024-017-0197-5.pdf.
Invitation to Pay Additional Fees, Partial Search Report, and Provisional Opinion for International Appl. No. PCT/US2021/013200, dated May 7, 2021, 18 pages.
Dennis et al., U.S. Appl. No. 17/402,986, filed Aug. 16, 2021, 210 pages.
Dennis et al., U.S. Appl. No. 17/403,406, filed Aug. 16, 2021, 124 pages.

* cited by examiner

CL0020188-1

CL0020188-2

CL0020188-3

CL0020188-4

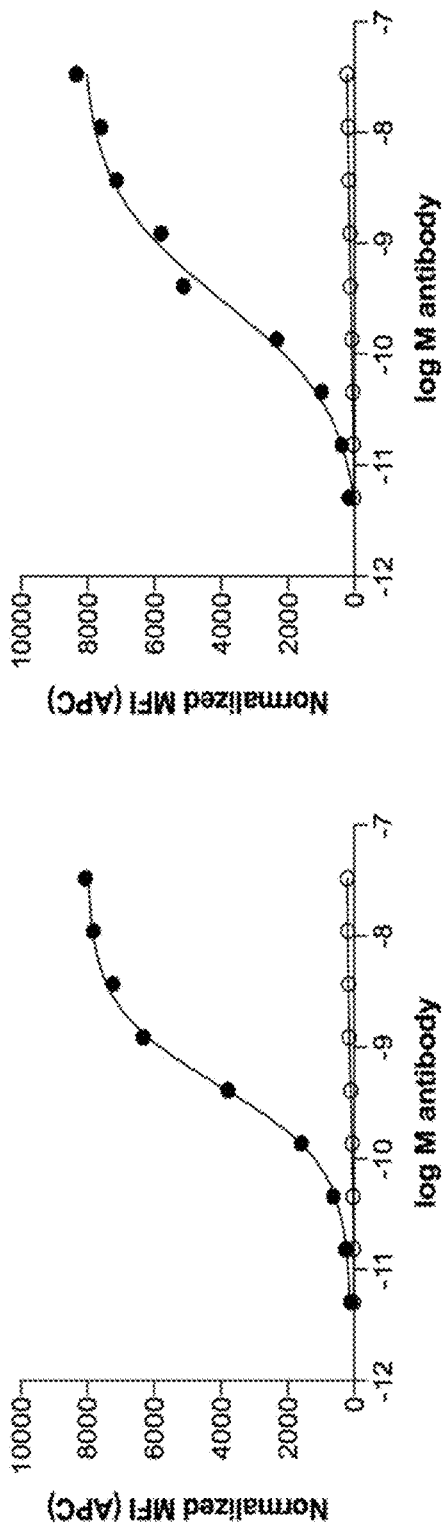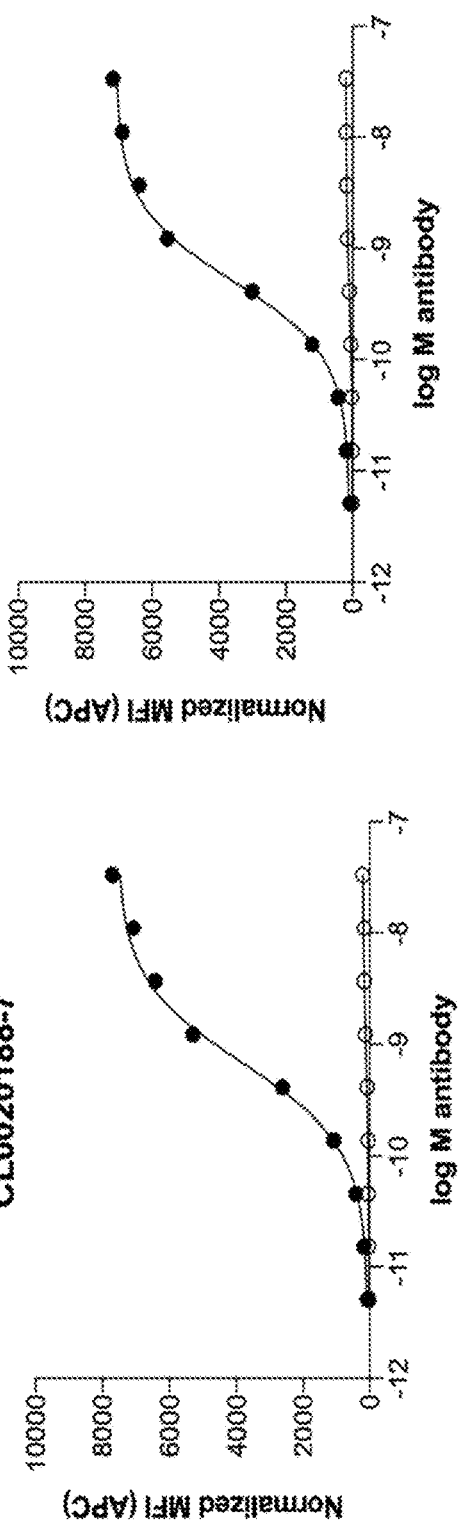

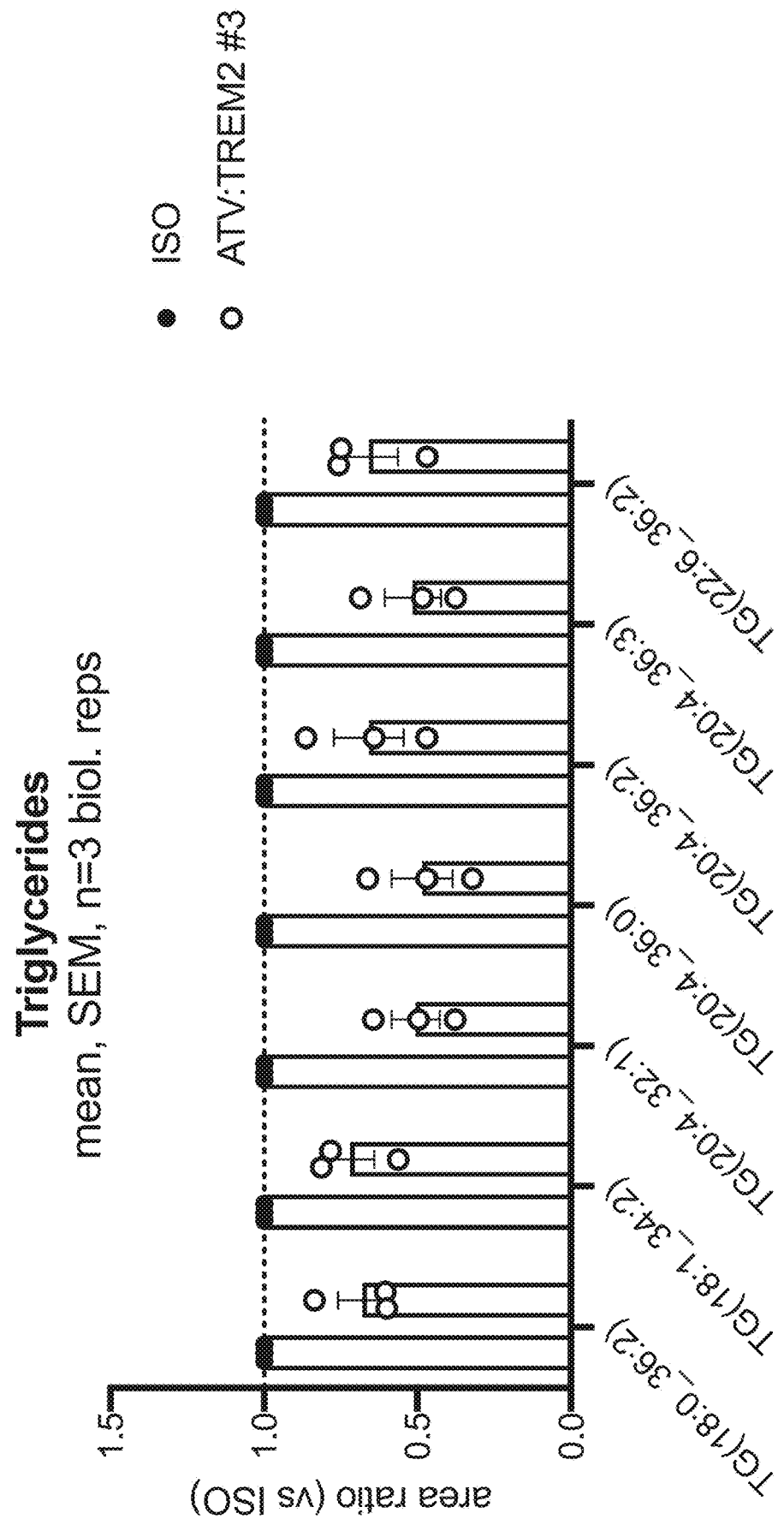

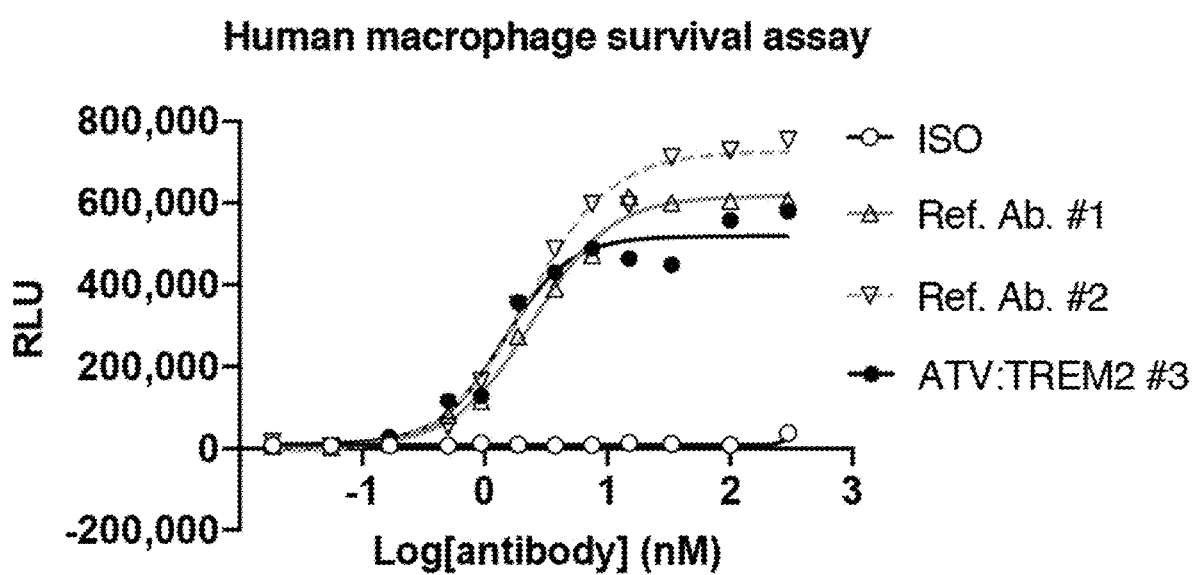

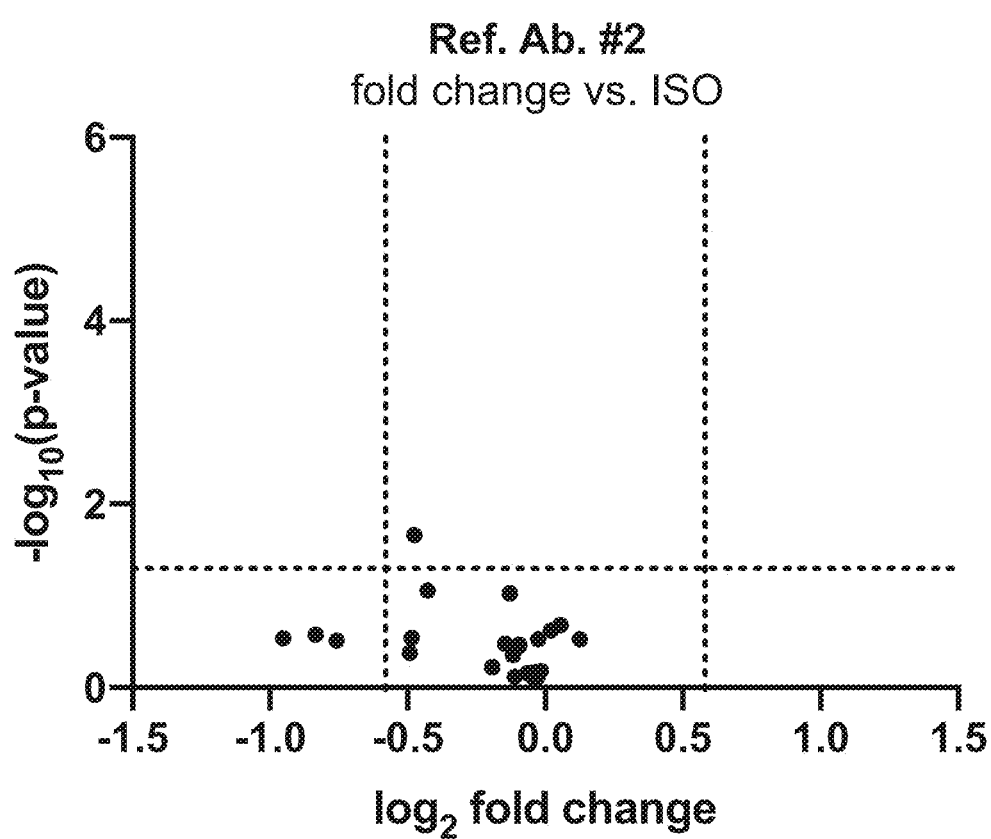

Number of new born microglia

Iba1 signal levels

ANTI-TREM2 ANTIBODIES AND METHODS OF USE THEREOF

CROSS-REFERENCE TO RELATED APPLICATIONS

The present application is a continuation of International Patent Application No. PCT/US2021/013200, filed on Jan. 13, 2021, which claims priority to U.S. Provisional Patent Application No. 62/960,663, filed on Jan. 13, 2020, U.S. Provisional Patent Application No. 63/070,728, filed on Aug. 26, 2020, and U.S. Provisional Patent Application No. 63/091,717, filed on Oct. 14, 2020, the disclosures of which are incorporated herein by reference in their entirety for all purposes.

BACKGROUND

Triggering receptor expressed on myeloid cells-2 (TREM2) is a transmembrane receptor that is expressed on microglia and is believed to function in regulating phagocytosis, cell survival, and the production of pro-inflammatory cytokines. Mutations in TREM2 have been identified in neurodegenerative diseases including Alzheimer's disease, Nasu-Hakola disease, Parkinson's disease, amyotrophic lateral sclerosis, and frontotemporal dementia. Additionally, altered levels of soluble TREM2 (sTREM2) have been reported in the cerebrospinal fluid of patients having Alzheimer's disease or frontotemporal dementia who have a mutation in TREM2.

There remains a need for therapeutic agents that modulate TREM2 activity or levels of STREM2.

BRIEF SUMMARY

In one aspect, antibodies that specifically binds to a human triggering receptor expressed on myeloid cells 2 (TREM2) are provided. In some embodiments, the antibodies comprise a modified Fc polypeptide that can bind to a transferrin receptor protein. In any of the herein disclosed embodiments, the antibody can comprise CDRs, a $V_H$, and/or a $V_L$ according to any of the exemplary sequences provided herein, and can further comprise a modified Fc polypeptide comprising transferrin receptor-binding mutations as set forth herein.

In some embodiments, an antibody that specifically binds to TREM2 comprises:

(a) a variable region comprising:
  i. a CDR-H1 sequence comprising the sequence of G-F-T-F-T-$\alpha_6$-F-Y-M-S (SEQ ID NO:28), wherein $\alpha_6$ is D or N;
  ii. a CDR-H2 sequence comprising the sequence of V-I-R-N-$\beta_5$-$\beta_6$-N-$\beta_8$-Y-T-$\beta_{11}$-$\beta_{12}$-Y-N-P-S-V-K-G (SEQ ID NO:29), wherein $\beta_5$ is K or R; $\beta_6$ is A or P; $\beta_8$ is G or A; $\beta_{11}$ is A or T; and $\beta_{12}$ is G or D;
  iii. a CDR-H3 sequence comprising the sequence of $\gamma_1$-R-L-$\gamma_4$-Y-G-F-D-Y (SEQ ID NO:30), wherein $\gamma_1$ is A or T; and $\gamma_4$ is T or S;
  iv. a CDR-L1 sequence comprising the sequence of Q-S-S-K-S-L-L-H-S-$\delta_{10}$-G-K-T-Y-L-N (SEQ ID NO:31), wherein $\delta_{10}$ is N or T;
  v. a CDR-L2 sequence comprising the sequence WMSTRAS (SEQ ID NO:8); and
  vi. a CDR-L3 sequence comprising the sequence of Q-Q-F-L-E-$\phi_6$-P-F-T (SEQ ID NO:32), wherein $\phi_6$ is Y or F;

(b) a first Fc polypeptide that is modified to specifically bind to a transferrin receptor; and
(c) a second Fc polypeptide.

In some embodiments, the first Fc polypeptide and the second Fc polypeptide associate to form an Fc dimer.

In some embodiments, the CDR-H1 sequence is selected from SEQ ID NOS:4 or 12. In some embodiments, the CDR-H2 sequence is selected from SEQ ID NOS:5, 13, or 25. In some embodiments, the CDR-H3 sequence is selected from SEQ ID NOS:6, 14, or 17. In some embodiments, the CDR-L1 sequence is selected from SEQ ID NOS:7 or 23. In some embodiments, the CDR-L3 sequence is selected from SEQ ID NOS:9 or 18.

In some embodiments, the variable region comprises:
(a) a CDR-H1 comprising the amino acid sequence of SEQ ID NO:4, a CDR-H2 comprising the amino acid sequence of SEQ ID NO:5, a CDR-H3 comprising the amino acid sequence of SEQ ID NO: 17, a CDR-L1 comprising the amino acid sequence of SEQ ID NO:7, a CDR-L2 comprising the amino acid sequence of SEQ ID NO:8, and a CDR-L3 comprising the amino acid sequence of SEQ ID NO: 18; or
(b) a CDR-H1 comprising the amino acid sequence of SEQ ID NO:4, a CDR-H2 comprising the amino acid sequence of SEQ ID NO:5, a CDR-H3 comprising the amino acid sequence of SEQ ID NO: 17, a CDR-L1 comprising the amino acid sequence of SEQ ID NO:23, a CDR-L2 comprising the amino acid sequence of SEQ ID NO:8, and a CDR-L3 comprising the amino acid sequence of SEQ ID NO: 18; or
(c) a CDR-H1 comprising the amino acid sequence of SEQ ID NON, a CDR-H2 comprising the amino acid sequence of SEQ ID NO:25, a CDR-H3 comprising the amino acid sequence of SEQ ID NO: 17, a CDR-L1 comprising the amino acid sequence of SEQ ID NO:7, a CDR-L2 comprising the amino acid sequence of SEQ ID NO:8, and a CDR-L3 comprising the amino acid sequence of SEQ ID NO: 18; or
(d) a CDR-H1 comprising the amino acid sequence of SEQ ID NON, a CDR-H2 comprising the amino acid sequence of SEQ ID NO:25, a CDR-H3 comprising the amino acid sequence of SEQ ID NO: 17, a CDR-L1 comprising the amino acid sequence of SEQ ID NO:23, a CDR-L2 comprising the amino acid sequence of SEQ ID NO:8, and a CDR-L3 comprising the amino acid sequence of SEQ ID NO: 18; or
(e) a CDR-H1 comprising the amino acid sequence of SEQ ID NON, a CDR-H2 comprising the amino acid sequence of SEQ ID NON, a CDR-H3 comprising the amino acid sequence of SEQ ID NON, a CDR-L1 comprising the amino acid sequence of SEQ ID NON, a CDR-L2 comprising the amino acid sequence of SEQ ID NO:8, and a CDR-L3 comprising the amino acid sequence of SEQ ID NON; or
(f) a CDR-H1 comprising the amino acid sequence of SEQ ID NO: 12, a CDR-H2 comprising the amino acid sequence of SEQ ID NO: 13, a CDR-H3 comprising the amino acid sequence of SEQ ID NO: 14, a CDR-L1 comprising the amino acid sequence of SEQ ID NON, a CDR-L2 comprising the amino acid sequence of SEQ ID NO:8, and a CDR-L3 comprising the amino acid sequence of SEQ ID NON; or
(g) a CDR-H1 comprising the amino acid sequence of SEQ ID NON, a CDR-H2 comprising the amino acid sequence of SEQ ID NO:25, a CDR-H3 comprising the amino acid sequence of SEQ ID NO: 17, a CDR-L1 comprising the amino acid sequence of SEQ ID NON, a CDR-L2 comprising the amino acid sequence of SEQ ID NO:8, and a CDR-L3 comprising the amino acid sequence of SEQ ID NON.

In some embodiments, the variable region comprises a $V_H$ sequence that has at least 85% sequence identity to any one of SEQ ID NOS:2, 10, 15, 19, 21, 24, and 26.

In certain embodiments, the $V_H$ sequence has at least 90% sequence identity to SEQ ID NO: 15. In certain embodiments, the $V_H$ sequence has at least 95% sequence identity to SEQ ID NO: 15. In certain embodiments, the $V_H$ sequence comprises SEQ ID NO: 15.

In certain embodiments, the $V_H$ sequence has at least 90% sequence identity to SEQ ID NO:24. In certain embodiments, the $V_H$ sequence has at least 95% sequence identity to SEQ ID NO:24. In certain embodiments, the $V_H$ sequence comprises SEQ ID NO:24.

In some embodiments of this aspect, the variable region comprises a $V_L$ sequence has at least 85% sequence identity to any one of SEQ ID NOS:3, 11, 16, 20, 22, and 27.

In certain embodiments, the $V_L$ sequence has at least 90% sequence identity to SEQ ID NO: 16. In certain embodiments, the $V_L$ sequence has at least 95% sequence identity to SEQ ID NO: 16. In certain embodiments, the $V_L$ sequence comprises SEQ ID NO: 16.

In certain embodiments, the $V_L$ sequence has at least 90% sequence identity to SEQ ID NO:22. In certain embodiments, the $V_L$ sequence has at least 95% sequence identity to SEQ ID NO:22. In certain embodiments, the $V_L$ sequence comprises SEQ ID NO:22.

In certain embodiments, the $V_L$ sequence has at least 90% sequence identity to SEQ ID NO:27. In certain embodiments, the $V_L$ sequence has at least 95% sequence identity to SEQ ID NO:27. In certain embodiments, the $V_L$ sequence comprises SEQ ID NO:27.

In some embodiments of this aspect, the variable region comprises:
- (a) a $V_H$ sequence comprising SEQ ID NO: 15 and a $V_L$ sequence comprising SEQ ID NO: 16; or
- (b) a $V_H$ sequence comprising SEQ ID NO: 19 and a $V_L$ sequence comprising SEQ ID NO:20; or
- (c) a $V_H$ sequence comprising SEQ ID NO:21 and a $V_L$ sequence comprising SEQ ID NO:20; or
- (d) a $V_H$ sequence comprising SEQ ID NO: 19 and a $V_L$ sequence comprising SEQ ID NO:22; or
- (e) a $V_H$ sequence comprising SEQ ID NO:21 and a $V_L$ sequence comprising SEQ ID NO:22; or
- (f) a $V_H$ sequence comprising SEQ ID NO:24 and a $V_L$ sequence comprising SEQ ID NO:20; or
- (g) a $V_H$ sequence comprising SEQ ID NO:26 and a $V_L$ sequence comprising SEQ ID NO:20; or
- (h) a $V_H$ sequence comprising SEQ ID NO:24 and a $V_L$ sequence comprising SEQ ID NO:22; or
- (i) a $V_H$ sequence comprising SEQ ID NO:26 and a $V_L$ sequence comprising SEQ ID NO:22; or
- (j) a $V_H$ sequence comprising SEQ ID NO:2 and a $V_L$ sequence comprising SEQ ID NO:3; or
- (k) a $V_H$ sequence comprising SEQ ID NO: 10 and a $V_L$ sequence comprising SEQ ID NO: 11; or
- (l) a $V_H$ sequence comprising SEQ ID NO:24 and a $V_L$ sequence comprising SEQ ID NO:27.

In some embodiments of this aspect, the first Fc polypeptide comprises: Trp, Leu, or Glu at position 380; Tyr or Phe at position 384; Thr at position 386; Glu at position 387; Trp at position 388; Ser, Ala, or Val at position 389; Ser or Asn at position 390; Thr or Ser at position 413; Glu or Ser at position 415; Glu at position 416; and Phe at position 421, according to EU numbering. In some embodiments, the first Fc polypeptide binds to the apical domain of the transferrin receptor. In particular embodiments, the antibody has improved brain uptake compared to an antibody having a wild-type Fc dimer.

In certain embodiments, the first Fc polypeptide has a T366W substitution and the second Fc polypeptide has T366S, L368A, and Y407V substitutions, according to EU numbering.

In other embodiments, the first Fc polypeptide has T366S, L368A, and Y407V substitutions and the second Fc polypeptide has a T366W substitution, according to EU numbering.

In some embodiments, the first Fc polypeptide and/or the second Fc polypeptide comprises a modification that reduces effector function. In certain embodiments, the modification that reduces effector function comprises the substitutions of Ala at position 234 and Ala at position 235, according to EU numbering.

In some embodiments, the first Fc polypeptide and/or the second Fc polypeptide comprises amino acid modifications relative to the native Fc sequence that extend serum half-life. In certain embodiments, the amino acid modifications comprise substitutions of Leu at position 428 and Ser at position 434, according to EU numbering.

In some embodiments of this aspect, the first Fc polypeptide comprises the sequence of SEQ ID NO:41 or SEQ ID NO:64, and the second Fc polypeptide comprises the sequence of SEQ ID NO:39 or SEQ ID NO:63. In certain embodiments, the antibody comprises: (i) a first heavy chain (HC) comprising a $V_H$ comprising SEQ ID NO:24 and the first Fc polypeptide comprising SEQ ID NO:41; (ii) a second heavy chain (HC) comprising a $V_H$ comprising SEQ ID NO:24 and the second Fc polypeptide comprising SEQ ID NO:39; and (iii) two light chains each comprising a $V_L$ comprising SEQ ID NO:22. In certain embodiments, the antibody comprises: (i) a first heavy chain (HC) comprising a VH comprising SEQ ID NO:24 and the first Fc polypeptide comprising SEQ ID NO:64; (ii) a second heavy chain (HC) comprising a VH comprising SEQ ID NO:24 and the second Fc polypeptide comprising SEQ ID NO:63; and (iii) two light chains each comprising a VL comprising SEQ ID NO:22. In particular embodiments, the antibody comprises: (i) a first heavy chain (HC) that comprises or consists of the amino acid sequence set forth in SEQ ID NO:42; (ii) a second HC that comprises or consists of the amino acid sequence set forth in SEQ ID NO:53; and (iii) a first and a second light chain (LC) that each comprises or consists of the amino acid sequence set forth in SEQ ID NO:54. In certain embodiments, the antibody comprises: (i) a first heavy chain (HC) that comprises or consists of the amino acid sequence set forth in SEQ ID NO:65; (ii) a second HC that comprises or consists of the amino acid sequence set forth in SEQ ID NO:73; and (iii) a first and a second light chain (LC) that each comprises or consists of the amino acid sequence set forth in SEQ ID NO:54.

In some embodiments of this aspect, the first Fc polypeptide comprises the sequence of SEQ ID NO:44 or SEQ ID NO:66, and the second Fc polypeptide comprises the sequence of SEQ ID NO:39 or SEQ ID NO:63. In certain embodiments, the antibody comprises: (i) a first heavy chain (HC) comprising a $V_H$ comprising SEQ ID NO:24 and the first Fc polypeptide comprising SEQ ID NO:44; (ii) a second heavy chain (HC) comprising a $V_H$ comprising SEQ ID NO:24 and the second Fc polypeptide comprising SEQ ID NO:39; and (iii) two light chains each comprising a $V_L$ comprising SEQ ID NO:22. In certain embodiments, the antibody comprises: (i) a first heavy chain (HC) comprising a VH comprising SEQ ID NO:24 and the first Fc polypeptide comprising SEQ ID NO:66; (ii) a second heavy chain (HC) comprising a VH comprising SEQ ID NO:24 and the second Fc polypeptide comprising SEQ ID NO:63; and (iii) two light chains each comprising a VL comprising SEQ ID NO:22. In particular embodiments, the antibody comprises: (i) a first heavy chain (HC) that comprises or consists of the amino acid sequence set forth in SEQ ID NO:45; (ii) a second HC that comprises or consists of the amino acid sequence set forth in SEQ ID NO:53; and (iii) a first and a second light chain (LC) that each comprises or consists of the amino acid sequence set forth in SEQ ID NO:54. In certain embodiments, the antibody comprises: (i) a first heavy chain (HC) that comprises or consists of the amino acid sequence set forth in SEQ ID NO:67; (ii) a second HC that comprises or consists of the amino acid sequence set forth in SEQ ID NO:73; and (iii) a first and a second light chain (LC) that each comprises or consists of the amino acid sequence set forth in SEQ ID NO:54.

In some embodiments of this aspect, the first Fc polypeptide comprises the sequence of SEQ ID NO:47 or SEQ ID NO:68, and the second Fc polypeptide comprises the sequence of SEQ ID NO:39 or SEQ ID NO:63. In certain embodiments, the antibody comprises: (i) a first heavy chain (HC) comprising a $V_H$ comprising SEQ ID NO:24 and the first Fc polypeptide comprising SEQ ID NO:47; (ii) a second heavy chain (HC) comprising a $V_H$ comprising SEQ ID NO:24 and the second Fc polypeptide comprising SEQ ID NO:39; and (iii) two light chains each comprising a $V_L$ comprising SEQ ID NO:22. In certain embodiments, the antibody comprises: (i) a first heavy chain (HC) comprising a VH comprising SEQ ID NO:24 and the first Fc polypeptide comprising SEQ ID NO:68; (ii) a second heavy chain (HC) comprising a VH comprising SEQ ID NO:24 and the second Fc polypeptide comprising SEQ ID NO:63; and (iii) two light chains each comprising a VL comprising SEQ ID NO:22. In particular embodiments, the antibody comprises: (i) a first heavy chain (HC) that comprises or consists of the amino acid sequence set forth in SEQ ID NO:48; (ii) a second HC that comprises or consists of the amino acid sequence set forth in SEQ ID NO:53; and (iii) a first and a second light chain (LC) that each comprises or consists of the amino acid sequence set forth in SEQ ID NO:54. In certain embodiments, the antibody comprises: (i) a first heavy chain (HC) that comprises or consists of the amino acid sequence set forth in SEQ ID NO:69; (ii) a second HC that comprises or consists of the amino acid sequence set forth in SEQ ID NO:73; and (iii) a first and a second light chain (LC) that each comprises or consists of the amino acid sequence set forth in SEQ ID NO:54.

In some embodiments of this aspect, the first Fc polypeptide comprises the sequence of SEQ ID NO:47 or SEQ ID NO:68, and the second Fc polypeptide comprises the sequence of SEQ ID NO:61 or SEQ ID NO:84. In certain embodiments, the antibody comprises: (i) a first heavy chain (HC) comprising a $V_H$ comprising SEQ ID NO:24 and the first Fc polypeptide comprising SEQ ID NO:47; (ii) a second heavy chain (HC) comprising a $V_H$ comprising SEQ ID NO:24 and the second Fc polypeptide comprising SEQ ID NO:61; and (iii) two light chains each comprising a $V_L$ comprising SEQ ID NO:22. In certain embodiments, the antibody comprises: (i) a first heavy chain (HC) comprising a VH comprising SEQ ID NO:24 and the first Fc polypeptide comprising SEQ ID NO:68; (ii) a second heavy chain (HC) comprising a VH comprising SEQ ID NO:24 and the second Fc polypeptide comprising SEQ ID NO:84; and (iii) two light chains each comprising a VL comprising SEQ ID NO:22. In particular embodiments, the antibody comprises: (i) a first heavy chain (HC) that comprises or consists of the amino acid sequence set forth in SEQ ID NO:48; (ii) a second HC that comprises or consists of the amino acid sequence set forth in SEQ ID NO:52; and (iii) a first and a second light chain (LC) that each comprises or consists of the amino acid sequence set forth in SEQ ID NO:54. In certain embodiments, the antibody comprises: (i) a first heavy chain (HC) that comprises or consists of the amino acid sequence set forth in SEQ ID NO:69; (ii) a second HC that comprises or consists of the amino acid sequence set forth in SEQ ID NO:72; and (iii) a first and a second light chain (LC) that each comprises or consists of the amino acid sequence set forth in SEQ ID NO:54.

In some embodiments of this aspect, the first Fc polypeptide comprises the sequence of SEQ ID NO:50 or SEQ ID NO:70, and the second Fc polypeptide comprises the sequence of SEQ ID NO:39 or SEQ ID NO:63. In certain embodiments, the antibody comprises: (i) a first heavy chain (HC) comprising a $V_H$ comprising SEQ ID NO:24 and the first Fc polypeptide comprising SEQ ID NO:50; (ii) a second heavy chain (HC) comprising a $V_H$ comprising SEQ ID NO:24 and the second Fc polypeptide comprising SEQ ID NO:39; and (iii) two light chains each comprising a $V_L$ comprising SEQ ID NO:22. In certain embodiments, the antibody comprises: (i) a first heavy chain (HC) comprising a VH comprising SEQ ID NO:24 and the first Fc polypeptide comprising SEQ ID NO:70; (ii) a second heavy chain (HC) comprising a VH comprising SEQ ID NO:24 and the second Fc polypeptide comprising SEQ ID NO:63; and (iii) two light chains each comprising a VL comprising SEQ ID NO:22. In particular embodiments, the antibody comprises: (i) a first heavy chain (HC) that comprises or consists of the amino acid sequence set forth in SEQ ID NO:51; (ii) a second HC that comprises or consists of the amino acid sequence set forth in SEQ ID NO:53; and (iii) a first and a second light chain (LC) that each comprises or consists of the amino acid sequence set forth in SEQ ID NO:54. In certain embodiments, the antibody comprises: (i) a first heavy chain (HC) that comprises or consists of the amino acid sequence set forth in SEQ ID NO:71; (ii) a second HC that comprises or consists of the amino acid sequence set forth in SEQ ID NO:73; and (iii) a first and a second light chain (LC) that each comprises or consists of the amino acid sequence set forth in SEQ ID NO:54.

In another aspect, the disclosure provides an isolated antibody that specifically binds to a human triggering receptor expressed on myeloid cells 2 (TREM2), wherein the antibody comprises: (i) a first heavy chain (HC) comprising a $V_H$ comprising SEQ ID NO:24 and the first Fc polypeptide comprising SEQ ID NO:41; (ii) a second heavy chain (HC) comprising a $V_H$ comprising SEQ ID NO:24 and the second Fc polypeptide comprising SEQ ID NO:39; and (iii) two light chains each comprising a $V_L$ comprising SEQ ID NO:22. In some embodiments, the antibody comprises: (i) a first heavy chain (HC) that comprises or consists of the amino acid sequence set forth in SEQ ID NO:42; (ii) a second HC that comprises or consists of the amino acid sequence set forth in SEQ ID NO:53; and (iii) a first and a second light chain (LC) that each comprises or consists of the amino acid sequence set forth in SEQ ID NO:54.

In another aspect, the disclosure provides an isolated antibody that specifically binds to a human triggering receptor expressed on myeloid cells 2 (TREM2), wherein the antibody comprises: (i) a first heavy chain (HC) comprising a $V_H$ comprising SEQ ID NO:24 and the first Fc polypeptide comprising SEQ ID NO:64; (ii) a second heavy chain (HC)

comprising a $V_H$ comprising SEQ ID NO:24 and the second Fc polypeptide comprising SEQ ID NO:63; and (iii) two light chains each comprising a $V_L$ comprising SEQ ID NO:22. In some embodiments, the antibody comprises: (i) a first heavy chain (HC) that comprises or consists of the amino acid sequence set forth in SEQ ID NO:65; (ii) a second HC that comprises or consists of the amino acid sequence set forth in SEQ ID NO:73; and (iii) a first and a second light chain (LC) that each comprises or consists of the amino acid sequence set forth in SEQ ID NO:54.

In another aspect, the disclosure provides an isolated antibody that specifically binds to a human triggering receptor expressed on myeloid cells 2 (TREM2), wherein the antibody comprises: (i) a first heavy chain (HC) comprising a $V_H$ comprising SEQ ID NO:24 and the first Fc polypeptide comprising SEQ ID NO:44; (ii) a second heavy chain (HC) comprising a $V_H$ comprising SEQ ID NO:24 and the second Fc polypeptide comprising SEQ ID NO:39; and (iii) two light chains each comprising a $V_L$ comprising SEQ ID NO:22. In some embodiments, the antibody comprises: (i) a first heavy chain (HC) that comprises or consists of the amino acid sequence set forth in SEQ ID NO:45; (ii) a second HC that comprises or consists of the amino acid sequence set forth in SEQ ID NO:53; and (iii) a first and a second light chain (LC) that each comprises or consists of the amino acid sequence set forth in SEQ ID NO:54.

In another aspect, the disclosure provides an isolated antibody that specifically binds to a human triggering receptor expressed on myeloid cells 2 (TREM2), wherein the antibody comprises: (i) a first heavy chain (HC) comprising a $V_H$ comprising SEQ ID NO:24 and the first Fc polypeptide comprising SEQ ID NO:66; (ii) a second heavy chain (HC) comprising a $V_H$ comprising SEQ ID NO:24 and the second Fc polypeptide comprising SEQ ID NO:63; and (iii) two light chains each comprising a $V_L$ comprising SEQ ID NO:22. In some embodiments, the antibody comprises: (i) a first heavy chain (HC) that comprises or consists of the amino acid sequence set forth in SEQ ID NO:67; (ii) a second HC that comprises or consists of the amino acid sequence set forth in SEQ ID NO:73; and (iii) a first and a second light chain (LC) that each comprises or consists of the amino acid sequence set forth in SEQ ID NO:54.

In another aspect, the disclosure provides an isolated antibody that specifically binds to a human triggering receptor expressed on myeloid cells 2 (TREM2), wherein the antibody comprises: (i) a first heavy chain (HC) comprising a $V_H$ comprising SEQ ID NO:24 and the first Fc polypeptide comprising SEQ ID NO:47; (ii) a second heavy chain (HC) comprising a $V_H$ comprising SEQ ID NO:24 and the second Fc polypeptide comprising SEQ ID NO:39; and (iii) two light chains each comprising a $V_L$ comprising SEQ ID NO:22. In some embodiments, the antibody comprises: (i) a first heavy chain (HC) that comprises or consists of the amino acid sequence set forth in SEQ ID NO:48; (ii) a second HC that comprises or consists of the amino acid sequence set forth in SEQ ID NO:53; and (iii) a first and a second light chain (LC) that each comprises or consists of the amino acid sequence set forth in SEQ ID NO:54.

In another aspect, the disclosure provides an isolated antibody that specifically binds to a human triggering receptor expressed on myeloid cells 2 (TREM2), wherein the antibody comprises: (i) a first heavy chain (HC) comprising a VH comprising SEQ ID NO:24 and the first Fc polypeptide comprising SEQ ID NO:68; (ii) a second heavy chain (HC) comprising a VH comprising SEQ ID NO:24 and the second Fc polypeptide comprising SEQ ID NO:63; and (iii) two light chains each comprising a VL comprising SEQ ID NO:22. In some embodiments, the antibody comprises: (i) a first heavy chain (HC) that comprises or consists of the amino acid sequence set forth in SEQ ID NO:69; (ii) a second HC that comprises or consists of the amino acid sequence set forth in SEQ ID NO:73; and (iii) a first and a second light chain (LC) that each comprises or consists of the amino acid sequence set forth in SEQ ID NO:54.

In another aspect, the disclosure provides an isolated antibody that specifically binds to a human triggering receptor expressed on myeloid cells 2 (TREM2), wherein the antibody comprises: (i) a first heavy chain (HC) comprising a $V_H$ comprising SEQ ID NO:24 and the first Fc polypeptide comprising SEQ ID NO:47 (ii) a second heavy chain (HC) comprising a $V_H$ comprising SEQ ID NO:24 and the second Fc polypeptide comprising SEQ ID NO:61; and (iii) two light chains each comprising a $V_L$ comprising SEQ ID NO:22. In some embodiments, (i) a first heavy chain (HC) that comprises or consists of the amino acid sequence set forth in SEQ ID NO:48; (ii) a second HC that comprises or consists of the amino acid sequence set forth in SEQ ID NO:52; and (iii) a first and a second light chain (LC) that each comprises or consists of the amino acid sequence set forth in SEQ ID NO:54.

In another aspect, the disclosure provides an isolated antibody that specifically binds to a human triggering receptor expressed on myeloid cells 2 (TREM2), wherein the antibody comprises: (i) a first heavy chain (HC) comprising a VH comprising SEQ ID NO:24 and the first Fc polypeptide comprising SEQ ID NO:68; (ii) a second heavy chain (HC) comprising a VH comprising SEQ ID NO:24 and the second Fc polypeptide comprising SEQ ID NO:61; and (iii) two light chains each comprising a VL comprising SEQ ID NO:22. In some embodiments, the antibody comprises: (i) a first heavy chain (HC) that comprises or consists of the amino acid sequence set forth in SEQ ID NO:69; (ii) a second HC that comprises or consists of the amino acid sequence set forth in SEQ ID NO:72; and (iii) a first and a second light chain (LC) that each comprises or consists of the amino acid sequence set forth in SEQ ID NO:54.

In another aspect, the disclosure provides an isolated antibody that specifically binds to a human triggering receptor expressed on myeloid cells 2 (TREM2), wherein the antibody comprises: (i) a first heavy chain (HC) comprising a $V_H$ comprising SEQ ID NO:24 and the first Fc polypeptide comprising SEQ ID NO:50; (ii) a second heavy chain (HC) comprising a $V_H$ comprising SEQ ID NO:24 and the second Fc polypeptide comprising SEQ ID NO:39; and (iii) two light chains each comprising a $V_L$ comprising SEQ ID NO:22. In some embodiments, the antibody comprises: (i) a first heavy chain (HC) that comprises or consists of the amino acid sequence set forth in SEQ ID NO:51; (ii) a second HC that comprises or consists of the amino acid sequence set forth in SEQ ID NO:53; and (iii) a first and a second light chain (LC) that each comprises or consists of the amino acid sequence set forth in SEQ ID NO:54.

In another aspect, the disclosure provides an isolated antibody that specifically binds to a human triggering receptor expressed on myeloid cells 2 (TREM2), wherein the antibody comprises: (i) a first heavy chain (HC) comprising a VH comprising SEQ ID NO:24 and the first Fc polypeptide comprising SEQ ID NO:70; (ii) a second heavy chain (HC) comprising a VH comprising SEQ ID NO:24 and the second Fc polypeptide comprising SEQ ID NO:63; and (iii) two light chains each comprising a VL comprising SEQ ID NO:22. In some embodiments, the antibody comprises: (i) a first heavy chain (HC) that comprises or consists of the amino acid sequence set forth in SEQ ID NO:71; (ii) a second HC that comprises or consists of the amino acid sequence set forth in SEQ ID NO:73; and (iii) a first and a second light chain (LC) that each comprises or consists of the amino acid sequence set forth in SEQ ID NO:54.

In some embodiments of any of the aspects described herein, the antibody decreases levels of soluble TREM2 protein (sTREM2). In some embodiments, the antibody enhances TREM2 activity. In some embodiments, the antibody enhances phagocytosis or enhances the migration, differentiation, function, or survival of myeloid cells, microglia, or macrophages. In some embodiments, the antibody enhances microglia function without increasing neuroinflammation. In some embodiments, the antibody enhances Syk phosphorylation. In some embodiments, the antibody enhances Syk phosphorylation in the presence of a TREM2 ligand. In some embodiments, the antibody exhibits cross-reactivity with a cynomolgus TREM2 protein.

In another aspect, the disclosure provides a pharmaceutical composition comprising the isolated antibody described herein and a pharmaceutically acceptable carrier.

In another aspect, the disclosure provides a kit comprising: the isolated antibody described herein or the pharmaceutical composition described herein; and instructions for use thereof.

In another aspect, the disclosure provides a method of treating a neurodegenerative disease in a subject, comprising administering to the subject the isolated antibody described herein or the pharmaceutical composition described herein. In some embodiments, the neurodegenerative disease is selected from the group consisting of: Alzheimer's disease, primary age-related tauopathy, progressive supranuclear palsy (PSP), frontotemporal dementia, frontotemporal dementia with parkinsonism linked to chromosome 17, argyrophilic grain dementia, amyotrophic lateral sclerosis, amyotrophic lateral sclerosis/parkinsonism-dementia complex of Guam (ALS-PDC), corticobasal degeneration, chronic traumatic encephalopathy, Creutzfeldt-Jakob disease, dementia pugilistica, diffuse neurofibrillary tangles with calcification, Down's syndrome, familial British dementia, familial Danish dementia, Gerstmann-Straussler-Scheinker disease, globular glial tauopathy, Guadeloupean parkinsonism with dementia, Guadelopean PSP, Hallevorden-Spatz disease, hereditary diffuse leukoencephalopathy with spheroids (HDLS), Huntington's disease, inclusion-body myositis, multiple system atrophy, myotonic dystrophy, Nasu-Hakola disease, neurofibrillary tangle-predominant dementia, Niemann-Pick disease type C, pallidoponto-nigral degeneration, Parkinson's disease, Pick's disease, postencephalitic parkinsonism, prion protein cerebral amyloid angiopathy, progressive subcortical gliosis, subacute sclerosing panencephalitis, and tangle only dementia.

In another aspect, the disclosure provides a method of decreasing levels of sTREM2 in a subject having a neurodegenerative disease, comprising administering to the subject the isolated antibody described herein or the pharmaceutical composition described herein.

In another aspect, the disclosure provides a method of enhancing TREM2 activity in a subject having a neurodegenerative disease, comprising administering to the subject the isolated antibody described herein or the pharmaceutical composition described herein.

In another aspect, the disclosure provides an isolated polynucleotide comprising a nucleotide sequence encoding the antibody described herein.

In another aspect, the disclosure provides an isolated polynucleotide comprising a nucleotide sequence encoding any one of SEQ ID NOS:42, 45, 48, 51, 53, 54, and 61.

In another aspect, the disclosure provides an isolated polynucleotide comprising a nucleotide sequence encoding SEQ ID NOS:42, 53, and 54.

In another aspect, the disclosure provides an isolated polynucleotide comprising a nucleotide sequence encoding SEQ ID NOS:45, 53, and 54.

In another aspect, the disclosure provides an isolated polynucleotide comprising a nucleotide sequence encoding SEQ ID NOS:48, 53, and 54.

In another aspect, the disclosure provides an isolated polynucleotide comprising a nucleotide sequence encoding SEQ ID NOS:48, 52, and 54.

In another aspect, the disclosure provides an isolated polynucleotide comprising a nucleotide sequence encoding SEQ ID NOS:51, 53, and 54.

In another aspect, the disclosure provides a vector comprising the polynucleotide described herein.

In another aspect, the disclosure provides a host cell comprising the polynucleotide described herein or the vector described herein.

In another aspect, the disclosure provides a method of expressing an antibody that specifically binds to a human triggering receptor expressed on myeloid cells 2 (TREM2), comprising: culturing the host cell described herein in under conditions suitable for expression of the antibody.

BRIEF DESCRIPTION OF THE DRAWINGS

FIGS. 1A-1H include dose-titrated cell binding curves in human TREM2-Dap12 overexpressing HEK cells for humanized and sequence optimized variants of a representative anti-TREM2 antibody (CL0020188).

FIGS. 6A-6C include bar graphs illustrating the change in levels of specific triglyceride, ceramide, and acyl carnitine species in iPSC-derived microglial cells treated with ATV:TREM2 after myelin challenge.

FIG. 11A is a dose-response curve for cell viability in human macrophage cells treated with anti-TREM2 antibodies.

FIGS. 13A-13C include volcano plots that illustrate relative changes in triglyceride species in iPSC-derived microglial cells treated with anti-TREM2 antibodies.

DETAILED DESCRIPTION

I. Introduction

Figure 1A:
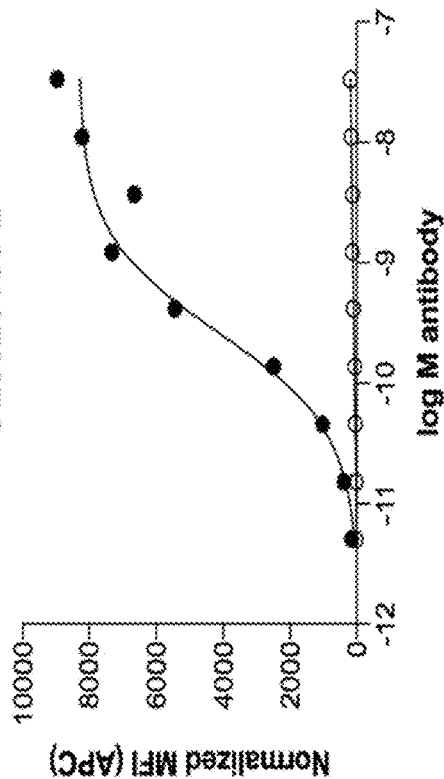
Figure 1B:
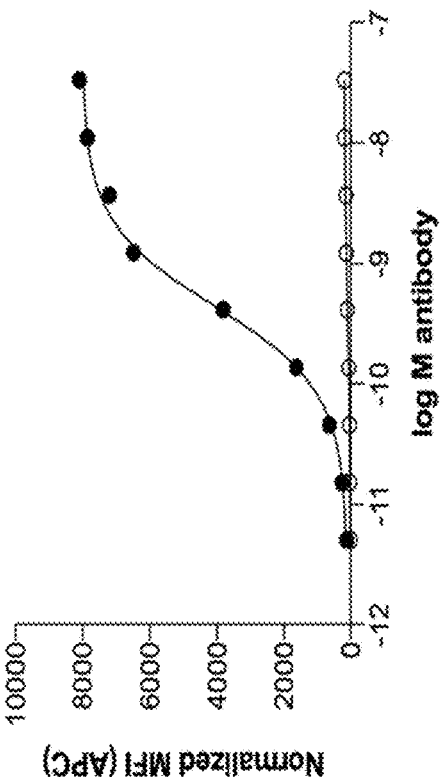
Figure 1C:
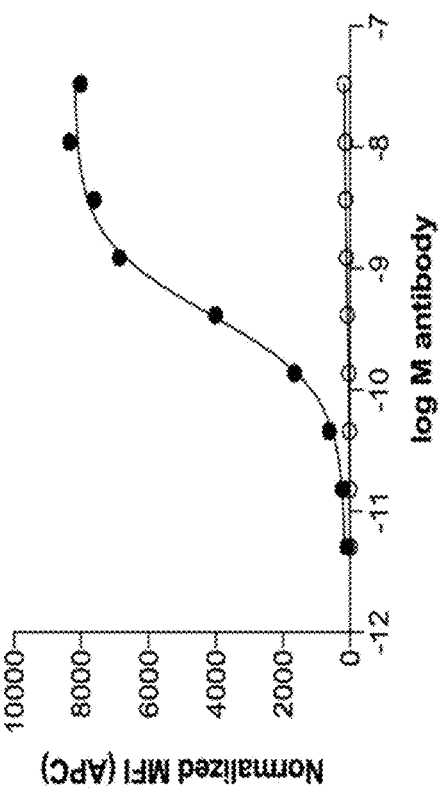
Figure 1D:
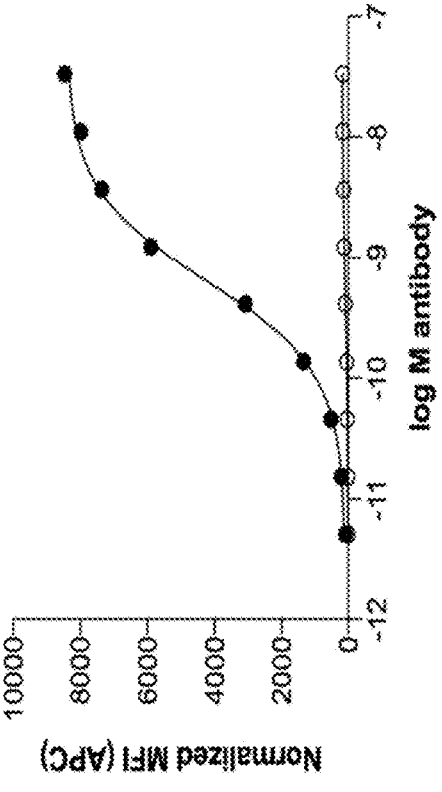

TREM2 is a transmembrane receptor that is expressed on the cell surface of microglia, dendritic cells, macrophages, and osteoclasts. Without being bound to a particular theory, it is believed that upon ligand binding, TREM2 forms a signaling complex with a transmembrane adapter protein, DNAX-activating protein 12 (DAP12), which in turn is tyrosine phosphorylated by the protein kinase SRC. It is believed that the activated TREM2/DAP12 signaling complex mediates intracellular signaling by recruiting and phosphorylating kinases such as Syk kinase. TREM2/DAP12 signaling modulates activities such as phagocytosis, cell growth and survival, pro-inflammatory cytokine secretion, and the migration of cells such as microglia and macrophages. TREM2 undergoes regulated intramembrane proteolysis, in which the membrane-associated full-length TREM2 is cleaved by the metalloprotease ADAM10 into a sTREM2 portion that is shed from the cell and a membrane-retained C-terminal fragment that is further degraded by a gamma-secretase. Altered levels of sTREM2 have been reported in patients having Alzheimer's disease or frontotemporal dementia and having a mutation in TREM2. Additionally, mutations in TREM2 are associated with altered functions such as impaired phagocytosis and reduced microglial function.

As detailed in the Examples section below, antibodies have been generated that specifically bind to human TREM2 and that modulate one or more downstream functions of the TREM2/DAP12 signaling complex. In certain embodiments, the antibodies further comprise an Fc polypeptide containing mutations that permit binding of the Fc polypeptide to a transferrin receptor (TfR from, e.g., a human). In some aspects, the antibodies disclosed herein are able to bind, through the modified Fc polypeptide, to a transferrin receptor protein (e.g., expressed on the surface of a brain endothelial cell (BECs)) and can thereby cross the blood-brain barrier (BBB) more effectively than antibodies lacking the TfR-binding Fc mutations. In certain embodiments, the antibodies disclosed herein comprise mutations in an Fc polypeptide that reduce or eliminate effector function and mutations that increase in vivo half-life, e.g., by increasing binding of antibody Fc to Fc neonatal receptor (FcRn).

In some embodiments, the anti-TREM2 antibodies enhance TREM2 activity, e.g., enhance phagocytosis or enhance the differentiation, function, migration, or survival of myeloid cells, microglia, or macrophages. Thus, in another aspect, methods of enhancing TREM2 activity, e.g., in a subject having a neurodegenerative disease, are provided.

In some embodiments, the anti-TREM2 antibodies reduce shedding of sTREM2. Thus, in another aspect, methods of decreasing levels of sTREM2, e.g., in a subject having a neurodegenerative disease, are provided.

II. Definitions

As used herein, the singular forms "a," "an" and "the" include plural referents unless the content clearly dictates otherwise. Thus, for example, reference to "an antibody" optionally includes a combination of two or more such molecules, and the like.

As used herein, the terms "about" and "approximately," when used to modify an amount specified in a numeric value or range, indicate that the numeric value as well as reasonable deviations from the value known to the skilled person in the art, for example ±20%, ±10%, or ±5%, are within the intended meaning of the recited value.

As used herein, the term "TREM2 protein" refers to a triggering receptor expressed on myeloid cells 2 protein that is encoded by the gene TREM2. As used herein, a "TREM2 protein" refers to a native (i.e., wild-type) TREM2 protein of any vertebrate, such as but not limited to human, non-human primates (e.g., cynomolgus monkey), rodents (e.g., mice, rat), and other mammals. In some embodiments, a TREM2 protein is a human TREM2 protein having the sequence identified in UniprotKB accession number Q9NZC2 (SEQ ID NO:1).

As used herein, the term "anti-TREM2 antibody" refers to an antibody that specifically binds to a TREM2 protein (e.g., human TREM2).

As used herein, the term "antibody" refers to a protein with an immunoglobulin fold that specifically binds to an antigen via its variable regions. The term encompasses intact polyclonal antibodies, intact monoclonal antibodies, single chain antibodies, multispecific antibodies such as bispecific antibodies, monospecific antibodies, monovalent antibodies, chimeric antibodies, humanized antibodies, and human antibodies. The term "antibody," as used herein, also includes antibody fragments that retain binding specificity via its variable regions, including but not limited to Fab, F(ab')$_2$, Fv, scFv, and bivalent scFv. Antibodies can contain light chains that are classified as either kappa or lambda. Antibodies can contain heavy chains that are classified as gamma, mu, alpha, delta, or epsilon, which in turn define the immunoglobulin classes, IgG, IgM, IgA, IgD and IgE, respectively.

As used herein, the term "anti-TREM2 antigen binding portion" refers to an antigen binding segment or entity that specifically binds to a TREM2 protein (e.g., human TREM2). The terms "antigen-binding portion" and "antigen-binding fragment" are used interchangeably herein and refer to one or more fragments of an antibody that retains the ability to specifically bind to an antigen (e.g., a TREM2 protein) via its variable region. Examples of antigen-binding fragments include, but are not limited to, a Fab fragment (a monovalent fragment consisting of the $V_L$, $V_H$, CL and CH1 domains), F(ab')$_2$ fragment (a bivalent fragment comprising two Fab fragments linked by a disulfide bridge at the hinge region), single chain Fv (scFv), disulfide-linked Fv (dsFv), complementarity determining regions (CDRs), a $V_L$ (light chain variable region), and a $V_H$ (heavy chain variable region).

The term "variable region" or "variable domain" refers to a domain in an antibody heavy chain or light chain that is derived from a germline Variable (V) gene, Diversity (D) gene, or Joining (J) gene (and not derived from a Constant (Cμ and Cδ) gene segment), and that gives an antibody its specificity for binding to an antigen. Typically, an antibody variable region comprises four conserved "framework" regions interspersed with three hypervariable "complementarity determining regions."

The term "complementarity determining region" or "CDR" refers to the three hypervariable regions in each chain that interrupt the four framework regions established by the light and heavy chain variable regions. The CDRs are primarily responsible for antibody binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 or CDR-H3 is located in the variable region of the heavy chain of the antibody in which it is found, whereas a $V_L$ CDR1 or CDR-L1 is the CDR1 from the variable region of the light chain of the antibody in which it is found.

The "framework regions" or "FRs" of different light or heavy chains are relatively conserved within a species. The framework region of an antibody, that is the combined framework regions of the constituent light and heavy chains, serves to position and align the CDRs in three-dimensional space. Framework sequences can be obtained from public DNA databases or published references that include germline antibody gene sequences. For example, germline DNA sequences for human heavy and light chain variable region genes can be found in the "VBASE2" germline variable gene sequence database for human and mouse sequences.

The amino acid sequences of the CDRs and framework regions can be determined using various well-known definitions in the art, e.g., Kabat, Chothia, international ImMunoGeneTics database (IMGT), AbM, and observed antigen contacts ("Contact"). In some embodiments, CDRs are determined according to the Contact definition. See, MacCallum el al., *J. Mol. Biol.*, 262:732-745 (1996). In some embodiments, CDRs are determined by a combination of Kabat, Chothia, and/or Contact CDR definitions.

The term "epitope" refers to the area or region of an antigen to which the CDRs of an antibody specifically binds and can include a few amino acids or portions of a few amino acids, e.g., 5 or 6, or more, e.g., 20 or more amino acids, or portions of those amino acids. For example, where the target is a protein, the epitope can be comprised of consecutive amino acids (e.g., a linear epitope), or amino acids from different parts of the protein that are brought into proximity by protein folding (e.g., a discontinuous or conformational epitope). In some embodiments, the epitope is phosphorylated at one amino acid (e.g., at a serine or threonine residue).

As used herein, the phrase "recognizes an epitope," as used with reference to an anti-TREM2 antibody, means that the antibody CDRs interact with or specifically bind to the antigen (i.e., the TREM2 protein) at that epitope or a portion of the antigen containing that epitope.

A "monoclonal antibody" refers to antibodies produced by a single clone of cells or a single cell line and consisting of or consisting essentially of antibody molecules that are identical in their primary amino acid sequence.

A "polyclonal antibody" refers to an antibody obtained from a heterogeneous population of antibodies in which different antibodies in the population bind to different epitopes of an antigen.

A "chimeric antibody" refers to an antibody molecule in which the constant region, or a portion thereof, is altered, replaced or exchanged so that the antigen-binding site (i.e., variable region, CDR, or portion thereof) is linked to a constant region of a different or altered class, effector function and/or species, or in which the variable region, or a portion thereof, is altered, replaced or exchanged with a variable region having a different or altered antigen specificity (e.g., CDR and framework regions from different species). In some embodiments, a chimeric antibody is a monoclonal antibody comprising a variable region from one source or species (e.g., mouse) and a constant region derived from a second source or species (e.g., human). Methods for producing chimeric antibodies are described in the art.

A "humanized antibody" is a chimeric immunoglobulin derived from a non-human source (e.g., murine) that contains minimal sequences derived from the non-human immunoglobulin outside the CDRs. In general, a humanized antibody will comprise at least one (e.g., two) antigen-binding variable domain(s), in which the CDR regions substantially correspond to those of the non-human immunoglobulin and the framework regions substantially correspond to those of a human immunoglobulin sequence. The humanized antibody can also comprise at least a portion of an immunoglobulin constant region (Fc), typically that of a human immunoglobulin sequence. Methods of antibody humanization are known in the art.

A "human antibody" or a "fully human antibody" is an antibody having human heavy chain and light chain sequences, typically derived from human germline genes. In some embodiments, the antibody is produced by a human cell, by a non-human animal that utilizes human antibody repertoires (e.g., transgenic mice that are genetically engineered to express human antibody sequences), or by phage display platforms.

The term "specifically binds" refers to a molecule (e.g., an antibody or an antigen-binding portion thereof) that binds to an epitope or target with greater affinity, greater avidity, and/or greater duration to that epitope or target in a sample than it binds to another epitope or non-target compound (e.g., a structurally different antigen). In some embodiments, an antibody (or an antigen-binding portion thereof) that specifically binds to an epitope or target is an antibody (or an antigen-binding portion thereof) that binds to the epitope or target with at least 5-fold greater affinity than other epitopes or non-target compounds, e.g., at least 5-fold, 10-fold, 100-fold, 1,000-fold, 10,000-fold, or greater affinity. The term "specific binding," "specifically binds to," or "is specific for" a particular epitope or target, as used herein, can be exhibited, for example, by a molecule having an equilibrium dissociation constant $K_D$ for the epitope or target to which it binds of, e.g., $10^{-4}$ M or smaller, e.g., $10^{-5}$ M, $10^{-6}$ M, $10^{-7}$ M, $10^{-8}$ M, $10^{-9}$ M, $10^{-10}$ M, $10^{-11}$ M, or $10^{-12}$ M. It will be recognized by one of skill that an antibody that specifically binds to a target (e.g., a TREM2 protein) from one species may also specifically bind to orthologs of that target (e.g., the TREM2 protein).

The term "binding affinity" is used herein to refer to the strength of a non-covalent interaction between two molecules, e.g., between an antibody (or an antigen-binding portion thereof) and an antigen. Thus, for example, the term may refer to 1:1 interactions between an antibody (or an antigen-binding portion thereof) and an antigen, unless otherwise indicated or clear from context. Binding affinity may be quantified by measuring an equilibrium dissociation constant ($K_D$), which refers to the dissociation rate constant ($k_d$, time$^{-1}$) divided by the association rate constant ($k_a$, time$^{-1}$ M$^{-1}$). $K_D$ can be determined by measurement of the kinetics of complex formation and dissociation, e.g., using Surface Plasmon Resonance (SPR) methods, e.g., a Biacore™ system; kinetic exclusion assays such as KinExA®; and BioLayer interferometry (e.g., using the ForteBio® Octet platform). As used herein, "binding affinity" includes not only formal binding affinities, such as those reflecting 1:1 interactions between an antibody (or an antigen-binding portion thereof) and an antigen, but also apparent affinities for which $K_D$ values are calculated that may reflect avid binding.

The term "cross-reacts," as used herein, refers to the ability of an antibody to bind to an antigen other than the antigen against which the antibody was raised. In some embodiments, cross-reactivity refers to the ability of an antibody to bind to an antigen from another species than the antigen against which the antibody was raised. As a non-limiting example, an anti-TREM2 antibody as described herein that is raised against a human TREM2 peptide can exhibit cross-reactivity with a TREM2 peptide or protein from a different species (e.g., monkey or mouse).

A "transferrin receptor" or "TfR" as used herein refers to transferrin receptor protein 1. The human transferrin receptor 1 polypeptide sequence is set forth in SEQ ID NO:62. Transferrin receptor protein 1 sequences from other species are also known (e.g., chimpanzee, accession number XP_003310238.1; rhesus monkey, NP_001244232.1; dog, NP_001003111.1; cattle, NP_001193506.1; mouse, NP_035768.1; rat, NP_073203.1; and chicken, NP_990587.1). The term "transferrin receptor" also encompasses allelic variants of exemplary reference sequences, e.g., human sequences, that are encoded by a gene at a transferrin receptor protein 1 chromosomal locus. Full length transferrin receptor protein includes a short N-terminal intracellular region, a transmembrane region, and a large extracellular domain. The extracellular domain is characterized by three domains: a protease-like domain, a helical domain, and an apical domain. The apical domain sequence of human transferrin receptor 1 is set forth in SEQ ID NO:55.

The terms "CH3 domain" and "CH2 domain" as used herein refer to immunoglobulin constant region domain polypeptides. In the context of IgG antibodies, a CH3 domain polypeptide refers to the segment of amino acids from about position 341 to about position 447 as numbered according to the EU numbering scheme, and a CH2 domain polypeptide refers to the segment of amino acids from about position 231 to about position 340 as numbered according to the EU numbering scheme. CH2 and CH3 domain polypeptides may also be numbered by the IMGT (ImMunoGeneTics) numbering scheme in which the CH2 domain numbering is 1-110 and the CH3 domain numbering is 1-107, according to the IMGT Scientific chart numbering (IMGT website). CH2 and CH3 domains are part of the Fc region of an immunoglobulin. In the context of IgG antibodies, an Fc region refers to the segment of amino acids from about position 231 to about position 447 as numbered according to the EU numbering scheme. As used herein, the term "Fc region" may also include at least a part of a hinge region of an antibody. An exemplary partial hinge region sequence is set forth in SEQ ID NO:57.

The terms "corresponding to," "determined with reference to," or "numbered with reference to" when used in the context of the identification of a given amino acid residue in a polypeptide sequence, refers to the position of the residue of a specified reference sequence when the given amino acid sequence is maximally aligned and compared to the reference sequence. Thus, for example, an amino acid residue in a polypeptide "corresponds to" an amino acid in the region of SEQ ID NO:38 from amino acids 111-217 when the residue aligns with the amino acid in SEQ ID NO:38 when optimally aligned to SEQ ID NO:38. The polypeptide that is aligned to the reference sequence need not be the same length as the reference sequence.

As used herein, the term "Fc polypeptide" refers to the C-terminal region of a naturally occurring immunoglobulin heavy chain polypeptide that is characterized by an Ig fold as a structural domain. An Fc polypeptide contains constant region sequences including at least the CH2 domain and/or the CH3 domain and may contain at least part of the hinge region, but does not contain a variable region.

A "modified Fc polypeptide" refers to an Fc polypeptide that has at least one mutation, e.g., a substitution, deletion or insertion, as compared to a wild-type immunoglobulin heavy chain Fc polypeptide sequence, but retains the overall Ig fold or structure of the native Fc polypeptide.

The term "isolated," as used with reference to a nucleic acid or protein (e.g., antibody), denotes that the nucleic acid or protein is essentially free of other cellular components with which it is associated in the natural state. Purity and homogeneity are typically determined using analytical chemistry techniques such as electrophoresis (e.g., polyacrylamide gel electrophoresis) or chromatography (e.g., high performance liquid chromatography). In some embodiments, an isolated nucleic acid or protein (e.g., antibody) is at least 85% pure, at least 90% pure, at least 95% pure, or at least 99% pure.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Naturally occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof. "Amino acid analogs" refer to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The terms "polypeptide" and "peptide" are used interchangeably herein to refer to a polymer of amino acid residues in a single chain. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

The term "protein" as used herein refers to either a polypeptide or a dimer (i.e., two) or multimer (i.e., three or more) of single chain polypeptides. The single chain polypeptides of a protein may be joined by a covalent bond, e.g., a disulfide bond, or non-covalent interactions.

The terms "polynucleotide" and "nucleic acid" interchangeably refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. Examples of polynucleotides contemplated herein include single- and double-stranded DNA, single- and double-stranded RNA, and hybrid molecules having mixtures of single- and double-stranded DNA and RNA.

The terms "conservative substitution" and "conservative mutation" refer to an alteration that results in the substitution of an amino acid with another amino acid that can be categorized as having a similar feature. Examples of categories of conservative amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R), and His (Histidine or H); an "aromatic group" including Phe (Phenylalanine or F), Tyr (Tyrosine or Y), Trp (Tryptophan or W), and (Histidine or H); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T), and Cys (Cysteine or C). Within each group, subgroups can also be identified. For example, the group of charged or polar amino acids can be sub-divided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into sub-groups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr, and Cys. Examples of categories of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH$_2$ can be maintained. In some embodiments, hydrophobic amino acids are substituted for naturally occurring hydrophobic amino acid, e.g., in the active site, to preserve hydrophobicity.

The terms "identical" or percent "identity," in the context of two or more polypeptide sequences, refer to two or more sequences or subsequences that are the same or have a specified percentage of amino acid residues, e.g., at least 60%, at least 65%, at least 70%, at least 75%, at least 80%, at least 85%, at least 90%, or at least 95% or greater, that are identical over a specified region when compared and aligned for maximum correspondence over a comparison window, or designated region as measured using a sequence comparison algorithm or by manual alignment and visual inspection.

For sequence comparison of polypeptides, typically one amino acid sequence acts as a reference sequence, to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 (Genentech, South San Francisco, Calif.) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

The terms "subject," "individual," and "patient," as used interchangeably herein, refer to a mammal, including but not limited to humans, non-human primates, rodents (e.g., rats, mice, and guinea pigs), rabbits, cows, pigs, horses, and other mammalian species. In one embodiment, the subject, individual, or patient is a human.

The terms "treating," "treatment," and the like are used herein to generally mean obtaining a desired pharmacologic and/or physiologic effect. "Treating" or "treatment" may refer to any indicia of success in the treatment or amelioration of a neurodegenerative disease (e.g., Alzheimer's disease or another neurodegenerative disease described herein), including any objective or subjective parameter such as abatement, remission, improvement in patient survival, increase in survival time or rate, diminishing of symptoms or making the disease more tolerable to the patient, slowing in the rate of degeneration or decline, or improving a patient's physical or mental well-being. The treatment or amelioration of symptoms can be based on objective or subjective parameters. The effect of treatment can be compared to an individual or pool of individuals not receiving the treatment, or to the same patient prior to treatment or at a different time during treatment.

The term "pharmaceutically acceptable excipient" refers to a non-active pharmaceutical ingredient that is biologically or pharmacologically compatible for use in humans or animals, such as, but not limited to a buffer, carrier, or preservative.

As used herein, a "therapeutic amount" or "therapeutically effective amount" of an agent (e.g., an antibody as described herein) is an amount of the agent that treats, alleviates, abates, or reduces the severity of symptoms of a disease in a subject. A "therapeutic amount" of an agent (e.g., an antibody as described herein) may improve patient survival, increase survival time or rate, diminish symptoms, make an injury, disease, or condition (e.g., a neurodegenerative disease) more tolerable, slow the rate of degeneration or decline, or improve a patient's physical or mental well-being.

The term "administer" refers to a method of delivering agents, compounds, or compositions to the desired site of biological action. These methods include, but are not limited to, topical delivery, parenteral delivery, intravenous delivery, intradermal delivery, intramuscular delivery, intrathecal delivery, colonic delivery, rectal delivery, or intraperitoneal delivery. In one embodiment, an antibody as described herein is administered intravenously.

The term "control" or "control value" refers to a reference value or baseline value. Appropriate controls can be determined by one skilled in the art. In some instances, control values can be determined relative to a baseline within the same subject or experiment, e.g., a measurement of sTREM2 taken prior to treatment with an anti-TREM2 antibody can be a control value for a post-treatment measurement of sTREM2 levels in the same subject. In other instances, the control value can be determined relative to a control subject (e.g., a healthy control or a disease control) or an average value in a population of control subjects (e.g., healthy controls or disease controls, e.g., a population of 10, 20, 50, 100, 200, 500, 1000 control subjects or more), e.g., a measurement of a subject's level of sTREM2 either at baseline or after treatment can be compared to a healthy control value.

III. Anti-TREM2 Antibodies

In one aspect, antibodies that specifically bind to a TREM2 protein are provided. In some embodiments, the antibody specifically binds to a human TREM2 protein. In some embodiments, an anti-TREM2 antibody is selective for TREM2 over other TREM-like receptors (e.g., TREM1).

In some embodiments, an anti-TREM2 antibody is an antibody that comprises one or more complementarity determining region (CDR), heavy chain variable region, and/or light chain variable region sequences as disclosed herein. In some embodiments, an anti-TREM2 antibody comprises one or more CDR, heavy chain variable region, and/or light chain variable region sequences as disclosed herein and further comprises one or more functional characteristics as disclosed herein, e.g., an antibody that enhances TREM2 activity (e.g., enhances phagocytosis, or enhances the migration, differentiation, function, or survival of a cell such as a myeloid cell, microglia, or macrophage) or an antibody that decreases levels of sTREM2. In some embodiments, the anti-TREM2 antibody comprises Fc polypeptides that comprise one or more modifications as described herein.

In some embodiments, the anti-TREM2 antibody is a chimeric antibody. In some embodiments, the anti-TREM2 antibody is a humanized and/or affinity matured antibody.

Anti-TREM2 Sequences

In some embodiments, a heavy chain sequence, or a portion thereof, and/or a light chain sequence, or a portion thereof, is derived from an anti-TREM2 antibody described herein (e.g., Clone CL0020306, Clone CL0020188, or Clone CL0020307). The CDR, heavy chain variable region, and light chain variable region amino acid sequences of these clones is set forth in Table 8.

In some embodiments, an anti-TREM2 antibody comprises one or more CDRs selected from the group consisting of:
 (a) a heavy chain CDR1 (CDR-H1) sequence having at least 90% sequence identity to the amino acid sequence of any one of SEQ ID NOS:4 and 12, or having up to two amino acid substitutions relative to the amino acid sequence of any one of SEQ ID NOS:4 and 12;
 (b) a heavy chain CDR2 (CDR-H2) sequence having at least 90% sequence identity to the amino acid sequence of any one of SEQ ID NOS:5, 13, and 25, or having up to two amino acid substitutions relative to the amino acid sequence of any one of SEQ ID NOS:5, 13, and 25;
 (c) a heavy chain CDR3 (CDR-H3) sequence having at least 90% sequence identity to the amino acid sequence of any one of SEQ ID NOS:6, 14, and 17, or having up to two amino acid substitutions relative to the amino acid sequence of any one of SEQ ID NOS:6, 14, and 17;

(d) a light chain CDR1 (CDR-L1) sequence having at least 90% sequence identity to the amino acid sequence of any one of SEQ ID NOS:7 and 23, or having up to two amino acid substitutions relative to the amino acid sequence of any one of SEQ ID NOS:7 and 23;

(e) a light chain CDR2 (CDR-L2) sequence having at least 90% sequence identity to the amino acid sequence of SEQ ID NO:8, or having up to two amino acid substitutions relative to the amino acid sequence of SEQ ID NO:8; and (f) a light chain CDR3 (CDR-L3) sequence having at least 90% sequence identity to the amino acid sequence of any one of SEQ ID NOS:9 and 18, or having up to two amino acid substitutions relative to the amino acid sequence of any one of SEQ ID NOS:9 and 18.

In some embodiments, an anti-TREM2 antibody comprises two, three, four, five, or all six of (a)-(f). In some embodiments, an anti-TREM2 antibody comprises the CDR-H1 of (a), the CDR-H2 of (b), and the CDR-H3 of (c). In some embodiments, an anti-TREM2 antibody comprises the CDR-L1 of (d), the CDR-L2 of (e), and the CDR-L3 of (f). In some embodiments, a CDR having up to two amino acid substitutions has one amino acid substitution relative to the reference sequence. In some embodiments, a CDR having up to two amino acid substitutions has two amino acid substitutions relative to the reference sequence. In some embodiments, the up to two amino acid substitutions are conservative substitutions.

In some embodiments, an anti-TREM2 antibody comprises one or more CDRs selected from the group consisting of:

(a) a CDR-H1 sequence comprising the amino acid sequence of any one of SEQ ID NOS:4 and 12;

(b) a CDR-H2 sequence comprising the amino acid sequence of any one of SEQ ID NOS:5, 13, and 25;

(c) a CDR-H3 sequence comprising the amino acid sequence of any one of SEQ ID NOS:6, 14, and 17;

(d) a CDR-L1 sequence comprising the amino acid sequence of any one of SEQ ID NOS:7 and 23;

(e) a CDR-L2 sequence comprising the amino acid sequence of SEQ ID NO:8; and (f) a CDR-L3 sequence comprising the amino acid sequence of any one of SEQ ID NOS:9 and 18.

In some embodiments, an anti-TREM2 antibody comprises two, three, four, five, or all six of (a)-(f). In some embodiments, an anti-TREM2 antibody comprises the CDR-H1 of (a), the CDR-H2 of (b), and the CDR-H3 of (c). In some embodiments, an anti-TREM2 antibody comprises the CDR-L1 of (d), the CDR-L2 of (e), and the CDR-L3 of (f).

In some embodiments, an anti-TREM2 antibody comprises:

(a) a CDR-H1 comprising the amino acid sequence of SEQ ID NO:4, a CDR-H2 comprising the amino acid sequence of SEQ ID NO:5, a CDR-H3 comprising the amino acid sequence of SEQ ID NO: 17, a CDR-L1 comprising the amino acid sequence of SEQ ID NO:7, a CDR-L2 comprising the amino acid sequence of SEQ ID NO:8, and a CDR-L3 comprising the amino acid sequence of SEQ ID NO: 18; or (b) a CDR-H1 comprising the amino acid sequence of SEQ ID NON, a CDR-H2 comprising the amino acid sequence of SEQ ID NO:5, a CDR-H3 comprising the amino acid sequence of SEQ ID NO: 17, a CDR-L1 comprising the amino acid sequence of SEQ ID NO:23, a CDR-L2 comprising the amino acid sequence of SEQ ID NO:8, and a CDR-L3 comprising the amino acid sequence of SEQ ID NO: 18; or (c) a CDR-H1 comprising the amino acid sequence of SEQ ID NON, a CDR-H2 comprising the amino acid sequence of SEQ ID NO:25, a CDR-H3 comprising the amino acid sequence of SEQ ID NO: 17, a CDR-L1 comprising the amino acid sequence of SEQ ID NON, a CDR-L2 comprising the amino acid sequence of SEQ ID NO:8, and a CDR-L3 comprising the amino acid sequence of SEQ ID NO: 18; or (d) a CDR-H1 comprising the amino acid sequence of SEQ ID NON, a CDR-H2 comprising the amino acid sequence of SEQ ID NO:25, a CDR-H3 comprising the amino acid sequence of SEQ ID NO: 17, a CDR-L1 comprising the amino acid sequence of SEQ ID NO:23, a CDR-L2 comprising the amino acid sequence of SEQ ID NO:8, and a CDR-L3 comprising the amino acid sequence of SEQ ID NO: 18; or (e) a CDR-H1 comprising the amino acid sequence of SEQ ID NON, a CDR-H2 comprising the amino acid sequence of SEQ ID NON, a CDR-H3 comprising the amino acid sequence of SEQ ID NON, a CDR-L1 comprising the amino acid sequence of SEQ ID NON, a CDR-L2 comprising the amino acid sequence of SEQ ID NO:8, and a CDR-L3 comprising the amino acid sequence of SEQ ID NON; or (f) a CDR-H1 comprising the amino acid sequence of SEQ ID NO: 12, a CDR-H2 comprising the amino acid sequence of SEQ ID NO: 13, a CDR-H3 comprising the amino acid sequence of SEQ ID NO: 14, a CDR-L1 comprising the amino acid sequence of SEQ ID NON, a CDR-L2 comprising the amino acid sequence of SEQ ID NO:8, and a CDR-L3 comprising the amino acid sequence of SEQ ID NON; or (g) a CDR-H1 comprising the amino acid sequence of SEQ ID NON, a CDR-H2 comprising the amino acid sequence of SEQ ID NO:25, a CDR-H3 comprising the amino acid sequence of SEQ ID NO: 17, a CDR-L1 comprising the amino acid sequence of SEQ ID NON, a CDR-L2 comprising the amino acid sequence of SEQ ID NO:8, and a CDR-L3 comprising the amino acid sequence of SEQ ID NON.

In some embodiments, an anti-TREM2 antibody comprises a heavy chain variable region comprising an amino acid sequence that has at least 85%, 90%, 91%, 92%, 93%, 94%, 95%, 96%, 97%, 98%, or 99% sequence identity to any one of SEQ ID NOS:2, 10, 15, 19, 21, 24, and 26. In some embodiments, an anti-TREM2 comprises a heavy chain variable region comprising the amino acid sequence of any one of SEQ ID NOS:2, 10, 15, 19, 21, 24, and 26.

In some embodiments, an anti-TREM2 antibody comprises a light chain variable region comprising an amino acid sequence that has at least 85%, 90%, 91%, 92%, 93%, 94%, 95%, 96%, 97%, 98%, or 99% sequence identity to any one of SEQ ID NOS:3, 11, 16, 20, 22, and 27. In some embodiments, an anti-TREM2 antibody comprises a light chain variable region comprising the amino acid sequence of any one of SEQ ID NOS:3, 11, 16, 20, 22, and 27.

In some embodiments, an anti-TREM2 antibody comprises: a heavy chain variable region comprising an amino acid sequence that has at least 85%, 90%, 91%, 92%, 93%, 94%, 95%, 96%, 97%, 98%, or 99% sequence identity to any one of SEQ ID NOS:2, 10, 15, 19, 21, 24, and 26, a light chain variable region comprising an amino acid sequence that has at least 85%, 90%, 91%, 92%, 93%, 94%, 95%, 96%, 97%, 98%, or 99% sequence identity to any one of SEQ ID NOS:3, 11, 16, 20, 22, and 27. In some embodiments, an anti-TREM2 comprises: a heavy chain variable region comprising the amino acid sequence of any one of SEQ ID NOS:2, 10, 15, 19, 21, 24, and 26, and a light chain variable region comprising the amino acid sequence of any one of SEQ ID NOS:3, 11, 16, 20, 22, and 27.

In some embodiments, an anti-TREM2 antibody comprises:
(a) a $V_H$ sequence that has at least 85% sequence identity to SEQ ID NO:2 and a $V_L$ sequence has at least 85% sequence identity to SEQ ID NO:3; or
(b) a $V_H$ sequence that has at least 85% sequence identity to SEQ ID NO: 10 and a $V_L$ sequence has at least 85% sequence identity to SEQ ID NO: 11; or
(c) a $V_H$ sequence that has at least 85% sequence identity to SEQ ID NO: 15 and a $V_L$ sequence has at least 85% sequence identity to SEQ ID NO: 16; or
(d) a $V_H$ sequence that has at least 85% sequence identity to SEQ ID NO: 19 and a $V_L$ sequence has at least 85% sequence identity to SEQ ID NO:20; or
(e) a $V_H$ sequence that has at least 85% sequence identity to SEQ ID NO:21 and a $V_L$ sequence has at least 85% sequence identity to SEQ ID NO:20; or
(f) a $V_H$ sequence that has at least 85% sequence identity to SEQ ID NO: 19 and a $V_L$ sequence has at least 85% sequence identity to SEQ ID NO:22; or
(g) a $V_H$ sequence that has at least 85% sequence identity to SEQ ID NO:21 and a $V_L$ sequence has at least 85% sequence identity to SEQ ID NO:22; or
(h) a $V_H$ sequence that has at least 85% sequence identity to SEQ ID NO:24 and a $V_L$ sequence has at least 85% sequence identity to SEQ ID NO:20; or (i) a $V_H$ sequence that has at least 85% sequence identity to SEQ ID NO:26 and a $V_L$ sequence has at least 85% sequence identity to SEQ ID NO:20; or (j) a $V_H$ sequence that has at least 85% sequence identity to SEQ ID NO:24 and a $V_L$ sequence has at least 85% sequence identity to SEQ ID NO:22; or (k) a $V_H$ sequence that has at least 85% sequence identity to SEQ ID NO:26 and a $V_L$ sequence has at least 85% sequence identity to SEQ ID NO:22; or (l) a $V_H$ sequence that has at least 85% sequence identity to SEQ ID NO:24 and a $V_L$ sequence has at least 85% sequence identity to SEQ ID NO:27.

In some embodiments, an anti-TREM2 antibody comprises one or more sequences that are encompassed by a consensus sequence disclosed herein. As a non-limiting example, consensus sequences can be identified by aligning heavy chain or light chain sequences (e.g., CDRs) for antibodies that are from the same (or similar) germlines. In some embodiments, consensus sequences may be generated from antibodies that contain sequences that are of the same (or similar) length and/or have at least one highly similar CDR (e.g., a highly similar CDR3). In some embodiments, such sequences in these antibodies may be aligned and compared to identify conserved amino acids or motifs (i.e., where alteration in sequences may alter protein function) and/or regions where variation occurs the sequences (i.e., where variation of sequence is not likely to significantly affect protein function). Alternatively, consensus sequences can be identified by aligning heavy chain or light chain sequences (e.g., CDRs) for antibodies that bind to the same or similar (e.g., overlapping) epitopes to determine conserved amino acids or motifs (i.e., where alteration in sequences may alter protein function) and regions where variation occurs in alignment of sequences (i.e., where variation of sequence is not likely to significantly affect protein function). In some embodiments, one or more consensus sequences can be identified for antibodies that recognize the same or similar epitope as an anti-TREM2 antibody as disclosed herein. Exemplary consensus sequences include SEQ ID NOS:28-32. In the consensus sequences of SEQ ID NOS:28-32, the capitalized letter represents an amino acid residue that is absolutely conserved among the aligned sequences (e.g., aligned CDR sequences), while an "X" or a Greek letter (e.g., "α," "β," "γ," "δ," "ε," or "φ") represents an amino acid residue that is not absolutely conserved among the aligned sequences. It will be appreciated that, when selecting an amino acid to insert at a position marked by an "X" or by a Greek letter, in some embodiments the amino acid is selected from those amino acids found at the corresponding position in the aligned sequences.

Clones CL0020188, CL0020306, CL0020307, and variants of CL0020188

In some embodiments, an anti-TREM2 antibody comprises:
(a) a CDR-H1 sequence comprising the sequence of G-F-T-F-T-$α_6$-F-Y-M-S (SEQ ID NO:28), wherein $α_6$ is D or N;
(b) a CDR-H2 sequence comprising the sequence of V-I-R-N-$β_5$-$β_6$-N-$β_8$-Y-T-$β_{11}$-$β_{12}$-Y-N-P-S-V-K-G (SEQ ID NO:29), wherein $β_5$ is K or R; $β_6$ is A or P; $β_8$ is G or A; $β_{11}$ is A or T; and $β_{12}$ is G or D;
(c) a CDR-H3 sequence comprising the sequence of $γ_1$-R-L-$γ_4$-Y-G-F-D-Y (SEQ ID NO:30), wherein $γ_1$ is A or T; and $γ_4$ is T or S;
(d) a CDR-L1 sequence comprising the sequence of Q-S-S-K-S-L-L-H-S-$δ_{10}$-G-K-T-Y-L-N(SEQ ID NO:31), wherein $δ_{10}$ is N or T;
(e) a CDR-L2 sequence comprising the sequence of WMSTRAS (SEQ ID NO:8); and
(f) a CDR-L3 sequence comprising the sequence of Q-Q-F-L-E-$φ_6$-P-F-T (SEQ ID NO:32), wherein $φ_6$ is Y or F.

In some embodiments, an anti-TREM2 antibody comprises a CDR-H1 sequence that is selected from SEQ ID NOS:4 and 12. In some embodiments, an anti-TREM2 antibody comprises a CDR-H2 sequence that is selected from SEQ ID NOS:5, 13, and 25. In some embodiments, an anti-TREM2 antibody comprises a CDR-H3 sequence that is selected from SEQ ID NOS:6, 14, and 17. In some embodiments, an anti-TREM2 antibody comprises a CDR-L1 sequence that is selected from SEQ ID NOS:7 and 23. In some embodiments, an anti-TREM2 antibody comprises a CDR-L3 sequence is selected from SEQ ID NOS:9 and 18.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:2, 10, 15, 19, 21, 24, and 26. In some embodiments, an anti-TREM2 antibody comprises a heavy chain variable region comprising the amino acid sequence of any one of SEQ ID NOS:2, 10, 15, 19, 21, 24, and 26.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to any one of SEQ ID NOS:3, 11, 16, 20, 22, and 27. In some embodiments, an anti-TREM2 antibody comprises a light chain variable region comprising the amino acid sequence of any one of SEQ ID NOS:3, 11, 16, 20, 22, and 27.

Clone CL0020188

In some embodiments, an anti-TREM2 antibody comprises a CDR-H1 sequence comprising the amino acid sequence of SEQ ID NON, a CDR-H2 sequence comprising the amino acid sequence of SEQ ID NO:5, a CDR-H3 sequence comprising the amino acid sequence of SEQ ID NO: 17, a CDR-L1 sequence comprising the amino acid sequence of SEQ ID NO:7, a CDR-L2 sequence comprising the amino acid sequence of SEQ ID NO:8, and a CDR-L3 sequence comprising the amino acid sequence of SEQ ID NO: 18.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO: 15. In some embodiments, an anti-TREM2 antibody comprises a heavy chain variable region comprising the amino acid sequence of SEQ ID NO: 15.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO: 16. In some embodiments, an anti-TREM2 antibody comprises a light chain variable region comprising the amino acid sequence of SEQ ID NO: 16.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO: 15 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO: 16. In some embodiments, an anti-TREM2 antibody comprises a heavy chain variable region comprising the amino acid sequence of SEQ ID NO: 15 and a light chain variable region comprising the amino acid sequence of SEQ ID NO: 16.

In some embodiments, an anti-TREM2 antibody comprises a heavy chain variable region that comprises a heavy chain CDR1-3 comprising the amino acid sequences of SEQ ID NOS:4, 5, and 17, respectively, and that has at least 85% sequence identity (e.g., at least 90%, 91%, 92%, 93%, 94%, 95%, 96%, 97%, 98%, or 99% sequence identity) to SEQ ID NO: 15. In some embodiments, an anti-TREM2 antibody comprises a light chain variable region that comprises a light chain CDR1-3 comprising the amino acid sequences of SEQ ID NOS:7, 8, and 18, respectively, and that has at least 85% sequence identity (e.g., at least 90%, 91%, 92%, 93%, 94%, 95%, 96%, 97%, 98%, or 99% sequence identity) to SEQ ID NO: 16.

In some embodiments, an anti-TREM2 antibody competes for binding with an antibody as described herein (e.g., an antibody comprising a heavy chain CDR1-3 and a light chain CDR1-3 comprising the amino acid sequences of SEQ ID NOS:4, 5, 17, 7, 8, and 18, respectively, or an antibody comprising a heavy chain variable region comprising the amino acid sequence of SEQ ID NO: 15 and a light chain variable region comprising the amino acid sequence of SEQ ID NO: 16).

In some embodiments, an anti-TREM2 antibody comprises a CDR-H1 sequence comprising the amino acid sequence of SEQ ID NON, a CDR-H2 sequence comprising the amino acid sequence of SEQ ID NO:25, a CDR-H3 sequence comprising the amino acid sequence of SEQ ID NO: 17, a CDR-L1 sequence comprising the amino acid sequence of SEQ ID NO:23, a CDR-L2 sequence comprising the amino acid sequence of SEQ ID NO:8, and a CDR-L3 sequence comprising the amino acid sequence of SEQ ID NO: 18.

In some embodiments, an anti-TREM2 antibody or antigen binding portion comprises a heavy chain variable region comprising an amino acid sequence that has at least 85% sequence identity (e.g., at least 90%, 95%, or 97% sequence identity) to SEQ ID NO:24. In some embodiments, an anti-TREM2 antibody or antigen binding portion comprises a heavy chain variable region comprising the amino acid sequence of SEQ ID NO:24.

In some embodiments, an anti-TREM2 antibody or antigen binding portion comprises a light chain variable region comprising an amino acid sequence that has at least 85% sequence identity (e.g., at least 90%, 95%, or 97% sequence identity) to SEQ ID NO:22. In some embodiments, an anti-TREM2 antibody or antigen binding portion comprises a light chain variable region comprising the amino acid sequence of SEQ ID NO:22.

In some embodiments, an anti-TREM2 antibody or antigen binding portion comprises a heavy chain variable region comprising an amino acid sequence that has at least 85% sequence identity (e.g., at least 90%, 95%, or 97% sequence identity) to SEQ ID NO:24 and a light chain variable region comprising an amino acid sequence that has at least 85% sequence identity (e.g., at least 90%, 95%, or 97% sequence identity) to SEQ ID NO:22. In some embodiments, an anti-TREM2 antibody or antigen binding portion comprises a heavy chain variable region comprising the amino acid sequence of SEQ ID NO:24 and a light chain variable region comprising the amino acid sequence of SEQ ID NO:22.

In some embodiments, an anti-TREM2 antibody or antigen binding portion comprises a heavy chain variable region that comprises a heavy chain CDK1-3 comprising the amino acid sequences of SEQ ID NOS:4, 25, and 17, respectively, and that has at least 85% sequence identity (e.g., at least 90%, 95%, or 97% sequence identity) to SEQ ID NO:24. In some embodiments, an anti-TREM2 antibody or antigen binding portion comprises a light chain variable region that comprises a light chain CDR1-3 comprising the amino acid sequences of SEQ ID NOS:23, 8, and 18, respectively, and that has at least 85% sequence identity (e.g., at least 90%, 95%, or 97% sequence identity) to SEQ ID NO:22.

In some embodiments, an anti-TREM2 antibody or antigen binding portion competes for binding with an antibody as described herein (e.g., an antibody comprising a heavy chain CDR1-3 and a light chain CDR1-3 comprising the amino acid sequences of SEQ ID NOS:4, 25, 17, 23, 8, and 18, respectively, or an antibody comprising a heavy chain variable region comprising the amino acid sequence of SEQ ID NO:24 and a light chain variable region comprising the amino acid sequence of SEQ ID NO:22).

In some embodiments, an anti-TREM2 antibody or antigen binding portion comprises a CDR-H1 sequence comprising the amino acid sequence of SEQ ID NO:4, a CDR-H2 sequence comprising the amino acid sequence of SEQ ID NO:25, a CDR-H3 sequence comprising the amino acid sequence of SEQ ID NO: 17, a CDR-L1 sequence comprising the amino acid sequence of SEQ ID NO:7, a CDR-L2 sequence comprising the amino acid sequence of SEQ ID NO:8, and a CDR-L3 sequence comprising the amino acid sequence of SEQ ID NO:9.

In some embodiments, an anti-TREM2 antibody or antigen binding portion comprises a heavy chain variable region comprising an amino acid sequence that has at least 85% sequence identity (e.g., at least 90%, 95%, or 97% sequence identity) to SEQ ID NO:24. In some embodiments, an anti-TREM2 antibody or antigen binding portion comprises a heavy chain variable region comprising the amino acid sequence of SEQ ID NO:24.

In some embodiments, an anti-TREM2 antibody or antigen binding portion comprises a light chain variable region comprising an amino acid sequence that has at least 85% sequence identity (e.g., at least 90%, 95%, or 97% sequence identity) to SEQ ID NO:27. In some embodiments, an anti-TREM2 antibody or antigen binding portion comprises a light chain variable region comprising the amino acid sequence of SEQ ID NO:27.

In some embodiments, an anti-TREM2 antibody or antigen binding portion comprises a heavy chain variable region comprising an amino acid sequence that has at least 85% sequence identity (e.g., at least 90%, 95%, or 97% sequence identity) to SEQ ID NO:24 and a light chain variable region comprising an amino acid sequence that has at least 85% sequence identity (e.g., at least 90%, 95%, or 97% sequence identity) to SEQ ID NO:27. In some embodiments, an anti-TREM2 antibody or antigen binding portion comprises a heavy chain variable region comprising the amino acid sequence of SEQ ID NO:24 and a light chain variable region comprising the amino acid sequence of SEQ ID NO:27.

In some embodiments, an anti-TREM2 antibody or antigen binding portion comprises a heavy chain variable region that comprises a heavy chain CDR1-3 comprising the amino acid sequences of SEQ ID NOS:4, 25, and 17, respectively, and that has at least 85% sequence identity (e.g., at least 90%, 95%, or 97% sequence identity) to SEQ ID NO:24. In some embodiments, an anti-TREM2 antibody or antigen binding portion comprises a light chain variable region that comprises a light chain CDR1-3 comprising the amino acid sequences of SEQ ID NOS:7, 8, and 9, respectively, and that has at least 85% sequence identity (e.g., at least 90%, 95%, or 97% sequence identity) to SEQ ID NO:27.

In some embodiments, an anti-TREM2 antibody or antigen binding portion is an antibody that competes for binding with an antibody as described herein (e.g., an antibody comprising a heavy chain CDR1-3 and a light chain CDR1-3 comprising the amino acid sequences of SEQ ID NOS:4, 25, 17, 7, 8, and 9, respectively, or an antibody comprising a heavy chain variable region comprising the amino acid sequence of SEQ ID NO:24 and a light chain variable region comprising the amino acid sequence of SEQ ID NO:27).

Clone CL0020306

In some embodiments, an anti-TREM2 antibody comprises a CDR-H1 sequence comprising the amino acid sequence of SEQ ID NO:4, a CDR-H2 sequence comprising the amino acid sequence of SEQ ID NO:5, a CDR-H3 sequence comprising the amino acid sequence of SEQ ID NO:6, a CDR-L1 sequence comprising the amino acid sequence of SEQ ID NO:7, a CDR-L2 sequence comprising the amino acid sequence of SEQ ID NO:8, and a CDR-L3 sequence comprising the amino acid sequence of SEQ ID NO:9.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:2. In some embodiments, an anti-TREM2 antibody comprises a heavy chain variable region comprising the amino acid sequence of SEQ ID NO:2.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:3. In some embodiments, an anti-TREM2 antibody comprises a light chain variable region comprising the amino acid sequence of SEQ ID NO:3.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:2 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO:3. In some embodiments, an anti-TREM2 antibody comprises a heavy chain variable region comprising the amino acid sequence of SEQ ID NO:2 and a light chain variable region comprising the amino acid sequence of SEQ ID NO:3.

In some embodiments, an anti-TREM2 antibody comprises a heavy chain variable region that comprises a heavy chain CDR1-3 comprising the amino acid sequences of SEQ ID NOS:4, 5, and 6, respectively, and that has at least 85% sequence identity (e.g., at least 90%, 91%, 92%, 93%, 94%, 95%, 96%, 97%, 98%, or 99% sequence identity) to SEQ ID NO:2. In some embodiments, an anti-TREM2 antibody comprises a light chain variable region that comprises a light chain CDR1-3 comprising the amino acid sequences of SEQ ID NOS:7, 8, and 9, respectively, and that has at least 85% sequence identity (e.g., at least 90%, 91%, 92%, 93%, 94%, 95%, 96%, 97%, 98%, or 99% sequence identity) to SEQ ID NO:3.

In some embodiments, an anti-TREM2 antibody competes for binding with an antibody as described herein (e.g., an antibody comprising a heavy chain CDR1-3 and a light chain CDR1-3 comprising the amino acid sequences of SEQ ID NOS:4, 5, 6, 7, 8, and 9, respectively, or an antibody comprising a heavy chain variable region comprising the amino acid sequence of SEQ ID NO:2 and a light chain variable region comprising the amino acid sequence of SEQ ID NO:3).

Clone CL0020307

In some embodiments, an anti-TREM2 antibody comprises a CDR-H1 sequence comprising the amino acid sequence of SEQ ID NO: 12, a CDR-H2 sequence comprising the amino acid sequence of SEQ ID NO: 13, a CDR-H3 sequence comprising the amino acid sequence of SEQ ID NO: 14, a CDR-L1 sequence comprising the amino acid sequence of SEQ ID NO:7, a CDR-L2 sequence comprising the amino acid sequence of SEQ ID NO:8, and a CDR-L3 sequence comprising the amino acid sequence of SEQ ID NO:9.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO: 10. In some embodiments, an anti-TREM2 antibody or antigen binding portion comprises a heavy chain variable region comprising the amino acid sequence of SEQ ID NO:10.

In some embodiments, an anti-TREM2 antibody comprises a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO: 11. In some embodiments, an anti-TREM2 antibody comprises a light chain variable region comprising the amino acid sequence of SEQ ID NO: 11.

In some embodiments, an anti-TREM2 antibody comprises a heavy chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO: 10 and a light chain variable region comprising an amino acid sequence that has at least 85% sequence identity (e.g., at least 90%, 91%, 92%, 93%, 94%, 95%, 96%, 97%, 98%, or 99% sequence identity) to SEQ ID NO: 11. In some embodiments, an anti-TREM2 antibody comprises a heavy chain variable region comprising the amino acid sequence of SEQ ID NO: 10 and a light chain variable region comprising the amino acid sequence of SEQ ID NO: 11.

In some embodiments, an anti-TREM2 antibody comprises a heavy chain variable region that comprises a heavy chain CDR1-3 comprising the amino acid sequences of SEQ ID NOS: 12, 13, and 14, respectively, and that has at least 85% sequence identity (e.g., at least 90%, 91%, 92%, 93%, 94%, 95%, 96%, 97%, 98%, or 99% sequence identity) to SEQ ID NO: 10. In some embodiments, an anti-TREM2 antibody comprises a light chain variable region that comprises a light chain CDR1-3 comprising the amino acid sequences of SEQ ID NOS:7, 8, and 9, respectively, and that has at least 85% sequence identity (e.g., at least 90%, 91%, 92%, 93%, 94%, 95%, 96%, 97%, 98%, or 99% sequence identity) to SEQ ID NO: 11.

In some embodiments, an anti-TREM2 antibody is an antibody that competes for binding with an antibody as described herein (e.g., an antibody comprising a heavy chain CDR1-3 and a light chain CDR1-3 comprising the amino acid sequences of SEQ ID NOS: 12, 13, 14, 7, 8, and 9, respectively, or an antibody comprising a heavy chain variable region comprising the amino acid sequence of SEQ ID NO: 10 and a light chain variable region comprising the amino acid sequence of SEQ ID NO: 11).

Binding Characteristics of Anti-TREM2 Antibodies

In some embodiments, an antibody as described herein that specifically binds to a TREM2 protein binds to TREM2 that is expressed on a cell (e.g., a primary cell or cell line that endogenously expresses TREM2, such as human macrophages, or a primary cell or cell line that has been engineered to express TREM2, e.g., as described in the Examples section below). In some embodiments, an antibody that specifically binds to a TREM2 protein as described herein binds to purified or recombinant TREM2 protein of a portion thereof, or to a chimeric protein comprising TREM2 or a portion thereof (e.g., an Fc-fusion protein comprising TREM2 or an Fc-fusion protein comprising the ecto-domain of TREM2).

In some embodiments, some embodiments, an antibody that specifically binds to human TREM2 protein exhibits cross-reactivity with one or more other TREM2 proteins of another species. In some embodiments, an antibody that specifically binds to human TREM2 protein exhibits cross-reactivity with a cynomolgus monkey ("cyno") TREM2 protein. In some embodiments, an antibody that specifically binds to human TREM2 protein exhibits cross-reactivity with a mouse TREM2 protein. In some embodiments, an anti-TREM2 antibody exhibits cross-reactivity with human TREM2, cyno TREM2, and mouse TREM2.

Methods for analyzing binding affinity, binding kinetics, and cross-reactivity are known in the art. These methods include, but are not limited to, solid-phase binding assays (e.g., ELISA assay), immunoprecipitation, surface plasm on resonance (e.g., Biacore™ (GE Healthcare, Piscataway, N.J.)), kinetic exclusion assays (e.g., KinExA®), flow cytometry, fluorescence-activated cell sorting (FACS), BioLayer interferometry (e.g. Octet™ (FortéBio, Inc., Menlo Park, Calif.)), and western blot analysis. In some embodiments, ELISA is used to determine binding affinity and/or cross-reactivity. Methods for performing ELISA assays are known in the art, and are also described in the Examples section below. In some embodiments, surface plasmon resonance (SPR) is used to determine binding affinity, binding kinetics, and/or cross-reactivity. In some embodiments, kinetic exclusion assays are used to determine binding affinity, binding kinetics, and/or cross-reactivity. In some embodiments, BioLayer interferometry assays are used to determine binding affinity, binding kinetics, and/or cross-reactivity.

Epitopes Recognized by Anti-TREM2 Antibodies

In some embodiments, an anti-TREM2 antibody recognizes an epitope of human TREM2 that is the same or substantially the same as the epitope recognized by an antibody clone as described herein. As used herein, the term "substantially the same," as used with reference to an epitope recognized by an antibody clone as described herein, means that the anti-TREM2 antibody recognizes an epitope that is identical, within, or nearly identical to (e.g., has at least 90% sequence identity to, or has one, two, or three amino acid substitutions, e.g., conservative substitutions, relative to), or has substantial overlap with (e.g., at least 50%, 60%, 70%, 80%, 90%, or 95% overlap with) the epitope recognized by the antibody clone as described herein.

In some embodiments, an anti-TREM2 antibody recognizes an epitope of human TREM2 that is the same or substantially the same as the epitope recognized by an antibody clone selected from the group consisting of Clone CL0020306, Clone CL0020188, Clone CL0020307, and variants of the same.

In some embodiments, an anti-TREM2 antibody binds to human TREM2 at an epitope within the stalk region of TREM2. In some embodiments, an anti-TREM2 antibody recognizes an epitope of human TREM2 comprising, within, or consisting of residues 129-172 or residues 131-169 of SEQ ID NO:1. In some embodiments, an anti-TREM2 antibody recognizes an epitope of human TREM2 comprising, within, or consisting of residues 129-148 of SEQ ID NO:1 (e.g., 143-148 of SEQ ID NO:1). In some embodiments, an anti-TREM2 antibody is an agonist that activates TREM2/DAP12 signaling (e.g., by inducing phosphorylation of a kinase such as Syk) and binds to human TREM2 at an epitope within the stalk region of TREM2. In some embodiments, an anti-TREM2 antibody binds to human TREM2 at an epitope within the stalk region of TREM2 and inhibits cleavage of TREM2 by a protease (e.g., ADAM 17).

Functional Characteristics of Anti-TREM2 Antibodies

In some embodiments, an anti-TREM2 antibody (e.g., an antibody having one or more CDR, heavy chain variable region, and/or light chain variable region sequences as disclosed) functions in one or more TREM2 activities as disclosed herein. For example, in some embodiments an anti-TREM2 antibody modulates levels of sTREM2 protein (e.g., levels of sTREM2 that are shed from the cell surface into an extracellular sample), modulates recruitment or phosphorylation of a kinase that interacts with a TREM2/DAP12 signaling complex (e.g., Syk kinase), and/or modulates one or more activities downstream of the signaling complex, such as phagocytosis, cell growth, cell survival, cell differentiation, cytokine secretion, or cell migration.

In some embodiments, an anti-TREM2 antibody enhances one or more TREM2 activities (e.g., those described herein) that are induced by a ligand. In some embodiments, the ligand is a lipid ligand. Examples of TREM2 lipid ligands include, but are not limited to, 1-palmitoyl-2-(5'-oxo-valeroyl)-sn-glycero-3-phosphocholine (POVPC), 2-Arachidonoylglycerol (2-AG), 7-ketocholesterol (7-KC), 24(S)hydroxycholesterol (24OHC), 25(S)hydroxycholesterol (25OHC), 27-hydroxycholesterol (27OHC), Acyl Carnitine (AC), alkylacylglycerophosphocholine (PAF), α-galactosylceramide (KRN7000), Bis(monoacylglycero)phosphate (BMP), Cardiolipin (CL), Ceramide, Ceramide-1-phosphate (C1P), Cholesteryl ester (CE), Cholesterol phosphate (CP), Diacylglycerol 34:1 (DG 34:1), Diacylglycerol 38:4 (DG 38:4), Diacylglycerol pyrophosphate (DGPP), Dihyrdoceramide (DhCer), Dihydrosphingomyelin (DhSM), Ether phosphatidylcholine (PCe), Free cholesterol (FC), Galactosylceramide (GalCer), Galactosylsphingosine (GalSo), Ganglioside GM1, Ganglioside GM3, Glucosylsphingosine (GlcSo), Hank's Balanced Salt Solution (HBSS), Kdo2-Lipid A (KLA), Lactosylceramide (LacCer), lysoalkylacylglycerophosphocholine (LPAF), Lysophosphatidic acid (LPA), Lysophosphatidylcholine (LPC), Lysophosphatidylethanolamine (LPE), Lysophosphatidylglycerol (LPG), Lysophosphatidylinositol (LPI), Lysosphingomyelin (LSM), Lysophosphatidylserine (LPS), N-Acyl-phosphatidylethanolamine (NAPE), N-Acyl-Serine (NSer), Oxidized phosphatidylcholine (oxPC), Palmitic-acid-9-hydroxy-stearic-acid (PAHSA), Phosphatidylethanolamine (PE), Phosphatidylethanol (PEtOH), Phosphatidic acid (PA), Phosphatidylcholine (PC), Phosphatidylglycerol (PG), Phosphatidylinositol (PI), Phosphatidylserine (PS), Sphinganine, Sphinganine-1-phosphate (Sa1P), Sphingomyelin (SM), Sphingosine, Sphingosine-1-phosphate (So1P), and Sulfatide.

Modulation of sTREM2 Shedding

In some embodiments, an anti-TREM2 antibody alters levels of sTREM2 protein in a sample, e.g., levels of sTREM2 that are shed from the cell surface into an extracellular sample. In some embodiments, an anti-TREM2 antibody decreases levels of sTREM2.

In some embodiments, an anti-TREM2 antibody decreases levels of sTREM2 if the amount of sTREM2 in a treated sample is decreased by at least 10%, at least 20%, at least 30%, at least 40%, at least 50%, at least 60%, at least 70%, at least 80%, at least 90% or more as compared to a control value. In some embodiments, an anti-TREM2 antibody decreases levels of sTREM2 if the amount of sTREM2 in a treated sample is decreased by at least 2-fold, 3-fold, 4-fold, 5-fold, 6-fold, 7-fold, 8-fold, 9-fold, 10-fold or more as compared to a control value. In some embodiments, the control value is the amount of sTREM2 in an untreated sample (e.g., a supernatant from a TREM2-expressing cell that has not been treated with an anti-TREM2 antibody, or a sample from a subject that has not been treated with an anti-TREM2 antibody) or a sample treated with an appropriate non-TREM2-binding antibody.

In some embodiments, sTREM2 shedding is measured using a sample that comprises a fluid, e.g., blood, plasma, serum, urine, or cerebrospinal fluid. In some embodiments, the sample comprises cerebrospinal fluid. In some embodiments, the sample comprises supernatant from cell cultures (e.g., supernatant from a primary cell or cell line that endogenously expresses TREM2, such as human macrophages, or a primary cell or cell line that has been engineered to express TREM2, e.g., as described in the Examples section below).

In some embodiments, the level of sTREM2 in a sample is measured using an immunoassay. Immunoassays are known in the art and include, but are not limited to, enzyme immunoassays (EIA) such as enzyme multiplied immunoassay (EMIA), enzyme-linked immunosorbent assay (ELISA), microparticle enzyme immunoassay (MEIA), immunohistochemistry (IHC), immunocytochemistry, capillary electrophoresis immunoassays (CEIA), radioimmunoassays (RIA), immunofluorescence, chemiluminescence immunoassays (CL), and electrochemiluminescence immunoassays (ECL). In some embodiments, sTREM2 levels are measuring using an ELISA assay. In some embodiments, sTREM2 levels are measured using an ELISA assay as described in the Examples section below.

Modulation of Kinase Recruitment or Phosphorylation

In some embodiments, an anti-TREM2 antibody induces phosphorylation of a kinase that interacts with the TREM2/DAP12 signaling complex (such as, but not limited to, Syk, ZAP70, PI3K, Erk, AKT, or GSK3b). In some embodiments, an anti-TREM2 antibody induces phosphorylation of a kinase that interacts with the TREM2/DAP12 signaling complex without blocking binding of a native TREM2 ligand. In some embodiments, an anti-TREM2 antibody enhances phosphorylation of a kinase that interacts with the TREM2/DAP12 signaling complex that is induced by a TREM2 ligand (e.g., a lipid ligand). In some embodiments, an anti-TREM2 antibody induces or enhances phosphorylation of Syk. In some embodiments, an anti-TREM2 antibody induces or enhances phosphorylation of Syk if the level of Syk phosphorylation in a sample treated with the anti-TREM2 antibody is increased by at least 10%, at least 20%, at least 30%, at least 40%, at least 50%, at least 60%, at least 70%, at least 80%, at least 90% or more as compared to a control value. In some embodiments, an anti-TREM2 antibody induces phosphorylation of Syk if the level of Syk phosphorylation in a sample treated with the anti-TREM2 antibody is increased by at least 2-fold, 3-fold, 4-fold, 5-fold, 6-fold, 7-fold, 8-fold, 9-fold, 10-fold, or more as compared to a control value. In some embodiments, the control value is the level of Syk phosphorylation in an untreated sample (e.g., a sample comprising a TREM2-expressing cell that has not been treated with an anti-TREM2 antibody, or a sample from a subject that has not been treated with an anti-TREM2 antibody), or a sample that has been treated with a TREM2 ligand but not an anti-TREM2 antibody, or a sample treated with an appropriate non-TREM2-binding antibody.

For detecting and/or quantifying phosphorylation (e.g., Syk phosphorylation) in a sample, in some embodiments, an immunoassay is used. In some embodiments, the immunoassay is an enzyme immunoassay (EIA), enzyme multiplied immunoassay (EMIA), enzyme-linked immunosorbent assay (ELISA), microparticle enzyme immunoassay (MEIA), immunohistochemistry (IHC), immunocytochemistry, capillary electrophoresis immunoassay (CEIA), radioimmunoassay (RIA), immunofluorescence, chemiluminescence immunoassay (CL), or electrochemiluminescence immunoassay (ECL). In some embodiments, phosphorylation is detected and/or quantified using an immunoassay that utilizes an amplified luminescent proximity homogenous assay (AlphaLISA®, PerkinElmer Inc.).

In some embodiments, phosphorylation is measured using a sample that comprises one or more cells, e.g., one or more TREM2-expressing cells (e.g., a primary cell or cell line that endogenously expresses TREM2, such as human macrophages or iPSC-derived microglia, or a primary cell or cell line that has been engineered to express TREM2, e.g., as described in the Examples section below). In some embodiments, the sample comprises a fluid, e.g., blood, plasma, serum, urine, or cerebrospinal fluid. In some embodiments, the sample comprises tissue (e.g., lung, brain, kidney, spleen, nervous tissue, or skeletal muscle) or cells from such tissue. In some embodiments, the sample comprises endogenous fluid, tissue, or cells (e.g., from a human or non-human subject).

Modulation of Phagocytosis

In some embodiments, an anti-TREM2 antibody enhances phagocytosis of dead cell debris, tissue debris, amyloid beta particles, or foreign material. In some embodiments, an anti-TREM2 antibody enhances phagocytosis without blocking binding of a native TREM2 ligand. In some embodiments, an anti-TREM2 antibody enhances phagocytosis that is induced by a TREM2 ligand (e.g., a lipid ligand). In some embodiments, an anti-TREM2 antibody enhances phagocytosis if the level of phagocytosis in a sample treated with the anti-TREM2 antibody is increased by at least 10%, at least 20%, at least 30%, at least 40%, at least 50%, at least 60%, at least 70%, at least 80%, at least 90% or more as compared to a control value. In some embodiments, an anti-TREM2 antibody enhances phagocytosis if the level of phagocytosis in a sample treated with the anti-TREM2 antibody is increased by at least 2-fold, 3-fold, 4-fold, 5-fold, 6-fold, 7-fold, 8-fold, 9-fold, 10-fold, or more as compared to a control value. In some embodiments, the control value is the level of phagocytosis in an untreated sample, a sample that has been treated with a TREM2 ligand but not an anti-TREM2 antibody, or a sample treated with an appropriate non-TREM2-binding antibody.

In some embodiments, phagocytosis is measured using a phagocytosis assay with a labeled substrate. Phagocytosis assays are known in the art. In some embodiments, the phagocytosis assay is performed on a sample comprising cells that endogenously express TREM2, such as human macrophages or microglia. In some embodiments, the phagocytosis assay is performed on a sample comprising cells that have been engineered to express TREM2. In some embodiments, phagocytosis is measured using a human macrophage phagocytosis assay as described in the Examples section below.

Modulation of Cell Differentiation, Function, Migration, and Survival

In some embodiments, an anti-TREM2 antibody enhances cell migration, cell survival, cell function, or cell differentiation (e.g., for myeloid cells, macrophages, and microglia, including iPSC-derived microglia and disease-associated microglia). Disease-associated microglia and methods of detecting disease-associated microglia are described in Keren-Shaul et al., *Cell* 2017, 169:1276-1290. In some embodiments, an anti-TREM2 antibody enhances cell migration of one or more cell types (e.g., myeloid cells, macrophages, or microglia). In some embodiments, an anti-TREM2 antibody enhances cell survival of one or more cell types (e.g., myeloid cells, macrophages, or microglia). In some embodiments, an anti-TREM2 antibody enhances cell function of one or more cell types (e.g., myeloid cells, macrophages, or microglia). In some embodiments, an anti-TREM2 antibody enhances cell differentiation of one or more cell types (e.g., myeloid cells, macrophages, or microglia). In some embodiments, an anti-TREM2 antibody enhances the migration, survival, function, and/or differentiation of myeloid cells. In some embodiments, an anti-TREM2 antibody enhances the migration, survival, function, and/or differentiation of macrophages. In some embodiments, an anti-TREM2 antibody enhances the migration, survival, function, and/or differentiation of microglia. In some embodiments, an anti-TREM2 antibody enhances microglia activation. In some embodiments, an anti-TREM2 antibody enhances the migration, survival, function, and/or differentiation of disease-associated microglia. In some embodiments, an anti-TREM2 antibody enhances cell migration, cell survival, cell function, or cell differentiation without blocking binding of a native TREM2 ligand. In some embodiments, an anti-TREM2 antibody enhances cell migration, cell survival, cell function, or cell differentiation that is induced by a TREM2 ligand (e.g., a lipid ligand).

In some embodiments, an anti-TREM2 antibody enhances cell migration, cell survival, cell function, or cell differentiation if the level of activity (e.g., migration, survival, function, or differentiation) in a sample treated with the anti-TREM2 antibody is increased by at least 10%, at least 20%, at least 30%, at least 40%, at least 50%, at least 60%, at least 70%, at least 80%, at least 90% or more as compared to a control value. In some embodiments, an anti-TREM2 antibody enhances cell migration, cell survival, cell function, or cell differentiation if the level of activity (e.g., migration, survival, function, or differentiation) in a sample treated with the anti-TREM2 antibody is increased by at least 2-fold, 3-fold, 4-fold, 5-fold, 6-fold, 7-fold, 8-fold, 9-fold, 10-fold, or more as compared to a control value. In some embodiments, the control value is the level of activity (e.g., migration, survival, function, or differentiation) in an untreated sample (e.g., a sample that has not been treated with an anti-TREM2 antibody), a sample that has been treated with a TREM2 ligand but not an anti-TREM2 antibody, or a sample treated with an appropriate non-TREM2-binding antibody.

In some embodiments, cell migration is measured using a chemotaxis assay. Chemotaxis assays are known in the art. In some embodiments, the cell migration assay (e.g., chemotaxis assay) is performed on a sample comprising cells that endogenously express TREM2, such as human macrophages. In some embodiments, the cell migration assay (e.g., chemotaxis assay) is performed on a sample comprising cells that have been engineered to express TREM2. In some embodiments, cell migration is measured using a human macrophage chemotaxis assay as described in the Examples section below.

In some embodiments, cell survival is measured using a cell viability assay. Cell viability assays are known in the art. In some embodiments, the cell survival assay (e.g., cell viability assay) is performed on a sample comprising cells that endogenously express TREM2, such as human macrophages. In some embodiments, the cell survival assay (e.g., cell viability assay) is performed on a sample comprising cells that have been engineered to express TREM2. In some embodiments, cell survival is measured using a human macrophage viability assay as described in the Examples section below.

In some embodiments, cell function is measured using a functional assay that is appropriate for that cell. For example, in some embodiments, macrophage cell function is evaluated using a phagocytosis assay, e.g., as described in the Examples section below.

In some embodiments, cell differentiation is measured by evaluating the ability of cells that endogenously express TREM2 to differentiate. For example, in some embodiments, cell differentiation is measured by evaluating the ability of macrophages to differentiate from monocytes, e.g., as described in the Examples section below.

In some embodiments, activation of microglia is measured in vivo. In some embodiments, microglia activation is measured using TSPO-PET imaging. TSPO-PET imaging methods are known in the art.

In some embodiments, an anti-TREM2 antibody enhances microglia function without increasing neuroinflammation. Levels of neuroinflammation can be determined by measuring levels of cytokines (e.g., inflammatory cytokines), such as but not limited to TNF-α, IL-1β, IL-6, IL-1ra, TGFβ, IL-15, or IFN-γ. In some embodiments, cytokine levels are measured using immunoassays, for example, an enzyme immunoassay (EIA), enzyme multiplied immunoassay (EMIA), enzyme-linked immunosorbent assay (ELISA), microparticle enzyme immunoassay (MEIA), immunohistochemistry (IHC), immunocytochemistry, capillary electrophoresis immunoassay (CEIA), radioimmunoassay (RIA), immunofluorescence, chemiluminescence immunoassay (CL), or electrochemiluminescence immunoassay (ECL).

IV. Fc Polypeptide Mutations of Proteins Having Anti-TREM2 Antigen Binding Portion In some aspects, an anti-TREM2 antibody comprises two Fc polypeptides, one or both of which may each comprise independently selected modifications (e.g., mutations) or may be a wild-type Fc polypeptide, e.g., a human IgG1 Fc polypeptide. Non-limiting examples of mutations that can be introduced into one or both Fc polypeptides include, e.g., mutations to permit binding of an Fc polypeptide (or antibody comprising the same) to a BBB-receptor, such as transferrin receptor (TfR) protein (e.g., a human or cynomolgus TfR, such as may be expressed on a brain endothelial cell), mutations to increase serum stability, to modulate effector function, to influence glycosylation, to reduce immunogenicity in humans, and/or to provide for knob and hole heterodimerization of the Fc polypeptides.

Transferrin Receptor-Binding Mutations

In some embodiments, an anti-TREM2 antibody includes an Fc polypeptide that comprises modifications (e.g., amino acid substitutions) that permit binding of the Fc polypeptide to a TfR protein. Briefly, binding to a TfR protein (e.g., to the apical domain thereof) that is expressed on, for example, a brain endothelial cell, can, in some embodiments, permit a modified Fc polypeptide of this disclosure or an antibody comprising the same to cross the blood-brain barrier via receptor-mediated transcytosis. In certain embodiments, receptor-mediated transcytosis can enhance or improve the ability of the protein comprising the Fc polypeptide to be present in the brain (i.e., on the luminal side of the blood-brain barrier), which can allow for improved binding to TREM2 in the CNS, and other functions, e.g., clearance, neutralization, or immunodepletion of the target, or the like.

Exemplary TfR-binding amino acid modifications to an Fc (e.g., CH2 and/or CH3 portion, fragment, or domain), and Fc polypeptides and portions thereof that comprise the amino acid modifications, are described in PCT patent publication no. WO 2018/152326A1. These amino acid modifications, TfR-binding Fc polypeptide sequences and TfR-binding Fc polypeptides, and techniques for generating and testing the same are incorporated herein by reference. One or two Fc polypeptides of an Fc dimer of the present disclosure can be engineered to comprise modifications to permit binding to TfR. In certain embodiments, one Fc polypeptide of an Fc dimer comprises modifications to permit binding to TfR, and the other Fc polypeptide does not.

In some embodiments, a modified Fc polypeptide comprises a YxTEWSS (SEQ ID NO:58) motif. In some embodiments, a modified Fc polypeptide comprises a TxxExxxxF (SEQ ID NO:59) motif. In some embodiments, a modified Fc polypeptide comprises a YxTEWSS (SEQ ID NO:58) and a TxxExxxxF (SEQ ID NO:59) motif.

In some embodiments, a modified Fc polypeptide comprises a wild-type amino acid residue at positions 380, 389, 390, and 415, according to EU numbering, wherein the wild-type amino acid residue is found at a corresponding position in SEQ ID NO:38.

In some embodiments, an anti-TREM2 antibody includes an Fc polypeptide having the following amino acids: Trp, Leu, or Glu at position 380; Tyr or Phe at position 384; Thr at position 386; Glu at position 387; Trp at position 388; Ser, Ala, or Val at position 389; Ser or Asn at position 390; Thr or Ser at position 413; Glu or Ser at position 415; Glu at position 416; and Phe at position 421, according to EU numbering.

In some embodiments, the anti-TREM2 antibody includes an Fc polypeptide having the following amino acids: Trp at position 380; Tyr at position 384; Thr at position 386; Glu at position 387; Trp at position 388; Ser at position 389; Ser at position 390; Thr at position 413; Glu at position 415; Glu at position 416; and Phe at position 421, according to EU numbering.

In some embodiments, an anti-TREM2 antibody includes an Fc polypeptide having the following amino acids: Glu at position 380; Phe at position 384; Thr at position 386; Glu at position 387; Trp at position 388; Ser at position 389; Asn at position 390; Ser at position 413; Glu at position 415; Glu at position 416; and Phe at position 421, according to EU numbering.

In some embodiments, an anti-TREM2 antibody includes an Fc polypeptide having the following amino acids: Glu at position 380; Tyr at position 384; Thr at position 386; Glu at position 387; Trp at position 388; Val at position 389; Asn at position 390; Thr at position 413; Glu at position 415; Glu at position 416; and Phe at position 421, according to EU numbering.

In some embodiments, an anti-TREM2 antibody includes an Fc polypeptide having the following amino acids: Glu at position 380; Tyr at position 384; Thr at position 386; Glu at position 387; Trp at position 388; Ser at position 389; Asn at position 390; Ser at position 413; Glu at position 415; Glu at position 416; and Phe at position 421, according to EU numbering.

In some embodiments, a modified Fc polypeptide comprises a sequence having at least 90% identity to an amino acid sequence set forth in any one of SEQ ID NOS:40, 43, 46, and 49. In some embodiments, a modified Fc polypeptide comprises or consists of the amino acid sequence set forth in any one of SEQ ID NOS:41, 44, 47, and 50.

Additional examples of modified Fc polypeptides are described in Table 8.

Mutations to Promote Heterodimerization of Fc Polypeptides

In some embodiments, the Fc polypeptides present in an anti-TREM2 antibody as disclosed herein include knob and hole mutations to promote heterodimer formation and hinder homodimer formation. Generally, the modifications introduce a protuberance ("knob") at the interface of a first polypeptide and a corresponding cavity ("hole") in the interface of a second polypeptide, such that the protuberance can be positioned in the cavity so as to promote heterodimer formation and thus hinder homodimer formation.

Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine). In some embodiments, such additional mutations are at a position in the Fc polypeptide that does not have a negative (e.g., inhibitory) effect on binding of a Fc polypeptide to a BBB receptor, e.g., TfR.

In one illustrative embodiment of a knob and hole approach for dimerization, position 366 (numbered according to the EU numbering scheme) of one of the Fc polypeptides present in the proteins described herein comprises a tryptophan in place of a native threonine. The other Fc polypeptide in the dimer has a valine at position 407 (numbered according to the EU numbering scheme) in place of the native tyrosine. The other Fc polypeptide may further comprise a substitution in which the native threonine at position 366 (numbered according to the EU numbering scheme) is substituted with a serine and a native leucine at position 368 (numbered according to the EU numbering scheme) is substituted with an alanine. Thus, one of the Fc polypeptides of an anti-TREM2 protein of the disclosure has the T366W knob mutation and the other Fc polypeptide has the Y407V mutation, which is typically accompanied by the T366S and L368A hole mutations.

In some embodiments, one or both Fc polypeptides may also be engineered to contain other modifications for heterodimerization, e.g., electrostatic engineering of contact residues within a CH3-CH3 interface that are naturally charged or hydrophobic patch modifications.

In some embodiments, modifications to enhance serum half-life may be introduced. For example, in some embodiments, one or both Fc polypeptides present in an anti-TREM2 protein of the disclosure may comprise a tyrosine at position 252, a threonine at position 254, and a glutamic acid at position 256, as numbered according to the EU numbering scheme. Thus, one or both Fc polypeptides may have M252Y, S254T, and T256E substitutions. Alternatively, one or both Fc polypeptides may have M428L and/or N434S substitutions, according to EU numbering. Alternatively, one or both Fc polypeptides may have an N434S or N434A substitution.

Fc Effector Functions

In some embodiments, one or both Fc polypeptides in an anti-TREM2 protein disclosed herein may comprise modifications that reduce effector function, i.e., having a reduced ability to induce certain biological functions upon binding to an Fc receptor expressed on an effector cell that mediates the effector function. Examples of antibody effector functions include, but are not limited to, C1q binding and complement dependent cytotoxicity (CDC), Fc receptor binding, antibody-dependent cell-mediated cytotoxicity (ADCC), antibody-dependent cell-mediated phagocytosis (ADCP), down-regulation of cell surface receptors (e.g., B cell receptor), and B-cell activation. Effector functions may vary with the antibody class. For example, native human IgG1 and IgG3 antibodies can elicit ADCC and CDC activities upon binding to an appropriate Fc receptor present on an immune system cell; and native human IgG1, IgG2, IgG3, and IgG4 can elicit ADCP functions upon binding to the appropriate Fc receptor present on an immune cell.

In some embodiments, one or both Fc polypeptides may include modifications that modulate effector function.

In some embodiments, one or both Fc polypeptides may comprise modifications that reduce or eliminate effector function. Illustrative Fc polypeptide mutations that reduce effector function include, but are not limited to, substitutions in a CH2 domain, e.g., at positions 234 and 235, according to the EU numbering scheme. For example, in some embodiments, one or both Fc polypeptides can comprise alanine residues at positions 234 and 235. Thus, one or both Fc polypeptides may have L234A and L235A (LALA) substitutions.

Additional Fc polypeptide mutations that modulate an effector function include, but are not limited to, the following: position 329 may have a mutation in which proline is substituted with a glycine, arginine, serine, or an amino acid residue large enough to destroy the Fc/Fcγ receptor interface that is formed between proline 329 of the Fc and tryptophan residues Trp 87 and Trp 110 of FcγRIII. Additional illustrative substitutions include S228P, E233P, L235E, N297A, N297D, N297G, and P331S, according to the EU numbering scheme. Multiple substitutions may also be present, e.g., L234A and L235A of a human IgG1 Fc region; L234A, L235A, and P329G of a human IgG1 Fc region; L234A, L235A, and P329S of a human IgG1 Fc region; S228P and L235E of a human IgG4 Fc region; L234A and G237A of a human IgG1 Fc region; L234A, L235A, and G237A of a human IgG1 Fc region; V234A and G237A of a human IgG2 Fc region; L235A, G237A, and E318A of a human IgG4 Fc region; and S228P and L236E of a human IgG4 Fc region, according to the EU numbering scheme. In some embodiments, one or both Fc polypeptides may have one or more amino acid substitutions that modulate ADCC, e.g., substitutions at positions 298, 333, and/or 334, according to the EU numbering scheme.

FcRn Binding Sites and Mutations to Increase Serum Half-Life

In certain aspects, Fc polypeptides (e.g., modified Fc polypeptides) present in an anti-TREM2 protein of the disclosure, can comprise an FcRn binding site. In some embodiments, the FcRn binding site is within the Fc polypeptide or a fragment thereof.

In some embodiments, the FcRn binding site comprises a native FcRn binding site. In some embodiments, the FcRn binding site does not comprise amino acid changes relative to the amino acid sequence of a native FcRn binding site. In some embodiments, the native FcRn binding site is an IgG binding site, e.g., a human IgG binding site. In some embodiments, the FcRn binding site comprises a modification that alters FcRn binding.

In some embodiments, an FcRn binding site has one or more amino acid residues that are mutated, e.g., substituted, wherein the mutation(s) increase serum half-life or do not substantially reduce serum half-life (i.e., reduce serum half-life by no more than 25% compared to a counterpart Fc polypeptide having the wild-type residues at the mutated positions when assayed under the same conditions). In some embodiments, an FcRn binding site has one or more amino acid residues that are substituted at positions 251-256, 428, and 433-436, according to the EU numbering scheme.

In some embodiments, one or more residues at or near an FcRn binding site are mutated, relative to a native human IgG sequence, to extend serum half-life of the polypeptide. In some embodiments, mutations are introduced into one, two, or three of positions 252, 254, and 256. In some embodiments, the mutations are M252Y, S254T, and T256E. In some embodiments, an Fc polypeptide further comprises the mutations M252Y, S254T, and T256E. In particular embodiments, one or both Fc polypeptides present in an anti-TREM2 protein of the disclosure may comprise a tyrosine at position 252, a threonine at position 254, and a glutamic acid at position 256, as numbered according to the EU numbering scheme. Thus, one or both Fc polypeptides may have M252Y, S254T, and T256E substitutions.

In some embodiments, the mutations are M428L and/or N434S. In some embodiments, an Fc polypeptide further comprises the mutation N434S with or without M428L. In some embodiments, an Fc polypeptide comprises a mutation at one, two, or all three of positions T307, E380, and N434, according to the EU numbering scheme. In some embodiments, the mutations are T307Q and N434A. In some embodiments, an Fc polypeptide comprises mutations T307A, E380A, and N434A. In some embodiments, an Fc polypeptide comprises mutations at positions T250 and M428, according to the EU numbering scheme. In some embodiments, the Fc polypeptide comprises mutations T250Q and/or M428L. In some embodiments, an Fc polypeptide comprises mutations at positions M428 and N434, according to the EU numbering scheme. In some embodiments, the Fc polypeptide comprises mutations M428L and N434S. In some embodiments, an antibody of the present disclosure can comprise two Fc polypeptides, wherein each of the two Fc polypeptides comprises M428L and/or N434S substitutions. In some embodiments, the Fc polypeptide comprises an N434S or N434A mutation. In some embodiments, an antibody of the present disclosure can comprise two Fc polypeptides, wherein each of the two Fc polypeptides comprises an N434S or N434A substitution.

V. Preparation of Antibodies

In some embodiments, antibodies are prepared by immunizing an animal or animals (e.g., mice, rabbits, or rats) with an antigen or a mixture of antigens for the induction of an antibody response. In some embodiments, the antigen or mixture of antigens is administered in conjugation with an adjuvant (e.g., Freund's adjuvant). After an initial immunization, one or more subsequent booster injections of the antigen or antigens may be administered to improve antibody production. Following immunization, antigen-specific B cells are harvested, e.g., from the spleen and/or lymphoid tissue. For generating monoclonal antibodies, the B cells are fused with myeloma cells, which are subsequently screened for antigen specificity. Methods of preparing antibodies are also described in the Examples section below.

The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Alternatively, phage or yeast display technology can be used to identify antibodies and Fab fragments that specifically bind to selected antigens. Antibodies can also be made bispecific, i.e., able to recognize two different antigens. Antibodies can also be heteroconjugates, e.g., two covalently joined antibodies, or immunotoxins.

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

In some embodiments, the antibody is a chimeric antibody. Methods for making chimeric antibodies are known in the art. For example, chimeric antibodies can be made in which the antigen binding region (heavy chain variable region and light chain variable region) from one species, such as a mouse, is fused to the effector region (constant domain) of another species, such as a human. As another example, "class switched" chimeric antibodies can be made in which the effector region of an antibody is substituted with an effector region of a different immunoglobulin class or subclass.

In some embodiments, the antibody is a humanized antibody. Generally, a non-human antibody is humanized in order to reduce its immunogenicity. Humanized antibodies typically comprise one or more variable regions (e.g., CDRs) or portions thereof that are non-human (e.g., derived from a mouse variable region sequence), and possibly some framework regions or portions thereof that are non-human, and further comprise one or more constant regions that are derived from human antibody sequences. Methods for humanizing non-human antibodies are known in the art. Transgenic mice, or other organisms such as other mammals, can be used to express humanized or human antibodies. Other methods of humanizing antibodies include, for example, variable domain resurfacing, CDR grafting, grafting specificity-determining residues (SDR), guided selection, and framework shuffling.

As an alternative to humanization, fully human antibodies can be generated. As a non-limiting example, transgenic animals (e.g., mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. As another example, human antibodies can be produced by hybridoma-based methods, such as by using primary human B cells for generating cell lines producing human monoclonal antibodies.

Human antibodies can also be produced using phage display or yeast display technology. In phage display, repertoires of variable heavy chain and variable light chain genes are amplified and expressed in phage display vectors. In some embodiments, the antibody library is a natural repertoire amplified from a human source. In some embodiments, the antibody library is a synthetic library made by cloning heavy chain and light chain sequences and recombining to generate a large pool of antibodies with different antigenic specificity. Phage typically display antibody fragments (e.g., Fab fragments or scFv fragments), which are then screened for binding to an antigen of interest.

In some embodiments, antibody fragments (such as a Fab, a Fab', a F(ab')$_2$, a scFv, a $V_H$, or a $V_{HH}$) are generated. Various techniques have been developed for the production of antibody fragments. Traditionally, these fragments were derived via proteolytic digestion of intact antibodies. However, these fragments can now be produced directly using recombinant host cells. For example, antibody fragments can be isolated from antibody phage libraries. Alternatively, Fab'-SH fragments can be directly recovered from E. coli cells and chemically coupled to form F(ab')$_2$ fragments. According to another approach, F(ab')$_2$ fragments can be isolated directly from recombinant host cell culture. Other techniques for the production of antibody fragments will be apparent to those skilled in the art.

In some embodiments, an antibody or an antibody fragment is conjugated to another molecule, e.g., polyethylene glycol (PEGylation) or serum albumin, to provide an extended half-life in vivo.

VI. Nucleic Acids, Vectors, and Host Cells

In some embodiments, the anti-TREM2 antibodies as disclosed herein are prepared using recombinant methods. Accordingly, in some aspects, the disclosure provides isolated nucleic acids comprising a nucleic acid sequence encoding any of the anti-TREM2 antibodies as described herein (e.g., any one or more of the CDRs, heavy chain variable regions, and light chain variable regions described herein); vectors comprising such nucleic acids; and host cells into which the nucleic acids are introduced that are used to replicate the antibody-encoding nucleic acids and/or to express the antibodies.

In some embodiments, a polynucleotide (e.g., an isolated polynucleotide) comprises a nucleotide sequence encoding an antibody as described herein (e.g., as described in the Section above entitled "Anti-TREM2 Antibody Sequences"). In some embodiments, the polynucleotide comprises a nucleotide sequence encoding one or more amino acid sequences (e.g., CDR, heavy chain, or light chain sequences) disclosed in Table 8 below. In some embodiments, the polynucleotide comprises a nucleotide sequence encoding an amino acid sequence having at least 85% sequence identity (e.g., at least 85%, at least 90%, at least 91%, at least 92%, at least 93%, at least 94%, at least 95%, at least 96%, at least 97%, at least 98%, or at least 99% sequence identity) to a sequence (e.g., a CDR, heavy chain, or light chain sequence) disclosed in Table 8 below. In some embodiments, a polynucleotide as described herein is operably linked to a heterologous nucleic acid, e.g., a heterologous promoter.

Suitable vectors containing polynucleotides encoding antibodies of the present disclosure, or fragments thereof, include cloning vectors and expression vectors. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Examples include plasmids and bacterial viruses, e.g., pUC18, pUC19, Bluescript (e.g., pBS SK+) and its derivatives, mpl8, mpl9, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicate in the host cells either as episomes or as an integral part of the chromosomal DNA. Suitable expression vectors include but are not limited to plasmids, viral vectors, including adenoviruses, adeno-associated viruses, retroviruses, and any other vector.

Suitable host cells for cloning or expressing a polynucleotide or vector as described herein include prokaryotic or eukaryotic cells. In some embodiments, the host cell is prokaryotic. In some embodiments, the host cell is eukaryotic, e.g., Chinese Hamster Ovary (CHO) cells or lymphoid cells. In some embodiments, the host cell is a human cell, e.g., a Human Embryonic Kidney (HEK) cell.

In another aspect, methods of making an anti-TREM2 antibody as described herein are provided. In some embodiments, the method includes culturing a host cell as described herein (e.g., a host cell expressing a polynucleotide or vector as described herein) under conditions suitable for expression of the antibody. In some embodiments, the antibody is subsequently recovered from the host cell (or host cell culture medium).

VII. Therapeutic Methods Using Anti-TREM2 Antibodies

In another aspect, therapeutic methods using an anti-TREM2 antibody as disclosed herein (e.g., an anti-TREM2 antibody as described in Section III above) are provided. In some embodiments, methods of treating a neurodegenerative disease are provided. In some embodiments, methods of modulating one or more TREM2 activities (e.g., in a subject having a neurodegenerative disease) are provided.

In some embodiments, methods of treating a neurodegenerative disease are provided. In some embodiments, the neurodegenerative disease is selected from the group consisting of Alzheimer's disease, primary age-related tauopathy, progressive supranuclear palsy (PSP), frontotemporal dementia, frontotemporal dementia with parkinsonism linked to chromosome 17, argyrophilic grain dementia, amyotrophic lateral sclerosis, amyotrophic lateral sclerosis/parkinsonism-dementia complex of Guam (ALS-PDC), corticobasal degeneration, chronic traumatic encephalopathy, Creutzfeldt-Jakob disease, dementia pugilistica, diffuse neurofibrillary tangles with calcification, Down's syndrome, familial British dementia, familial Danish dementia, Gerstmann-Straussler-Scheinker disease, globular glial tauopathy, Guadeloupean parkinsonism with dementia, Guadelopean PSP, Hallevorden-Spatz disease, hereditary diffuse leukoencephalopathy with spheroids (HDLS), Huntington's disease, inclusion-body myositis, multiple system atrophy, myotonic dystrophy, Nasu-Hakola disease, neurofibrillary tangle-predominant dementia, Niemann-Pick disease type C, pallido-ponto-nigral degeneration, Parkinson's disease, Pick's disease, postencephalitic parkinsonism, prion protein cerebral amyloid angiopathy, progressive subcortical gliosis, subacute sclerosing panencephalitis, and tangle only dementia. In some embodiments, the neurodegenerative disease is Alzheimer's disease. In some embodiments, the neurodegenerative disease is Nasu-Hakola disease. In some embodiments, the neurodegenerative disease is frontotemporal dementia. In some embodiments, the neurodegenerative disease is Parkinson's disease. In some embodiments, the method comprises administering to the subject an isolated antibody or an antigen-binding fragment thereof that specifically binds to a human TREM2 protein, e.g., an anti-TREM2 antibody as described herein, or a pharmaceutical composition comprising an anti-TREM2 antibody as described herein.

In some embodiments, an anti-TREM2 antibody (or antigen-binding portion or pharmaceutical composition thereof) as described herein is used in treating a neurodegenerative disease that is characterized by a mutation in TREM2. In some embodiments, the neurodegenerative disease that is characterized by a mutation in TREM2 is Alzheimer's disease, e.g., Alzheimer's disease that is characterized by a R47H mutation in TREM2.

In some embodiments, methods of modulating one or more TREM2 activities in a subject (e.g., a subject having a neurodegenerative disease) are provided. In some embodiments, the method comprises modulating levels of sTREM2; modulating recruitment or phosphorylation of a kinase that interacts with a TREM2/DAP12 signaling complex (e.g., Syk kinase); modulating phagocytosis (e.g., phagocytosis of cell debris, amyloid beta particles, etc.); modulating cell migration (e.g., migration of myeloid cells, macrophages, microglia, and disease associated microglia); and/or modulating cell differentiation (e.g., for myeloid cells, macrophages, microglia, and disease associated microglia). In some embodiments, methods of enhancing one or more TREM2 activities in a subject having a neurodegenerative disease are provided. In some embodiments, methods of decreasing levels of sTREM2 in a subject having a neurodegenerative disease are provided. In some embodiments, the method of modulating one or more TREM2 activities in a subject comprises administering to the subject an isolated antibody or an antigen-binding portion thereof that specifically binds to a human TREM2 protein, e.g., an anti-TREM2 antibody as describe herein, or a pharmaceutical composition comprising an anti-TREM2 antibody as described herein.

In some embodiments, the subject to be treated is a human, e.g., a human adult or a human child.

In some embodiments, methods of reducing plaque accumulation in a subject having a neurodegenerative disease are provided. In some embodiments, the method comprises administering to the subject an antibody or pharmaceutical composition as described herein. In some embodiments, the subject has Alzheimer's disease. In some embodiments, the subject is an animal model of a neurodegenerative disease (e.g., a 5XFAD or APP/PS1 mouse model). In some embodiments, plaque accumulation is measured by amyloid plaque imaging and/or Tau imaging, e.g., using positron emission tomography (PET) scanning. In some embodiments, administration of an anti-TREM2 antibody reduces plaque accumulation by at least 20%, at least 30%, at least 40%, at least 50%, at least 60%, at least 70%, at least 80%, or at least 90% as compared to a baseline value (e.g., the level of plaque accumulation in the subject prior to administration of the anti-TREM2 antibody).

In some embodiments, an anti-TREM2 antibody is administered to a subject at a therapeutically effective amount or dose. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is well within the capability of those skilled in the art.

The route of administration of an anti-TREM2 antibody as described herein can be oral, intraperitoneal, transdermal, subcutaneous, intravenous, intramuscular, intrathecal, inhalational, topical, intralesional, rectal, intrabronchial, nasal, transmucosal, intestinal, ocular or otic delivery, or any other methods known in the art. In some embodiments, the antibody is administered orally, intravenously, or intraperitoneally.

In some embodiments, the anti-TREM2 antibody (and optionally another therapeutic agent) is administered to the subject over an extended period of time, e.g., for at least 30, 40, 50, 60, 70, 80, 90, 100, 150, 200, 250, 300, 350 days or longer.

VIII. Pharmaceutical Compositions and Kits

In another aspect, pharmaceutical compositions and kits comprising an antibody that specifically binds to a human TREM2 protein are provided. In some embodiments, the pharmaceutical compositions and kits are for use in treating a neurodegenerative disease. In some embodiments, the pharmaceutical compositions and kits are for use in modulating (e.g., enhancing or inhibiting) one or more TREM2 activities, e.g., Syk phosphorylation. In some embodiments, the pharmaceutical compositions and kits are for use in modulating (e.g., decreasing) sTREM2 levels.

Pharmaceutical Compositions

In some embodiments, pharmaceutical compositions comprising an anti-TREM2 antibody or an antigen-binding fragment thereof are provided. In some embodiments, the anti-TREM2 antibody is an antibody as described in Section III above or an antigen-binding fragment thereof.

In some embodiments, a pharmaceutical composition comprises an anti-TREM2 antibody as described herein and further comprises one or more pharmaceutically acceptable carriers and/or excipients. A pharmaceutically acceptable carrier includes any solvents, dispersion media, or coatings that are physiologically compatible and that does not interfere with or otherwise inhibit the activity of the active agent. Various pharmaceutically acceptable excipients are well-known in the art.

In some embodiments, the carrier is suitable for intravenous, intramuscular, oral, intraperitoneal, intrathecal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known in the art.

The pharmaceutical compositions described herein can be manufactured in a manner that is known to those of skill in the art, e.g., by means of conventional mixing, dissolving, granulating, dragee-making, emulsifying, encapsulating, entrapping or lyophilizing processes. The following methods and excipients are merely exemplary and are in no way limiting.

For oral administration, an anti-TREM2 antibody can be formulated by combining it with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

An anti-TREM2 antibody can be formulated for parenteral administration by injection, e.g., by bolus injection or continuous infusion. For injection, the compound or compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, compounds can be formulated in aqueous solutions, e.g., in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Typically, a pharmaceutical composition for use in in vivo administration is sterile. Sterilization can be accomplished according to methods known in the art, e.g., heat sterilization, steam sterilization, sterile filtration, or irradiation.

Dosages and desired drug concentration of pharmaceutical compositions of the disclosure may vary depending on the particular use envisioned. The determination of the appropriate dosage or route of administration is well within the skill of one in the art. Suitable dosages are also described in Section VII above.

Kits

In some embodiments, kits comprising an anti-TREM2 antibody are provided. In some embodiments, the anti-TREM2 antibody is an antibody as described in Section III above or an antigen-binding fragment thereof.

In some embodiments, the kit further comprises one or more additional therapeutic agents. For example, in some embodiments, the kit comprises an anti-TREM2 antibody as described herein and further comprises one or more additional therapeutic agents for use in the treatment of a neurodegenerative disease, e.g., Alzheimer's disease. In some embodiments, the therapeutic agent is an agent for use in treating a cognitive or behavioral symptom of a neurodegenerative disease (e.g., an antidepressant, a dopamine agonist, or an anti-psychotic). In some embodiments, the therapeutic agent is a neuroprotective agent (e.g., carbidopa/levodopa, an anticholinergic agent, a dopaminergic agent, a monoamine oxidase B (MAO-B) inhibitor, a catechol-O-methyl transferase (COMT) inhibitor, a glutamatergic agent, a histone deacetylase (HDAC) inhibitor, a cannabinoid, a caspase inhibitor, melatonin, an anti-inflammatory agent, a hormone (e.g., estrogen or progesterone), or a vitamin).

In some embodiments, the kit comprises an anti-TREM2 antibody as described herein and further comprises one or more reagents for measuring sTREM2 levels. In some embodiments, the kit comprises an anti-TREM2 antibody as described herein and further comprises one or more reagents for measuring TREM2 activity (e.g., for measuring Syk phosphorylation).

In some embodiments, the kit further comprises instructional materials containing directions (i.e., protocols) for the practice of the methods described herein (e.g., instructions for using the kit for a therapeutic method as described in Section VI above). While the instructional materials typically comprise written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD-ROM), and the like. Such media may include addresses to internet sites that provide such instructional materials.

IX. Examples

The present disclosure will be described in greater detail by way of specific examples. The following examples are offered for illustrative purposes only, and are not intended to limit the disclosure in any manner.

Example 1. Generation and Initial Characterization of Anti-TREM2 Antibodies

Recombinant Expression and Purification of Mouse Fc Fused Human TREM2 ECD

The ecto domain (residues 19-172) of human TREM2 (UniProtKB ID—Q9NZC2) was subcloned into pRK vector with the secretion signal from mouse IgG kappa chain V-III, amino acids 1-20 (UniProtKB ID—P01661) at the N-terminal region, and a mouse Fc tag at the C-terminal region with a GGGGS (SEQ ID NO:34) between TREM2 ECD and Fc.

Purified plasmid was transfected into Expi293F™ cells (Thermo Fisher) using the Expi293F™ Expression System Kit according to the manufacturer's instructions. To inhibit maturation of N-linked glycans and reduce glycosylation heterogeneity, kifunensine (Sigma), an inhibitor of high mannosidase I was added to the culture at 1 µg/mL concentration immediately after transfection. Transfected cells were incubated in an orbital shaker (Infors HT Multitron) at 125 rpm and 37° C. in a humidified atmosphere of 6% $CO_2$. ExpiFectamine™ 293 Transfection Enhancer 1 and 2 were added to the cells 16 hours post transfection and the media supernatant was harvested 96 hours post transfection. The clarified supernatant was supplemented with EDTA-free protease inhibitor (Roche) and was stored at −80° C.

For rhTREM2-Fc isolation, clarified media supernatant was loaded on HiTrap MabSelect SuRe Protein A affinity column (GE Healthcare Life Sciences) and washed with 200 mM arginine and 137 mM succinate buffer pH 5.0. The fusion protein was eluted in 100 mM QB citrate buffer pH 3.0 and 50 mM NaCl. Immediately after elution, 1M Tris-HCl buffer pH 8.0 was added to the protein solution to neutralize the pH. Protein aggregates were separated by size exclusion chromatography (SEC) on Superdex 200 increase 10/300 GL column (GE Healthcare Life Sciences). The SEC mobile phase buffer was kept at 20 mM Tris-HCl pH 8.0, 100 mM NaCl and 50 mM arginine, which was also the protein storage buffer. All chromatography steps were performed on AKTA pure or AKTA Avant systems (GE Healthcare Life Sciences).

Recombinant Expression and Purification of his-Tagged TREM2 ECD

The ecto domain (residues 19-172) of TREM2 (UniProtKB—Q9NZC2) was subcloned in the pRK vector with the secretion signal from mouse Ig kappa chain V-III, amino acids 1-20 (UniProtKB ID—P01661) at the N-terminal region, and a 6×-His tag (SEQ ID NO:35) at the C-terminal region. The insert was verified by sequencing and maxi prep plasmid purification was performed.

Purified plasmid was transfected into Expi293F™ cells (Thermo Fisher) using the Expi293F™ Expression System Kit according to the manufacturer's instructions. Transfected cells were incubated in an orbital shaker (Infors HT Multitron) at 125 rpm and 37° C. in a humidified atmosphere of 6% $CO_2$. ExpiFectamine™ 293 Transfection Enhancer 1 and 2 were added to the cells 16 hours post transfection and the media supernatant was harvested 96 hours post transfection.

Harvested media was supplemented with 1M imidazole pH 8.0 to a final concentration of 10 mM and filtered using the Nalgene™ Rapid-Flow™ disposable filter units (Thermo Fisher) with a pore size of 0.4 microns. HisPur™ Ni-NTA Resin (Thermo Fisher) was washed with MQ water and equilibrated with load buffer (20 mM Tris pH 8.0, 150 mM NaCl, and 10 mM imidazole). Affinity purification was performed using the gravity flow method. The harvested media was loaded onto the resin and nonspecifically bound proteins were washed with load buffer supplemented with 50 mM and 100 mM imidazole. The bound His-tagged TREM2 eco domain was eluted with 20 mM Tris pH 8.0, 150 mM NaCl, and 200 mM imidazole. Eluted protein was concentrated using Amicon 10 kDa concentrators and the concentrated protein was further purified by gel filtration chromatography using the AKTA Avant system (GE Healthcare Life Sciences). The protein was loaded onto a HiLoad Superdex 200 16/600 (GE Healthcare Life Sciences) column equilibrated with 1×PBS and eluted and fractionated using 1×PBS as the running buffer. Eluted fractions were analyzed by electrophoresis on polyacrylamide (PAGE) gels under denaturing and native conditions. Eluted fractions were further characterized by analytical size exclusion chromatography and the intact protein mass determination. Results from the PAGE and analytical characterization were used to pool the heavily glycosylated protein fractions and these were aliquoted and stored at −80° C.

Generation of Antibodies

Rodents (mice and rats) were immunized using standard protocols with rhTREM2-Fc immunogen or BWZ cells expressing full length Trem2 receptor. Titers were measured throughout immunization using sera collected at different time points. The detection of an antigen specific immune response was performed using flow cytometry with the rhTREM2-Fc immunogen and live BWZ cells expressing full-length TREM2. Selection criteria of candidate antibodies included rodent antibody production and specificity of binding to TREM2 as detected by flow cytometry. Antibody-secreting cells were isolated from animal immune tissues including spleen, lymph nodes and bone marrow.

Single cell suspensions were analyzed to determine the binding properties of secreted antibodies. Antibody-secreting cells were loaded into microfluidic devices and isolated in nanoliter volume reaction chambers to enable the detection of secreted antibodies using fluorescent and brightfield image-based microscopy assays (see, e.g., U.S. Pat. No. 9,188,593). Binding assays involving detection of antibodies binding to antigen-coated micro-beads, detection of soluble fluorescently-labeled antigen binding to antibodies immobilized on beads, and detection of antibody binding to cell surface-expressed antigens were carried out. Cell surface-expressed antigens included both recombinant form and the native forms of antigens presented on the surface of cells.

Image analysis was used to identify chambers exhibiting positive fluorescent signals, indicating the presence of a single cell producing antibodies with the desired properties, and the contents of chambers were recovered and lysed in 384 well plates (see, e.g., U.S. Pat. No. 10,087,408). Single cell lysates were then subjected to RT-PCR to amplify the heavy and light chain variable region sequences. The resulting amplicons were then sequenced to determine the cDNA sequence of paired heavy and light chain variable regions from the selected single cells. The resulting sequences were manually inspected and analyzed to determine sequence diversity and somatic hypermutation. Sequences were selected for expression based on screening data and sequence diversity. Expressed antibodies were tested to confirm antigen binding specificity.

Example 2. Sequence Optimization and Humanization of Anti-TREM2 Antibodies

Exemplary anti-TREM2 antibodies were sequence optimized and humanized, followed by characterization for binding kinetics and binding specificity.

Sequence optimization was conducted by searching within CDR sequences for residues that are susceptible to chemical modification (e.g., asparagine deamidation motifs (NG), aspartic acid isomerization motifs (DS), and potential oxidation residues (tryptophan (W) and methionine (M)) and making amino acid substitutions with conservative and germline residues to remove such sequence liabilities. Humanized and sequence-optimized variants of anti-TREM2 antibodies were then analyzed for binding kinetics using Biacore and dose-titrated cell binding to HEK293-H6 cells (see, Example 5 for representative protocols).

Example 3. Generation of Anti-TREM2 Antibodies Having Modified Fc Polypeptides ("ATV:TREM2")

The Fd ($V_H$+CH1) region of a humanized, affinity matured anti-TREM2 antibody (SEQ ID NOS:22 and 24) was cloned into expression vectors comprising a sequence encoding an Fc polypeptide engineered to bind to the human transferrin receptor (TfR) (CH3C.35.23.1.1, CH3C.35.23.3, CH3C.35.23.3 cisLALA, or CH3C.35.24) or a sequence encoding an Fc polypeptide that binds to the cynomolgus monkey transferrin receptor (CH3C.35.21). The Fc polypeptide-encoding sequence also contained a "knob" (T366W) mutation to prevent homodimerization and promote heterodimerization with an Fc polypeptide comprising "hole" (T366S/L368A/Y407V) mutations. The Fd region was also cloned into corresponding "hole" vectors comprising a sequence encoding an Fc polypeptide with hole mutations, but lacking the TfR binding mutations. The coding sequences (both Fd-knob-Fc and Fd-hole-Fc constructs) also contained "LALA" (L234A; L235A) mutations in the hinge region to reduce effector function (Wines et al., J. Immunol. 764:5313-5318 (2000) and "LS" (M428L; N434S) mutations in the Fc CH3 region to increase binding to FcRn (see, e.g., Zalevsky et al., Nat. Biotech. 28(2): 157-159 (2010)). The final encoded heavy chain sequences expressed by the vectors are set forth in Table 1.

TABLE 1

| ATV:TREM2 Sequences | | |
|---|---|---|
| ATV:TREM2 | First Heavy Chain | Second Heavy Chain |
| #1 | SEQ ID NO: 42 | SEQ ID NO: 53 |
| #2 | SEQ ID NO: 45 | SEQ ID NO: 53 |
| #3 | SEQ ID NO: 48 | SEQ ID NO: 53 |
| #4 | SEQ ID NO: 48 | SEQ ID NO: 52 |
| #5 | SEQ ID NO: 51 | SEQ ID NO: 53 |

The corresponding aforementioned knob and hole vectors were co-transfected to ExpiCHO or Expi293 cells along with the corresponding light chain vector (SEQ ID NO:54) in the ratio knob:hole:light chain of 1:1:2. The expressed protein was purified by Protein A chromatography followed by preparative size-exclusion chromatography (SEC) to isolate purified anti-TREM2 protein.

Binding of anti-TREM2 protein to human transferrin receptor was determined as follows: anti-human-Fab was immobilized on a CM5 chip, and the anti-TREM2 protein was captured. Full-length human TfR or human TfR apical domain at serial dilution (e.g., concentrations of 1-1,000 nM) was flowed over the chip (180 second association time) and then allowed to dissociate. Fitting was performed using a 1:1 binding model.

Example 4. Characterization of Anti-TREM2 Antibodies

The following sections describe various assays that were carried out to assess the binding and functional characteristics of generated anti-TREM2 antibodies.

Affinity Measurement by Biacore Kinetic Measurement

Surface plasmon resonance (Biacore™ 8K instrument) was used to measure anti-TREM2 antibody affinities for human and cynomolgus TREM2 ECD. Anti-TREM2 antibodies were captured using Human Fab Capture Kit (GE Healthcare Life Sciences, Catalog No. 28958325) on a Biacore Series S CM5 sensor chip (GE Healthcare Life Sciences, Catalog No. 29149604). Serial 3-fold dilutions of recombinant human or cynomolgus TREM2 were injected at a flow rate of 30 µL/min. Antibody binding was monitored for 300 seconds, followed by monitoring of antibody dissociation for 600+ seconds in HBS-EP+ running buffer (GE Healthcare Life Sciences, Catalog No. BR100669). The binding response was corrected by subtracting the RU value from a blank flow cell. A 1:1 Languir model of simultaneous fitting of $k_{on}$ and $k_{off}$ was used for kinetics analysis. $K_D$ binding values were calculated from $k_{on}$ and $k_{off}$.

Evaluation of TREM2 Binding in TREM2-Expressing HEK Cells

The binding characteristics of anti-TREM2 antibodies was evaluated in HEK 293 cells expressing human TREM2 as follows.

A HEK 293 cell line stably expressing human TREM2/DAP12 was generated by transfecting the cells with a vector expressing wild type human TREM2 and DAP12, and DAP12 alone, respectively. Stable expressing clones were selected, and the cell surface TREM2 expression was evaluated by flow cytometry. APC-conjugated rat anti-human/mouse-TREM2 monoclonal antibody (R&D, Catalog No. MAB17291) was used to detect surface TREM2 expression. The clone showing the highest wild type TREM2 expression level was selected and named "HEK293-H6." The clones stably expressing DAP12 were analyzed by Western blot, and the selected clone was named "HEK293-DAP12#1."

HEK 293 overexpressing human TREM2 (HEK293-H6) and HEK 293 overexpressing GFP (B5) were harvested by 0.05% trypsin and incubated at 37° C. for 2 hours. After incubation, the cells were centrifuged and washed in FACS buffer (PBS+0.5% BSA) twice. Mixed cells were resuspended in FACS buffer with human Trustain FcX solution (Biolegend, Catalog No. 422302) at a density of 10⁶/mL per cell line. The mixed cell lines were seeded at 200,000 cells per well in a 96-well round-bottom plate and incubated for 20 minutes at room temperature. After incubation, the cells were centrifuged and incubated with a dose titration of anti-TREM2 antibodies for 45 minutes on ice. After incubation, the cells were centrifuged and washed with FACS buffer three times. The cells were then incubated with secondary antibody (Alexa Fluor 647 AffiniPure F(ab')2 Fragment Goat Anti-human IgG(FFHL), Jackson ImmunoResearch Laboratories, Catalog No. 109-606-088, 1:800 dilution) for 30 minutes on ice. After incubation, the cells were washed with FACS buffer three times, resuspended in 100 µL of FACS buffer, and analyzed by flow cytometry (BD FACSCanto II, San Jose, Calif.), for which 30,000 events were obtained for each sample. Mean fluorescence intensity per cells were calculated by FlowJo software and used for generating dose response binding curve.

Activation of TREM2-Dependent pSyk Signaling

Activation of TREM2-dependent pSyk signaling was measured in human macrophage cells or in HEK293-H6 cells using a commercial AlphaLisa assay from PerkinElmer.

For all experiments involving use of lipid vesicles containing 70% DOPC and 30% POPS, the lipid vesicles were prepared within two weeks of experiments as follows: 7 mg DOPC (1,2-dioleoyl-sn-glycero-3-phosphocholine) and 3 mg POPS (1-palmitoyl-2-oleoyl-sn-glycero-3-phospho-L-serine) were combined in chloroform in a glass vial and dried under a stream of $N_2$ gas for 1-2 hours, or until completely dry. The lipid mixture was re-suspended in 1 mL HBSS (for a final lipid concentration of about 10 mg/mL) and vortexed for 2-3 minutes. Subsequently, the lipid suspension was extruded using an Avanti mini-extruder constructed with one 100-nm pore size membrane to form small unilamellar vesicles at 10 mg/mL.

1. Dosing of Antibodies in Cells

The day before assay, human macrophage cells or HEK293-H6 cells were plated at 100,000 cells/well or 40,000 cells/well, respectively, on a 96-well plate coated with poly-D-lysine. Antibodies were diluted in a 10-point serial dilution with 3-fold dilution between points into PBS. For antagonist dose-response curves, lipid vesicles containing 70% DOPC and 30% POPS at 1 mg/mL final concentration were also included in the antibody/PBS mixture. The cells were washed 3 times with HBSS using a Biotek 405/406 plate washer, after which 50 µL per well of the antibody/PBS (with or without vesicles) solution was added using a Hamilton Nimbus liquid handler. The cell plate was then transferred to a 37° C. incubator for 5 minutes. The liposome/antibody solution was removed by flicking the plate, and 40 µL lysis buffer (Cell Signaling Technologies, CST) containing 1 µM PMSF was added using the liquid handler. The lysate was then either frozen at −80° C. or immediately assayed in the AlphaLisa assay.

Human macrophage cells were prepared for assay as follows. Human monocytes were isolated following the RosetteSep human monocyte enrichment cocktail protocol (Stemcell Technologies, REF #15068) from fresh blood. Isolated monocytes were washed in wash buffer (PBS+2% FBS) and resuspended in 10 mL ACK lysis buffer (ThermoFisher Scientific, Catalog No. A10492) to lyse red blood cells. Twenty (20) mL of wash buffer was added to stop cell lysis, and the sample was centrifuged and washed once more with culture media (RPMI, 10% Hyclone FBS, 1% Sodium Pyruvate, 1% Glutamax, 1% non-essential amino acids, and 1% Penicillin-streptomycin). Human monocytes were then differentiated into macrophage cells in culture media in the presence of 50 ng/mL human recombinant M-CSF (Gibco, Catalog No. PHC9501) at 250-mL flask. Fresh human M-CSF was spiked on day 3 and human macrophages were subsequently harvested on day 5 and used for assay.

2. AlphaLisa Assay

Cell lysates were assayed for pSyk using the standard protocol for the Perkin Elmer pSyk AlphaLisa kit. In brief, 10 μL of lysate/well was transferred to a white opaque 384 well Optiplate (Perkin Elmer). Next, 5 μL of Acceptor Mix (containing the working solution of acceptor beads) was added per well, followed by sealing of plates with foil seals and incubation for 1 hour at room temperature. Subsequently, 5 μL of Donor Mix (containing the working solution of donor beads) was added to each well under reduced light conditions. Plates were again sealed and incubated for 1 hour at room temperature. Finally, the plates were read using AlphaLisa settings on a Perkin Elmer EnVision plate reader.

Survival Assay in Human Macrophage Cells

Human monocytes were isolated following the RosetteSep human monocyte enrichment cocktail protocol (Stemcell Technologies, Catalog No. 15068). Isolated monocytes were washed in wash buffer (PBS+2% FBS) and resuspended in 10 mL ACK lysis solution (ThermoFisher Scientific, Catalog No. A10492) to lyse red blood cells. Twenty (20) mL wash buffer was added to stop lysis. The cell suspension was centrifuged and washed once with culture media (RPMI 1640+10% FBS+penicillin/streptomycin). Cells were resuspended in culture media at a density of $10^6$ cells μL/mL and used in the survival assay described below.

The day prior to assay, 96-well plates were pre-coated with anti-TREM2 antibody or isotype control in a dose titration (45 μL/well, total 12 points) and incubated overnight at 4° C. After overnight incubation, the pre-coated plate was washed twice with PBS and then loaded with human monocyte ($10^5$ cells/well) in the presence of low concentration human M-CSF (5 ng/mL, Gibco, Catalog No. PHC9501). After 5 days at 37° C., the media was aspirated, and 100 μL PBS+100 μL Celltiter-glo media (Promega, Catalog No. G7571) was added to each well. After 10 minutes of incubation, the cell media was transferred to multiwell plates compatible for luminometer use, and luminescence for cell viability was recorded.

Livid Storage Assay

Prior to assay, induced human pluripotent stem cells (iPSCs) were first differentiated into hematopoietic progenitor cells (HPCs) using a commercially available kit (STEMdiff Hematopoietic Kit from StemCell Technologies). HPCs were transferred to a plate containing primary human astrocytes and co-cultured for 14-21 days. Once floating cells in co-culture were predominantly identified as mature microglia (>80%), the microglia were used for assay.

Cells (iPSC-derived human microglia, 30,000 cells/well) were plated on PDL-coated 96-well plates in full serum media. After 24 hours at 37° C., the media was exchanged for full serum media containing oleic acid-albumin (10 μM or 33 μM final concentration, Sigma O3008) or purified unlabeled myelin (50 μg/mL final concentration, purified from wildtype C57Bl/6 mouse brain (Jackson Laboratories) using methods described in Safaiyan et al. (2016, *Nature Neuroscience* 19(8):995-998)). After 24 hours at 37° C. of lipid treatment, the media was exchanged for media containing anti-TREM2 antibody. For single point experiments, the concentration of anti-TREM2-antibody used was 100 nM. For dose-response curves, media containing 100 nM anti-TREM2 antibody was serially diluted 3-fold for a total of 10 points. RSV was used as a control. The cells were incubated for another 48 hours at 37° C. before imaging cells using Bodipy stain, or extracting the cells for lipidomics, as described below.

For Bodipy imaging, the supernatant was removed, and cells were incubated at 37° C. for 30 minutes in live cell imaging buffer (Life Technologies, Catalog No. A14291DJ) containing 1:2500 of a 1 mg/mL Bodipy 493/503 solution in DMSO (Thermo-Fisher D3922) and 1 drop/mL of Nucblue (ThermoFisher, Catalog No. R37605). After the incubation period, the staining solution was removed, and the cells were either imaged live or fixed in 4% paraformaldehyde. The cells were imaged using the Alexa 488 channel for Bodipy, and DAPI illumination settings on an Opera Phoenix high content confocal imager. Lipid spots were analyzed using a spot-finding algorithm on the Harmony software supplied with the instrument.

For lipidomic analysis, cells were washed once with PBS while kept on ice. A volume of 70 μL of a 9:1 methanol:water solution containing 1:100 internal standards was added to the cells in the 96-well plate. The plate was agitated on a shaker at 4° C. and 1200 rpm for 20 minutes and then centrifuged for 5 minutes at 300×g. A 50 μL sample of supernatant was transferred to LCMS vials and kept at −80° C. until analyzed on the instrument.

Lipid levels were analyzed by liquid chromatography (Shimadzu Nexera X2 system, Shimadzu Scientific Instrument, Columbia, Md., USA) coupled to electrospray mass spectrometry (QTRAP 6500+, Sciex, Framingham, Mass., USA). For each analysis, 5 μL of sample was injected on a BEH C18 1.7 μm, 2.1×100 mm column (Waters Corporation, Milford, Mass., USA) using a flow rate of 0.25 mL/min at 55° C. For positive ionization mode, mobile phase A consisted of 60:40 acetonitrile/water (v/v) with 10 mM ammonium formate+0.1% formic acid; mobile phase B consisted of 90:10 isopropyl alcohol/acetonitrile (v/v) with 10 mM ammonium formate+0.1% formic acid. For negative ionization mode, mobile phase A consisted of 60:40 acetonitrile/water (v/v) with 10 mM ammonium acetate; mobile phase B consisted of 90:10 isopropyl alcohol/acetonitrile (v/v) with 10 mM ammonium acetate. The gradient was programmed as follows: 0.0-8.0 min from 45% B to 99% B, 8.0-9.0 min at 99% B, 9.0-9.1 min to 45% B, and 9.1-10.0 min at 45% B. Electrospray ionization was performed in either positive or negative ion mode applying the following settings: curtain gas at 30; collision gas set at medium; ion spray voltage at 5500 (positive mode) or 4500 (negative mode); temperature at 250° C. (positive mode) or 600° C. (negative mode); ion source Gas 1 at 50; ion source Gas 2 at 60. Data acquisition was performed using Analyst 1.6.3 (Sciex) in multiple reaction monitoring mode (MRM), with the following parameters: dwell time (msec) and collision energy (CE); declustering potential (DP) at 80; entrance potential (EP) at 10 (positive mode) or −10 (negative mode), and collision cell exit potential (CXP) at 12.5 (positive mode) or −12.5 (negative mode). Lipids were quantified using a mixture of non-endogenous internal standards. Lipids were identified based on their retention times and MRM properties of commercially available reference standards (Avanti Polar Lipids, Birmingham, Ala., USA).

Activation of TREM2-Dependent mTOR Signaling

Wild-type iPSC-derived human microglia were cultured and treated with anti-TREM2 antibody (100 nM final concentration) and either DMSO or a commercial mTOR inhibitor (Selleckchem, Catalog No. AZD8055, 20 nM final concentration) for 96 hours. The treated cells were subsequently lysed, and the cell lysates were prepared for Western blots to investigate phosphorylation of major signaling targets in the mTOR pathway. Primary antibodies for Western blots were obtained from Cell Signaling Technologies: (1) phospho-mTOR (Ser2448), Product No. 5536T; (2) mTOR (7C10), Product No. 2983T; (3) phospho-AKT (Ser473), Product No. 9271T; (3) phospho-GSK-3beta (Ser9), Product No.

5558T; (4) phospho-S6 ribosomal protein (S235/236), Product No. 4858T; (5) phospho-4E-BP1 (Thr37/46), Product No. 2855T; (6) beta-actin, Product No. 58169S.

Example 5. Results

Results for an analysis of the binding characteristics of humanized and sequence-optimized variants of antibody CL0020188 are provided in Table 2 and FIGS. 1A-1H. NG motifs in the CL0020188 CDR-H2 sequence (SEQ ID NO:5) and CDR-L1 sequence (SEQ ID NO:7) were modified, grafted onto human framework regions, and analyzed. Table 2 provides $K_D$ values as measured by Biacore and $EC_{50}$ values as measured by dose-titrated binding assay in HEK293-H6 cells. FIGS. 1A-1H include representative dose-response curves of binding to TREM2 expressed by HEK293-H6 cells for the humanized and sequence-optimized variants. Variants are represented by solid black circles (•), while isotype controls are represented by open white circles (°).

TABLE 2

Binding Characteristics of Sequence-Optimized and Humanized Variants of CL0020188

| Clone | $hV_H$ | $hV_L$ | $K_D$ | $EC_{50}$ |
|---|---|---|---|---|
| CL0020188-1 | NG/graft | NG/graft | 2.3 nM | 0.42 nM |
| CL0020188-2 | NG/3m | NG/graft | 3.4 nM | 0.26 nM |
| CL0020188-3 | NG/graft | TG/graft | 6.8 nM | 0.64 nM |
| CL0020188-4 | NG/3m | TG/graft | 4.8 nM | 0.44 nM |
| CL0020188-5 | NA/graft | NG/graft | 5.1 nM | 0.45 nM |
| CL0020188-6 | NA/3m | NG/graft | 4.0 nM | 0.31 nM |
| CL0020188-7 | NA/graft | TG/graft | 10 nM | 0.68 nM |
| CL0020188-8 | NA/3m | TG/graft | 7.3 nM | 0.51 nM |
| Parent | | | 9.5 nM | 0.44 nM |

3m = A24G/L45P/V48L in $V_H$

As illustrated in Table 2, humanized and sequence-optimized clones of CL00201088 exhibited similar affinity values for hTREM2 compared to the parent antibody ($K_D$=9.5 nM), as measured by Biacore. This was consistent with cell-binding results in HEK293-H6 cells, which are illustrated in Table 1, with corresponding dose-response curves provided in FIGS. 1A-1H. Compared to the parent antibody ($EC_{50}$=0.44 nM), humanized and sequence-optimized clones exhibited comparable and sub-nanomolar affinity for TREM2 expressed in HEK293-H6 cells. Taken together, the results indicate comparable binding kinetics between the parent antibody and the humanized and sequence-optimized variants.

Figure 2:
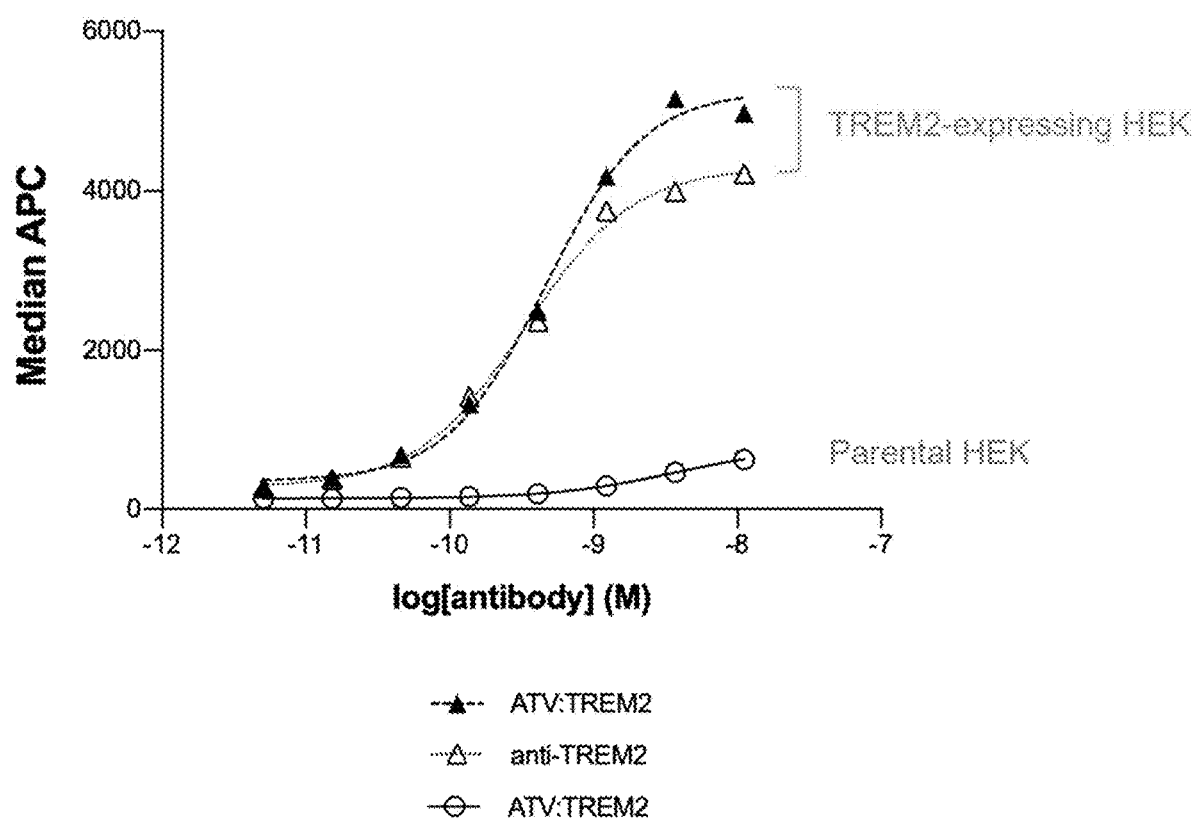
FIG. 2 includes dose-response binding curves to human TREM2 in HEK 293 cells for a representative ATV:TREM2 and corresponding anti-TREM2 antibody with non-transferrin-binding Fc ("anti-TREM2").

Results for ATV:TREM2 variants described in Example 3 are summarized in Table 3 below. An exemplary cell binding curve based on binding to human TREM2-expressing HEK cells and analysis by FACS is illustrated in FIG. 2.

TABLE 3

Summary of ATV:TREM2 Characteristics

| | Biacore $K_D$ (nM) | | | EC50 (nM) |
|---|---|---|---|---|
| ATV:TREM2 | Human TREM2 | Cyno TREM2 | Human TfR | Human TREM2 HEK |
| #1 | TBD | TBD | TBD | TBD |
| #2 | 5.4 | 2.4 | 650 | 4.9 |
| #3 | 3.0 | 2.2 | 1400 | 4.6 |
| #4 | 2.0 | 2.2 | TBD | TBD |
| #5 | 5.7 | 2.4 | 620 | 3.6 |

TBD = to be determined

Figure 3:
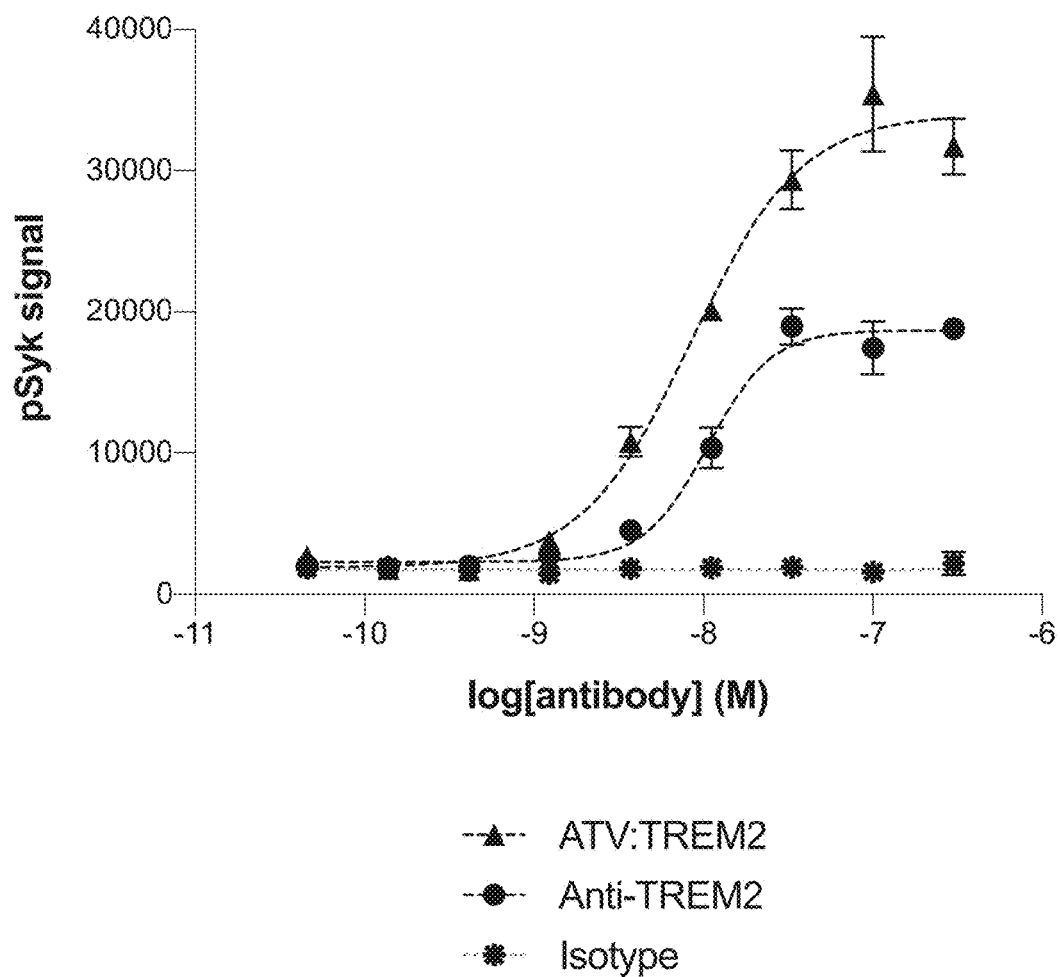
FIG. 3 includes dose-response curves of pSyk signal activation by a representative ATV:TREM2 and corresponding anti-TREM2 antibody (TREM2 IgG) in TREM2-expressing HEK 293 cells.
Figure 4A:
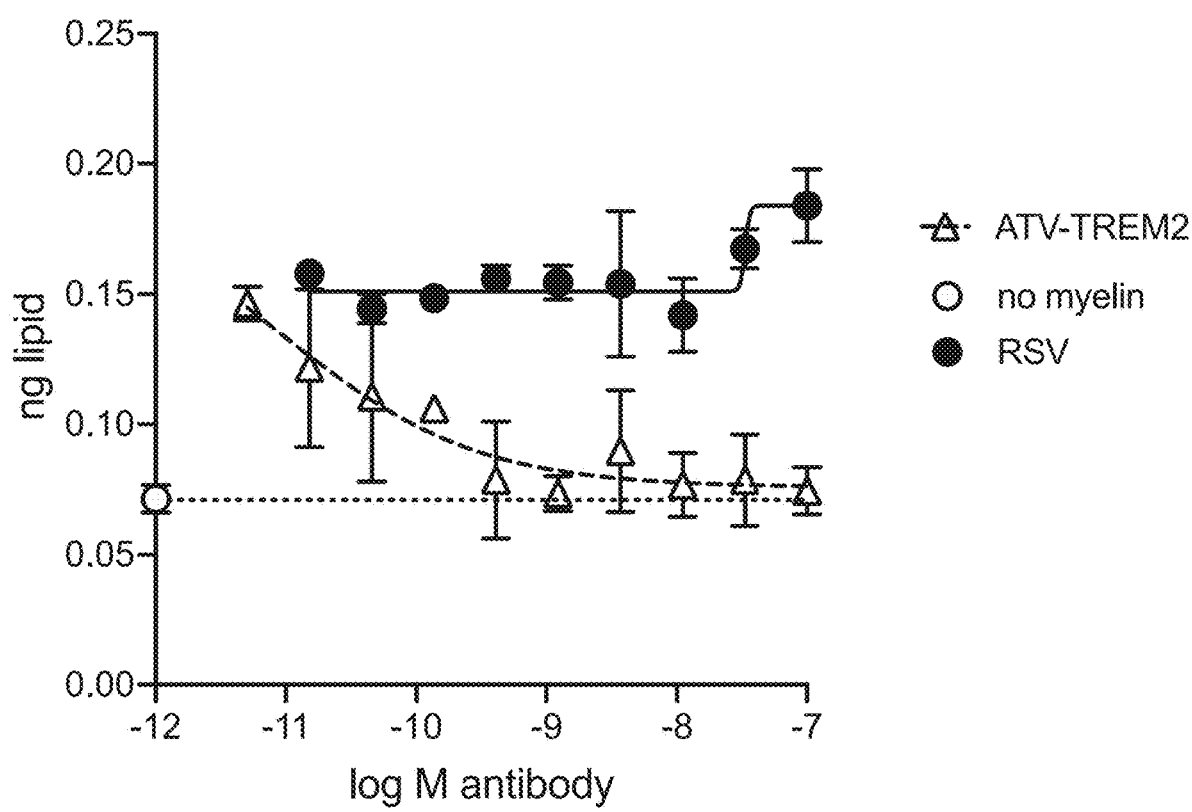
FIGS. 4A and 4B include dose-response curves of lipid clearance in iPSC microglia in response to treatment with a representative ATV:TREM2.
Figure 4B:
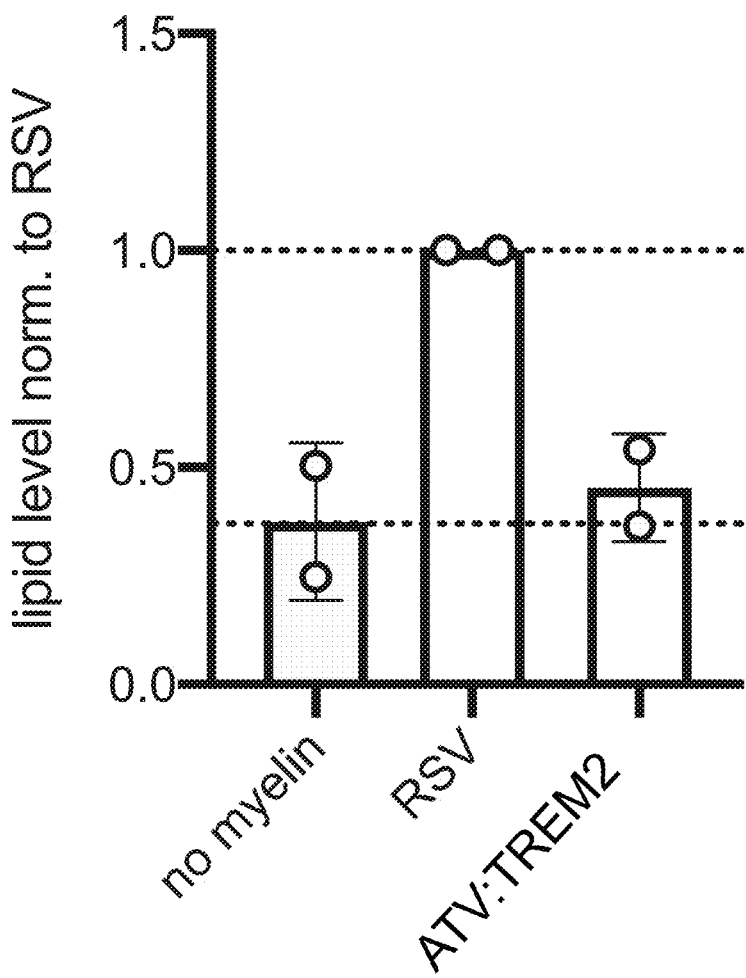

The antibodies were also assessed for TREM2-dependent pSyk signaling in HEK-H6 cells, capability for promoting survival of human macrophage cells, and ability to modulate lipid accumulation in iPSC-derived human microglial cells (hereinafter referenced as "iPSC microglia" or "iMG"). FIG. 3 illustrates the results for an ATV:TREM2 variant (ATV:TREM2 #3) and a corresponding anti-TREM2 antibody. The ATV:TREM2 was able to activate pSyk signaling in TREM2-expressing HEK293-H6 cells to a significantly greater extent than the corresponding TREM2 antibody, indicating that the addition of ATV to the molecule can increase its potency (FIG. 3). In addition, the ATV:TREM2 induced macrophage survival with an $EC_{50}$ of 4.1+0.3 nM. Finally, the anti-TREM2 antibodies demonstrated capability in reducing lipid accumulation in myelin-treated iMG (FIGS. 4A and 4B) with an $IC_{50}$ for inhibition of lipid storage of 0.20 nM (97.7+0.3% max. inhibition).

Figure 5A:
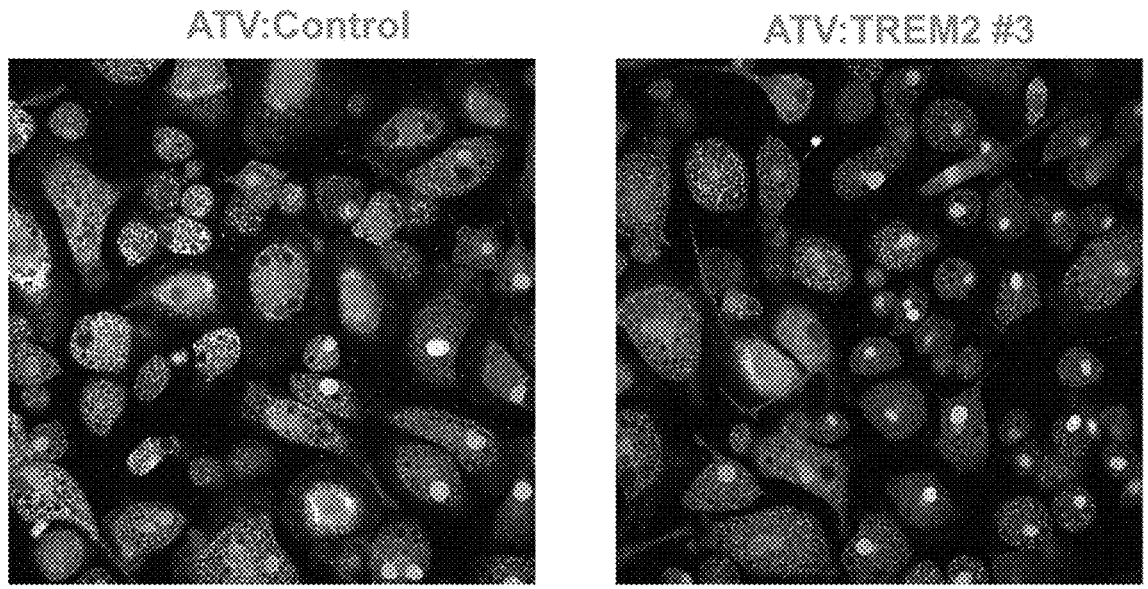
FIGS. 5A and 5B show representative images of lipid accumulation in iPSC-derived microglial cells treated with ATV:TREM2 after oleic acid challenge (FIG. 5A) with quantification of lipid accumulation in treated cells (FIG. 5B).
Figure 5B:
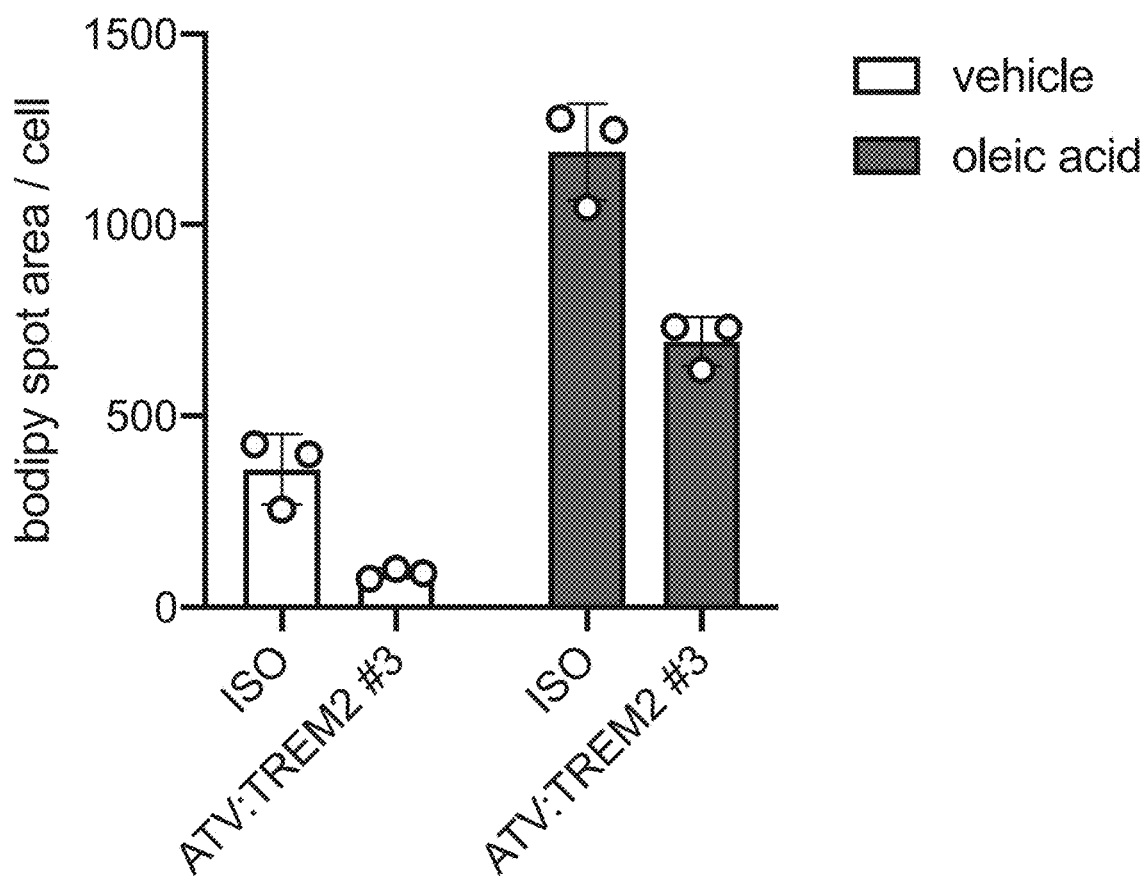
Figure 5C:
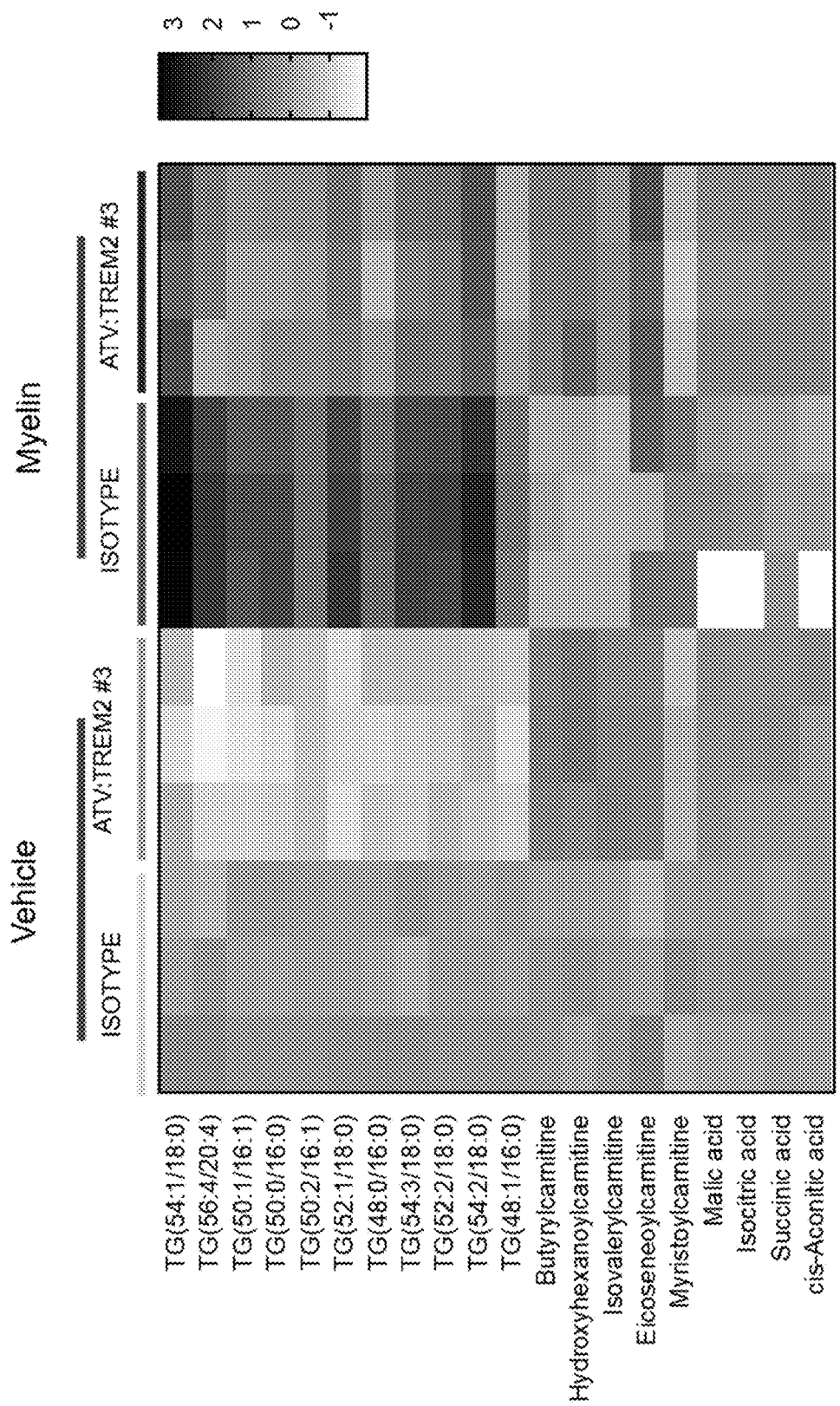
FIG. 5C is a heat map illustrating the modulation of levels of triglyceride, acyl carnitine, and TCA cycle intermediate species in iPSC-derived microglial cells treated with ATV:TREM2 after myelin challenge.
Figure 5D:
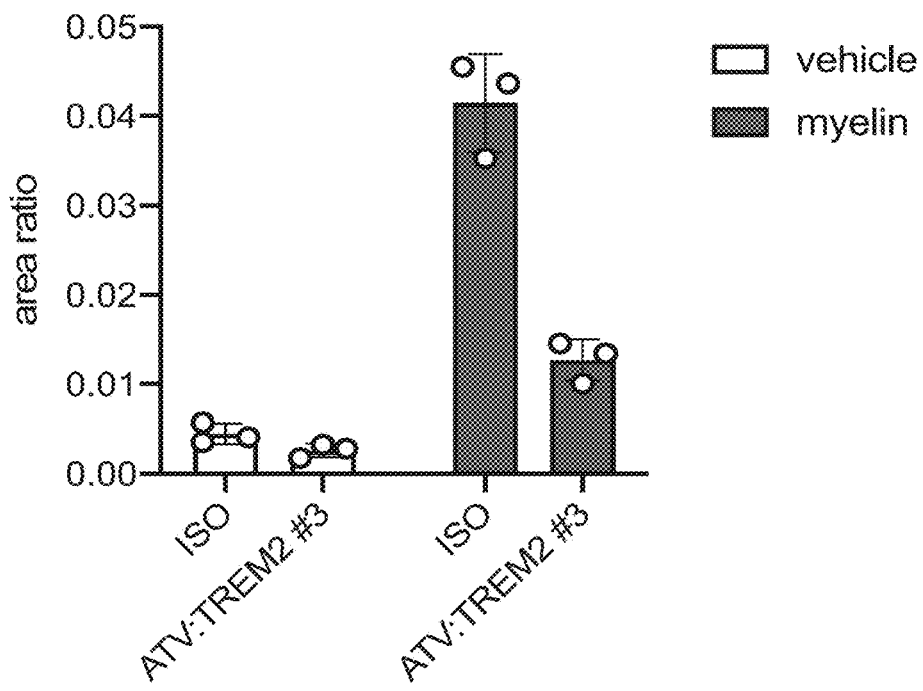
FIGS. 5D-5F include bar graphs illustrating the change in levels of representative triglyceride, acyl carnitine, and TCA cycle intermediate species levels in iPSC-derived microglial cells treated with ATV:TREM2 after myelin challenge.
Figure 5E:
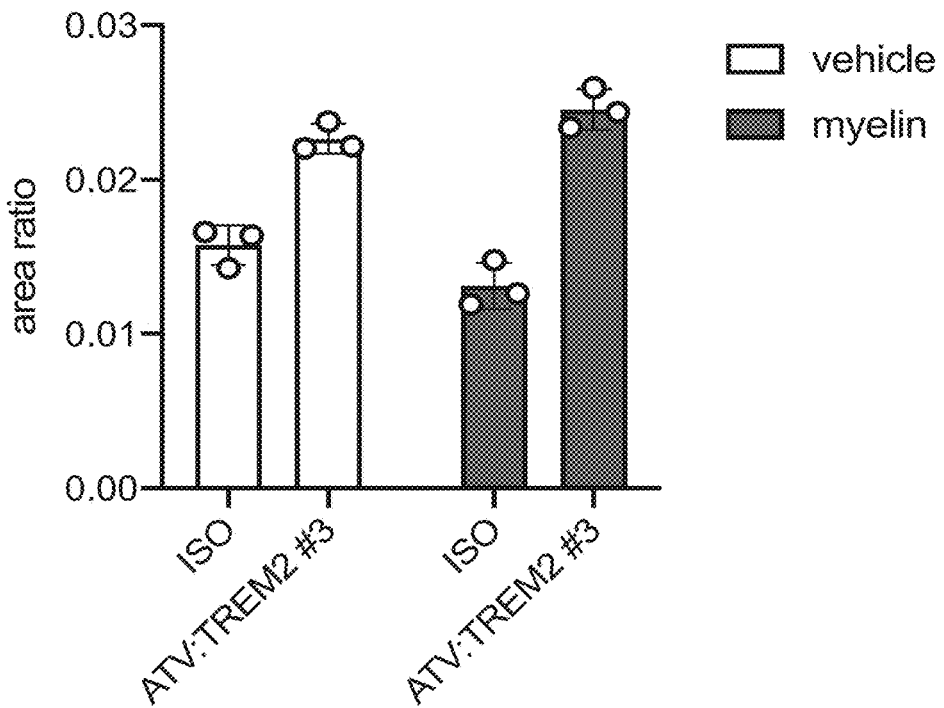
Figure 5F:
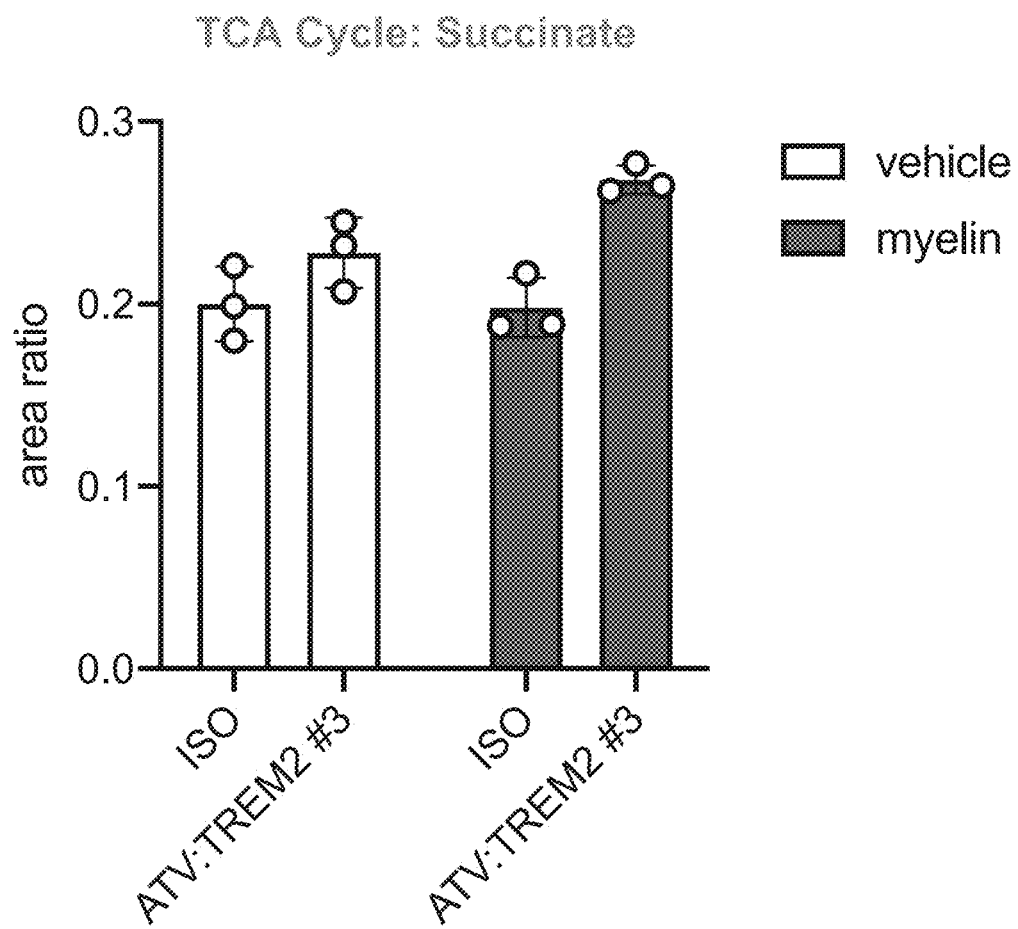
Figure 6B:
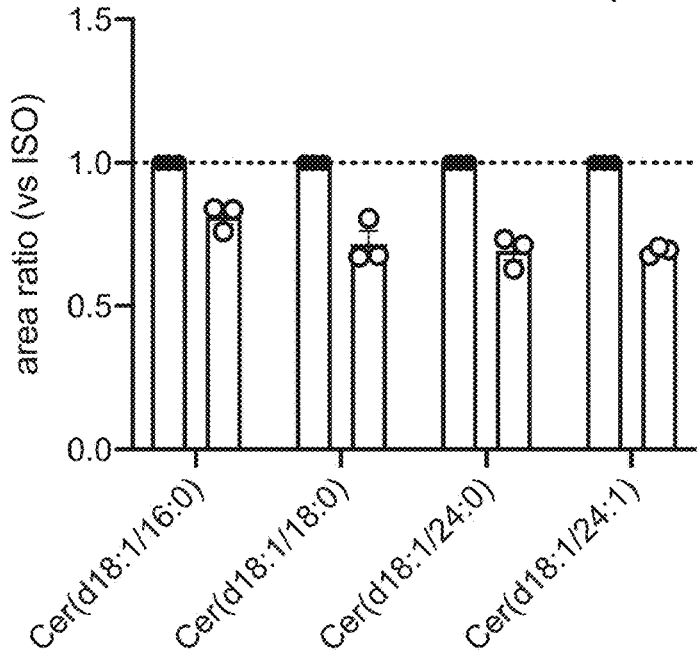
Figure 6C:
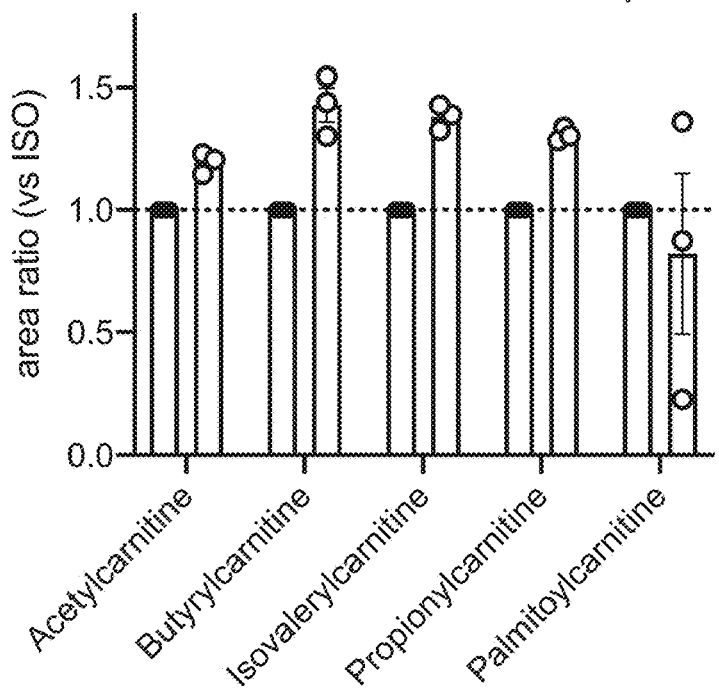

Additional studies were carried out to investigate the ability of ATV:TREM2 to reduce lipid accumulation. FIGS. 5A-5F and FIGS. 6A-6C show that a representative ATV:TREM2 variant (ATV:TREM2 #3) reduces lipid accumulation while enhancing fatty acid oxidation intermediates, suggesting a potential role of ATV:TREM2 in enhancing mitochondrial function. Cells (iMG) treated with oleic acid lipid challenge (33 μM) followed by incubation with ATV:TREM2 were able to reduce lipid accumulation, as illustrated by Bodipy staining (FIGS. 5A and 5B). LCMS analysis of iMG treated with myelin for 24 hours, followed by incubation with ATV:TREM2 for 48 hours, indicated that ATV:TREM2 reduces triglyceride (TG) species while concomitantly increasing beta-oxidation intermediates (acyl carnitines) and TCA cycle intermediates (FIGS. 5C-5F). FIG. 5C provides a heat map showing all TG, acyl carnitine, and TCA cycle intermediate species that illustrated a fold change of >1.5 (p<0.05), while FIGS. 5D-5F illustrate the changes of representative species in vehicle and myelin-challenged iMG that were incubated with ATV:TREM2 or isotype control following challenge. FIGS. 6A-6C illustrate the changes of specific TG, acyl carnitine, and TCA cycle intermediate species in iMG incubated with ATV:TREM2 or isotype control following myelin challenge. As depicted in FIGS. 6A-6C, ATV:TREM2 reduces all species of TG and ceramides while increasing certain species of short chain acyl carnitines, indicating that ATV:TREM2 may enhance mitochondrial function.

Figure 7A:
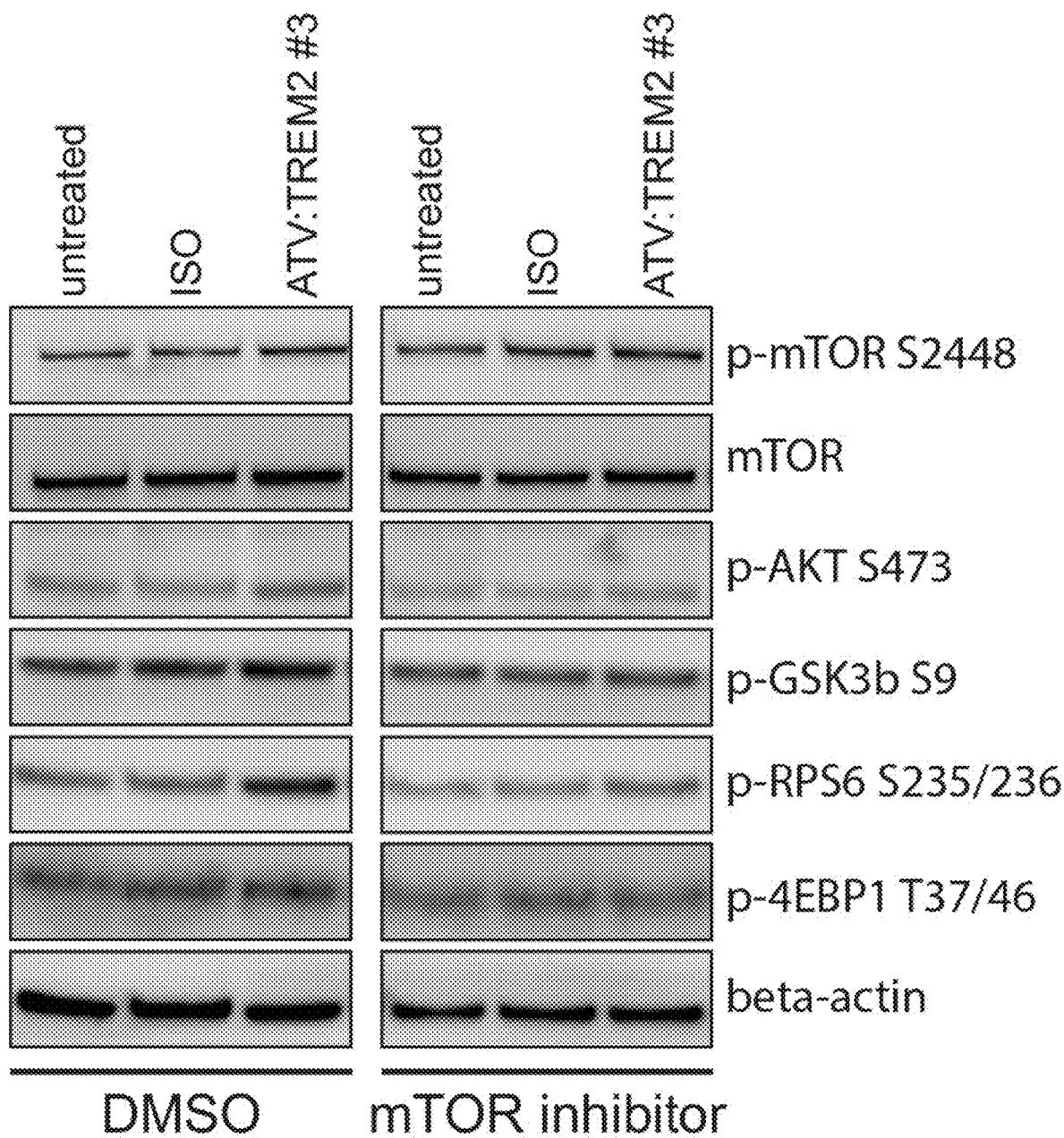
FIG. 7A includes representative images from a Western blot of mTOR signal pathway targets in iPSC-derived microglia treated with ATV:TREM2.
Figure 7B:
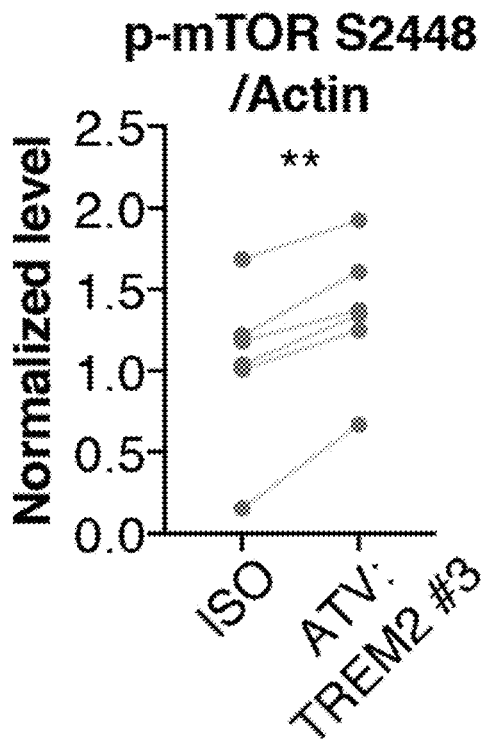
FIGS. 7B-7E include plots illustrating the change in levels of mTOR signal pathway targets in iPSC-derived microglia treated with ATV:TREM2.
Figure 7C:
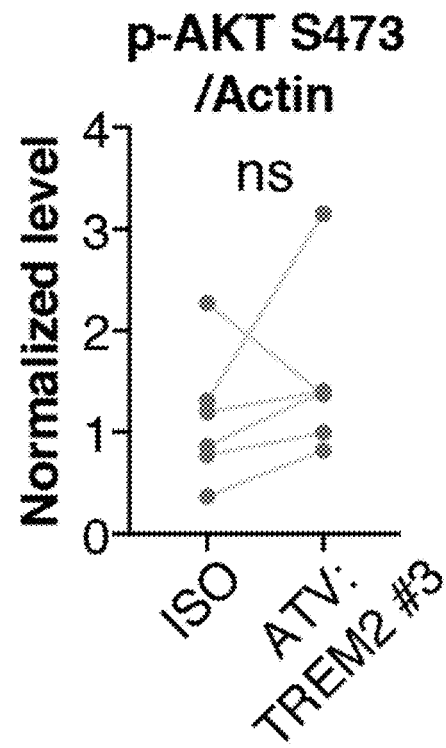
Figure 7D:
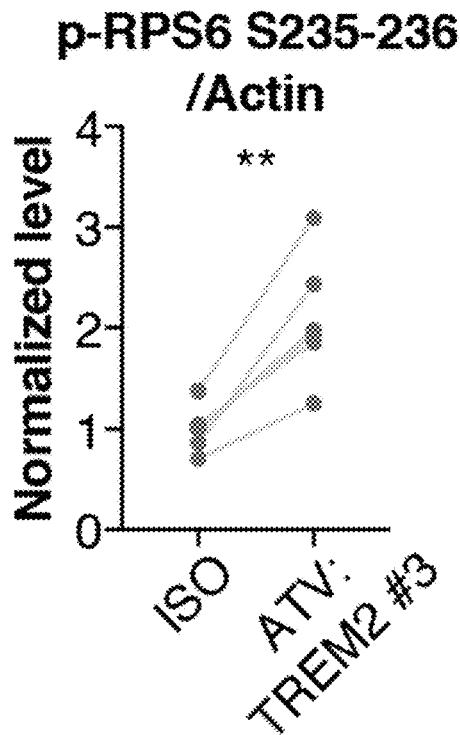
Figure 7E:
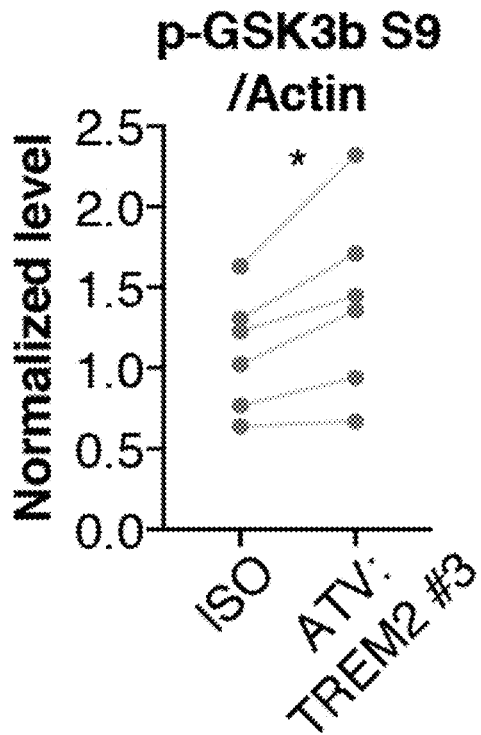

Microglial cell proliferation is associated with mTOR signal activation and engagement. The role of ATV:TREM2 in downstream mTOR pathway signaling was thus explored. The phosphorylation status of mTOR signal pathway targets were analyzed by Western blot in wild-type iPSC microglia incubated with a representative ATV:TREM2 variant (ATV:TREM2 #3) in the presence and absence of an mTOR inhibitor. FIG. 7A illustrates representative Western blot images of mTOR signal pathway targets. Quantification of Western blot data is provided in FIGS. 7B-7E (phosphorylation levels normalized to beta-actin loading control). Phosphorylation levels for each ATV:TREM2-treated sample were compared to isotype antibody control-treated samples for each independent experiment (n=6). The results show that ATV:TREM2 activates mTOR pathway signaling, as evidenced by increased phosphorylation levels of mTOR at serine$^{2488}$, AKT at serine$^{473}$, ribosomal protein S6 (RPS6) at serine$^{235/236}$, and GSK3b at serine$^9$ in ATV:TREM2-treated samples relative to isotype controls (FIGS. 7B-7E; statistical summary:"ns" (p>0.05); "*" (p<0.01); "**" (p<0.001)). RPS6 is a signal target that is downstream of mTORC1 complex, and GSK3b is a signal target that is downstream of mTORC2 complex. For all data generated in FIGS. 5A to 7E, the isotype control ("ISO") for ATV:TREM2 #3 contains the sequences provided in Table 5.

Example 6. ATV:TREM2 Role in Lysosomal Dysfunction

The role of ATV:TREM2 in lysosomal function was investigated. To assess impact on lysosomal function, levels of progranulin (PGRN) and bis(monoacylglycero)phosphates (BMPs) were measured in iPSC-derived microglial cells ("iMG") treated with an ATV:TREM2 variant.

To evaluate the effect of ATV:TREM2 on PGRN levels, iMG were plated at a density of 30,000 cells per well in a 96-well plate, and incubated with ATV:TREM2 #3 (100 nM) for 72 hours, after which the cell supernatant and cell lysate were collected and analyzed for progranulin (PGRN) levels using a colorimetric sandwich ELISA.

Figure 8:
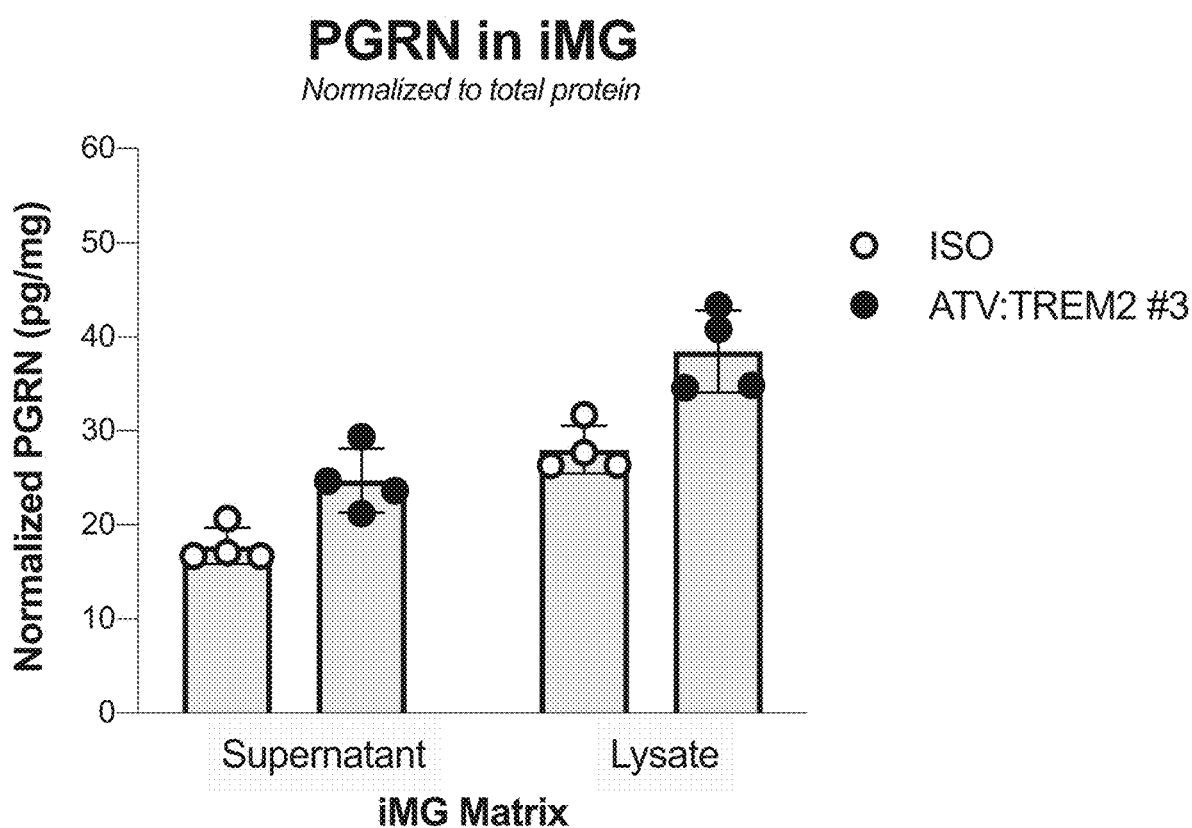
FIG. 8 is a bar graph illustrating the change in levels of progranulin (PGRN) in iPSC-derived microglia treated with ATV:TREM2.

For measurement of PGRN levels, Thermo Scientific 384-well Maxisorp plates were coated with 4 µg/mL capture antibody (R&D anti-PGRN antibody from DuoSet ELISA kit, Catalog No. DY2420) diluted in phosphate-buffered saline (PBS) and incubated overnight at 4° C. The sample wells were blocked for 90 minutes with 3% BSA in PBS. Cell samples were diluted 1:10 in 3% BSA in PBS and added to each sample well on the plate, followed by incubation for 90 minutes at room temperature. Detection antibody (R&D anti-PGRN antibody from DuoSet ELISA kit, Catalog No. DY2420) diluted to 125 ng/mL was subsequently added to each sample well, and the plate was incubated for 90 minutes at room temperature. Lastly, HRP-conjugated Streptavidin (R&D SA-HRP from DuoSet ELISA kit, Catalog No. DY2420) was diluted 1:200 and added to each sample well. The plate was incubated for 20 minutes at room temperature. After washing the sample wells with PBS, development reagent (TMB substrate) was added and allowed to react for 5 minutes before the reaction was stopped with 4 N $H_2SO_4$. Absorbance was measured using a BioTek Synergy Neo2 plate reader, and PGRN levels were determined by interpolation from the standard curve fit with a four-parameter logistic curve. As illustrated in FIG. 8, incubation with ATV:TREM2 increased PGRN levels in both the supernatant and cell lysate relative to isotype control.

Figure 9:
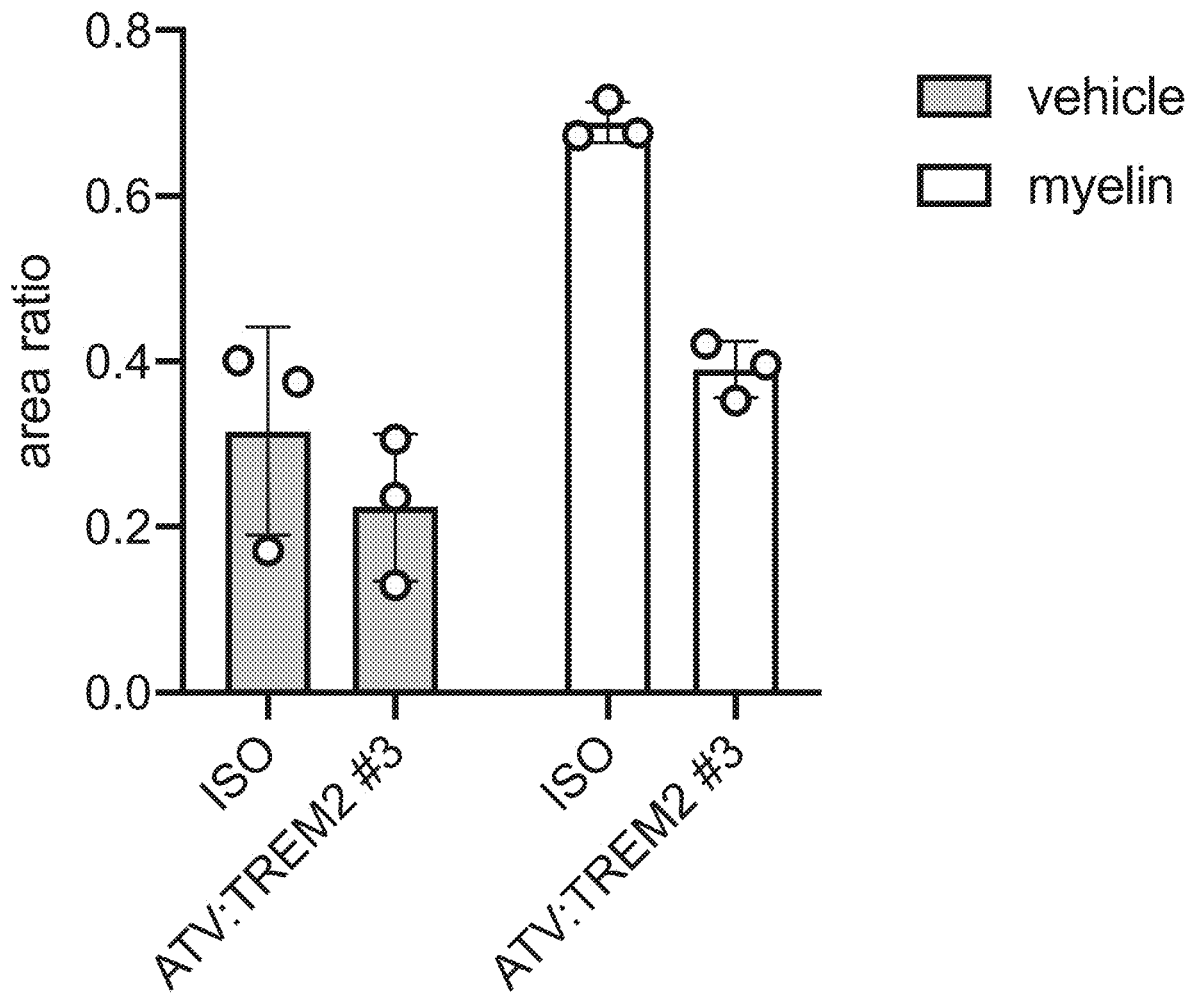
FIG. 9 is a bar graph illustrating the change in levels of a representative bis(monoacylglycero)phosphate (BMP) species in iPSC-derived microglia treated with ATV: TREM2.

To assess effect on BMP levels, iMG were challenged with myelin or vehicle for 24 hours, followed by incubation with ATV:TREM2 #3 (100 nM) for 48 hours. Cellular lipids were extracted via addition of methanol containing an internal standard mixture and BMP abundance was measured by liquid chromatography-mass spectrometry (LC-MS/MS) on a Q-trap 6500 (SCIEX) similar to that described in International PCT Publication No. WO 2020/112889. BMP species were quantified using BMP(14:0_14:0) as the internal standard and identified based on their retention times and MRM properties. Quantification was performed using Multi Quant 3.02 (Sciex) after correction for isotopic overlap. BMP species were normalized to median lipid content of all species measured. Protein concentration was measured using the bicinchoninic acid (BCA) assay (Pierce, Rockford, Ill., USA). A representative BMP result is illustrated in FIG. 9. As shown in FIG. 9, iMG challenged with myelin and subsequently treated with ATV:TREM2 reduces levels of BMP species, suggesting potential rescue of lysosomal challenge induced by myelin.

As illustrated in FIGS. 8 and 9, incubation of iMG with ATV:TREM2 increases PGRN levels and corrects myelin-induced BMP levels, indicating a role for ATV:TREM2 in modulating lysosomal effects. In FIGS. 8 and 9, the isotype control (ISO) for ATV:TREM2 #3 contains the sequences provided in Table 5.

Example 7. ATV:TREM2 Role in Mitochondrial Respiration

To assess impact on mitochondrial respiration, oxygen consumption was measured in iPSC-derived microglial cells ("iMG") treated with an ATV:TREM2 variant or isotype control using a Seahorse XFe96 analyzer (Agilent) and using materials and protocol from the Seahorse XF Palmitate Oxidation Stress Kit (Agilent 103693). Cells were cultured on XF96 microplates (Agilent, Cat. No. 102416) with ATV:TREM2 #3 (100 nM) or isotype control for 72 hours prior to the Seahorse experiment. Cells were subjected to substrate-limiting media composed of Seahorse XF RPMI (Agilent 103576) supplemented with 0.5 mM glucose (Agilent 103577), 1 mM glutamine (Agilent 103579), 0.5 mM L-carnitine (part of the Seahorse XF Palmitate Oxidation Stress Kit), and 1% Hyclone FBS 16 hours prior to Seahorse experiment. Cells were dosed with either palmitate-BSA conjugate (166 µM) or BSA control immediately before the experiment. Sequential injection of (1) etomoxir (4 µM) (carnitine palmitoyltransferase 1 (CPT1) inhibitor) or vehicle, (2) oligomycin (1.5 µM) (ATP synthase complex V inhibitor), (3) Carbonyl cyanide 4-(trifluoromethoxy)phenylhydrazone (FCCP, a mitochondrial decoupling agent, 1 µM), and (4) rotenone/antimycin (0.5 mM each, complex I and complex III inhibitors, respectively) were used to evaluate the mitochondrial respiration capacity of the cells. Oxygen consumption rate was measured during the course of the experiment by Seahorse analyzer (Agilent). A summary of experimental conditions for evaluating mitochondrial respiration is provided in Table 4.

TABLE 4

Experimental Conditions

| Condition | Antibody | CPT1 Inhibitor | Recovery substrate |
|---|---|---|---|
| 1 | Isotype Control | Etoxomir | BSA (control) |
| 2 | ATV:TREM2 | Vehicle | BSA (control)) |
| 3 | Isotype Control | Etoxomir | Palmitic acid (PAL) |
| 4 | ATV:TREM2 | Vehicle | Palmitic acid (PAL) |
| 5 | Isotype Control | Etoxomir | BSA (control) |
| 6 | ATV:TREM2 | Vehicle | BSA (control)) |
| 7 | Isotype Control | Etoxomir | Palmitic acid (PAL) |
| 8 | ATV:TREM2 | Vehicle | Palmitic acid (PAL) |

Figure 10A:
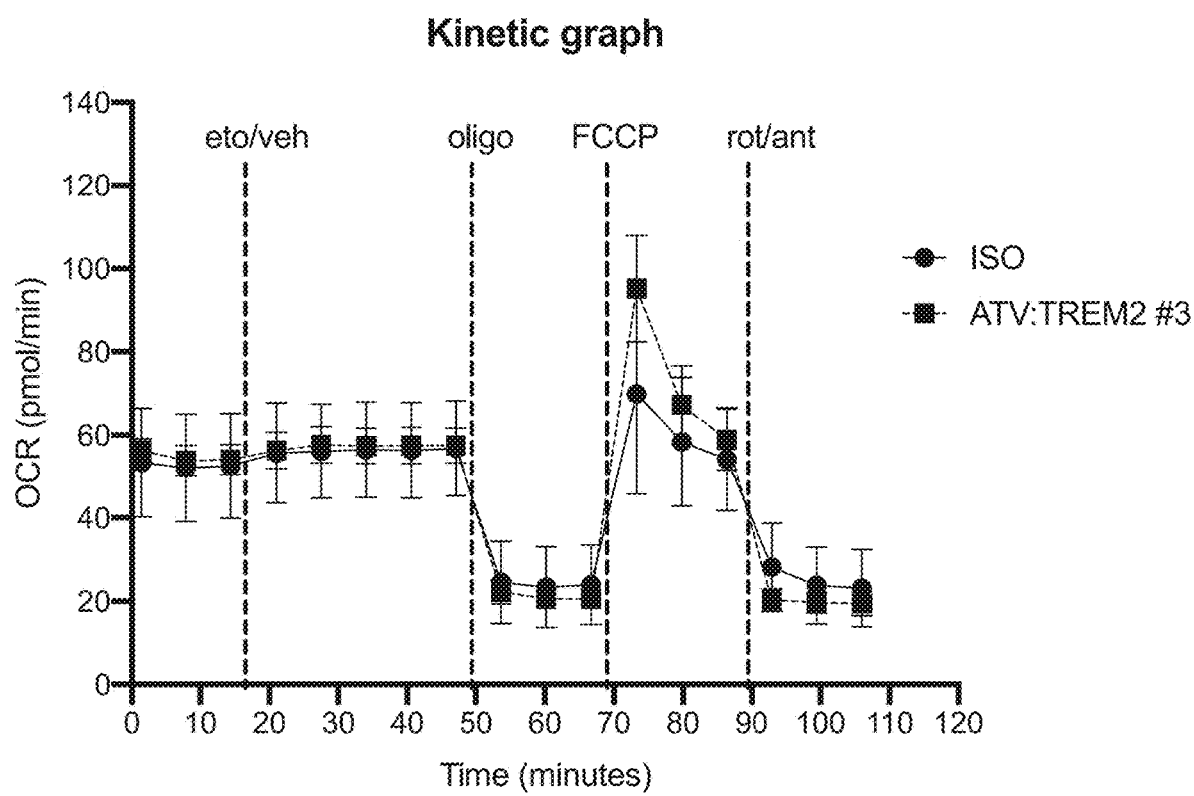
FIG. 10A is a representative kinetic graph of oxygen consumption in iPSC-derived microglial cells treated with ATV:TREM2.
Figure 10B:
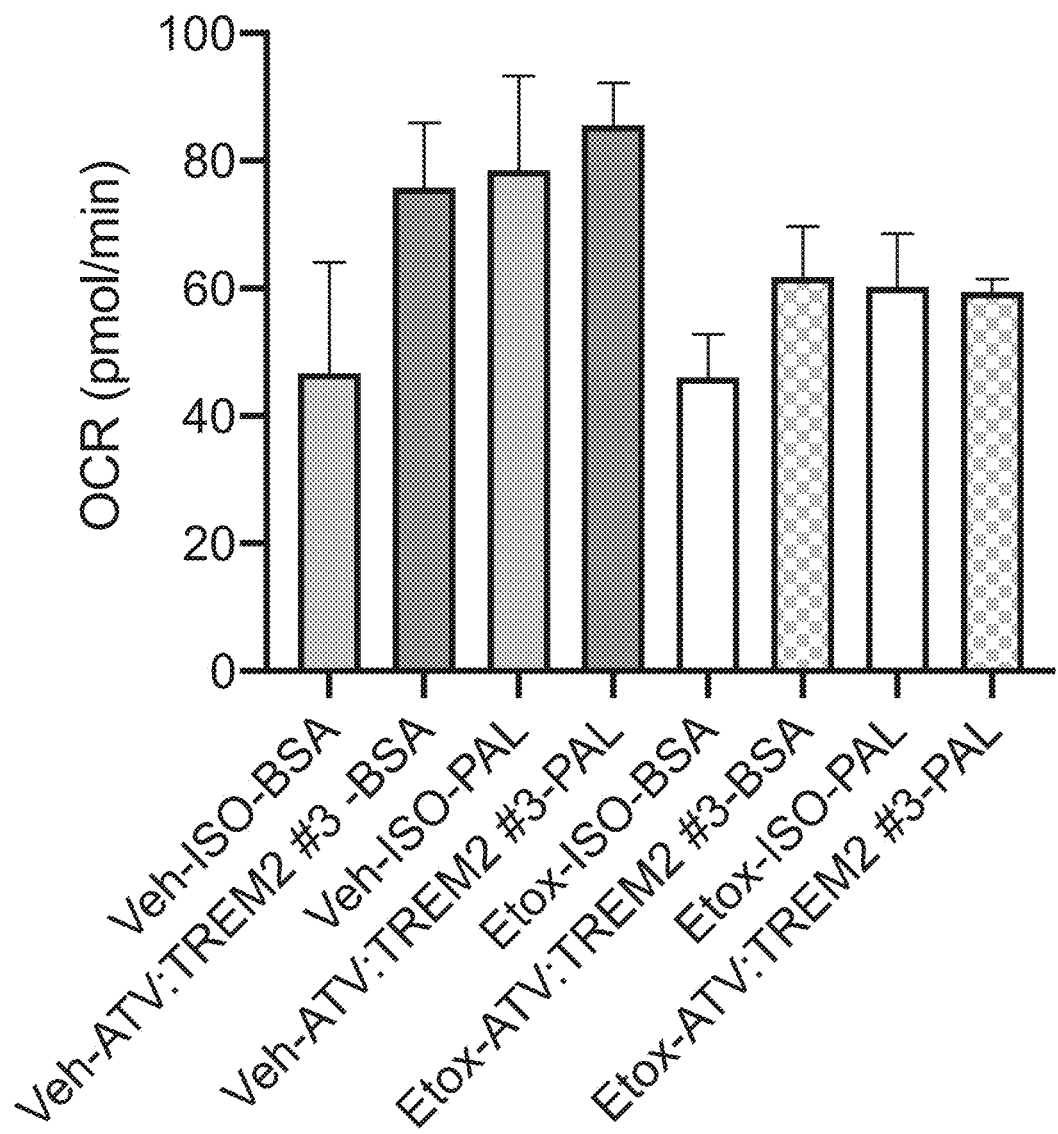
FIG. 10B is a bar graph illustrating the maximal respiratory capacity of iPSC-derived microglial cells treated with ATV:TREM2 in the presence and absence of a CPT1 inhibitor.

A representative kinetic graph of oxygen consumption is illustrated in FIG. 10A, and a bar graph illustrating the maximal respiratory capacity of the cells is provided in FIG. 10B. As shown in the figures, ATV:TREM2 increases maximal respiration to an extent similar to that of fatty acid substrate palmitic acid (PAL). This effect is diminished in the presence of CPT1 inhibitor. The results indicate that ATV:TREM2 enhances maximal mitochondrial respiration and that this effect appears to be conferred by enhanced fatty acid oxidation capacity.

Example 8. ATV:TREM2 Comparative Properties

The properties of ATV:TREM2 #1 and ATV:TREM2 #3 were compared to those of reference antibodies that bind TREM2, which are described in WO 2019/028292. The heavy chain and light chain sequences of reference antibody #1 ("Ref. Ab. #1") are represented by SEQ ID NOs:74 and 75, respectively. The heavy chain and light chain sequences of reference antibody #2 ("Ref. Ab. #2") are represented by SEQ ID NOs:76 and 75, respectively. Heavy and light chain sequences for the isotype controls of each anti-TREM2 antibody are provided in Table 5.

TABLE 5

Isotype Control Sequences

| Isotype Control | First Heavy Chain | Second Heavy Chain | Light Chain |
|---|---|---|---|
| ISO for reference antibody #1 and #2 | SEQ ID NO: 77 | SEQ ID NO: 77 | SEQ ID NO: 78 |
| ISO for ATV:TREM2 #1 | SEQ ID NO: 79 | SEQ ID NO: 81 | SEQ ID NO: 82 |
| ISO for ATV:TREM2 #3 | SEQ ID NO: 80 | SEQ ID NO: 81 | SEQ ID NO: 82 |

Figure 11B:
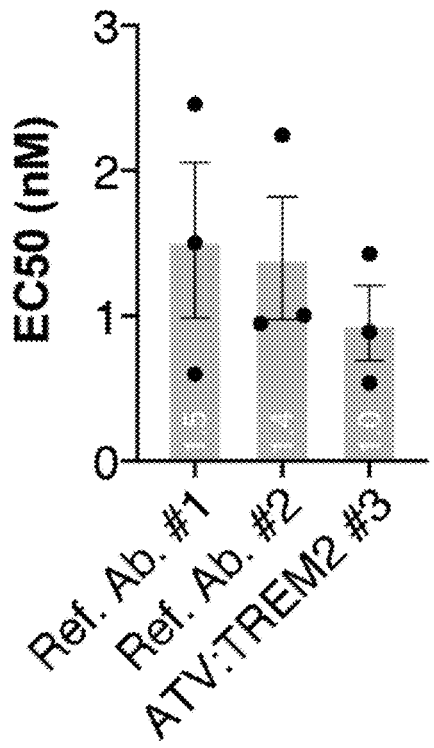
FIGS. 11B and 11C include bar graphs illustrating EC50 and Emax for the dose-response curves in FIG. 11A.

ATV:TREM2 is More Potent In Vitro and Induces Less Inflammation (Less Cytokine Release) than Reference Abs Anti-TREM2 antibodies were evaluated using the human macrophage cell survival assay described in Example 4. FIG. 11A illustrates cell viability dose-response curves with the anti-TREM2 antibodies, with "ISO" referring to the isotype control for ATV:TREM2 #3 (Table 5). Corresponding potency (EC50) and maximum response (Emax) values as determined from the dose-response curves are provided in FIGS. 11B and 11C; individual marks represent single values from human cell donors (n=3). The results provided in FIGS. 11A-11C indicate that ATV:TREM2 #3 is more potent in promoting human macrophage survival in vitro than reference antibodies #1 and #2.

Figure 12:
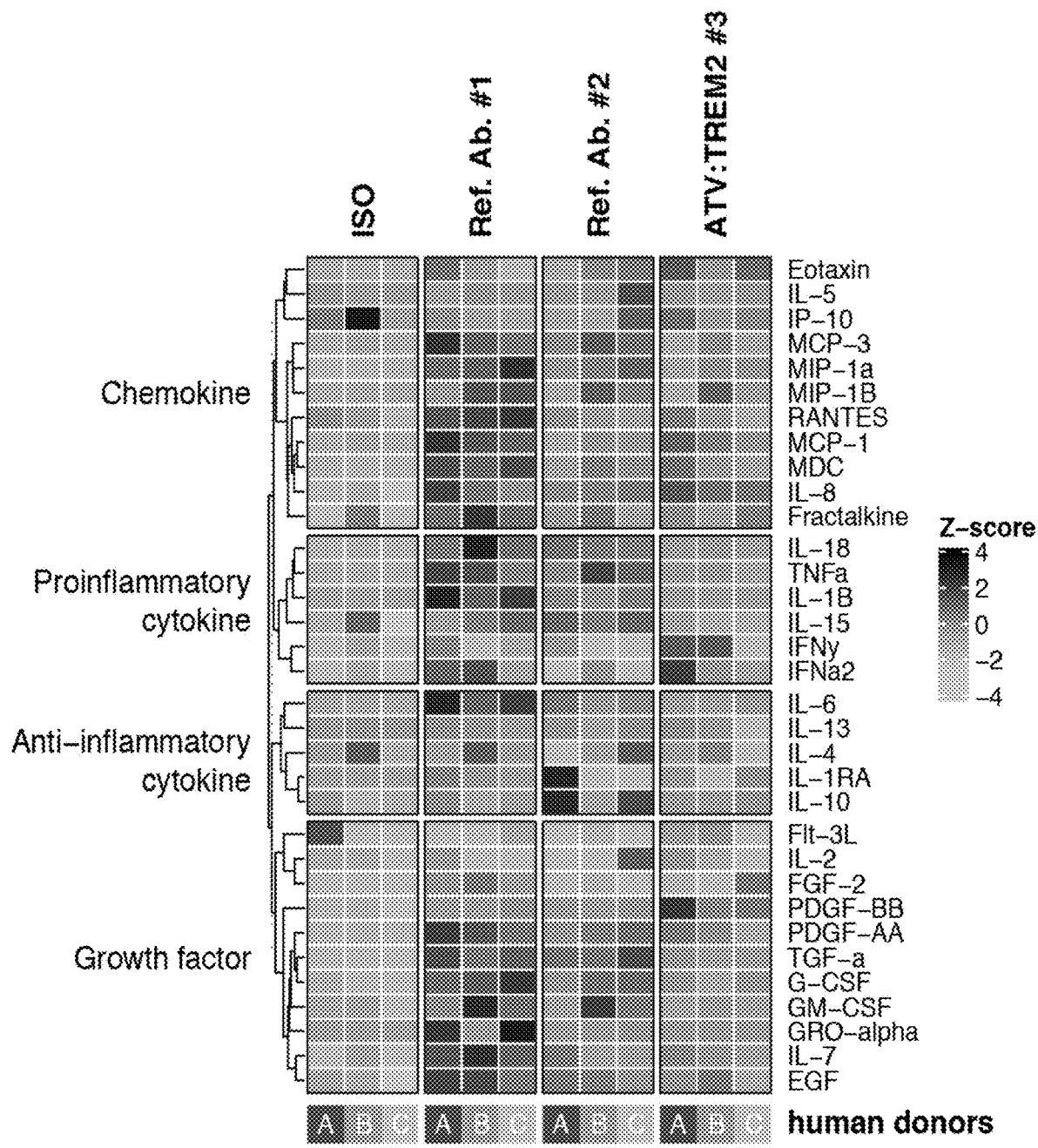
FIG. 12 is a heat map of relative cytokine release in human macrophage cells treated with anti-TREM2 antibodies.

In a separate experiment, human macrophage cells were treated with 100 nM of surface-immobilized anti-TREM2 antibodies for five days, after which cell culture media for each set of cells was collected and analyzed for cytokine release using Luminex xMAP technology and a commercial bead-based multiplex assay kit (Human Cytokine 42-Plex Discovery Assay®, Eve Technologies Corp.). A heat map of relative cytokine release level is illustrated in FIG. 12 (Z-score used for plotting). The results in FIG. 12 illustrates that ATV:TREM2 #3 induces less inflammation in human macrophage cells than reference antibodies #1 and #2.

Figure 11C:
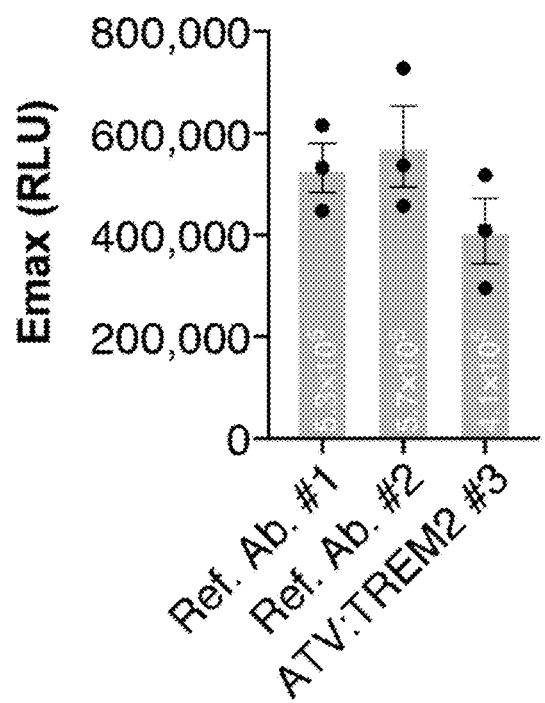

In summary, ATV:TREM2 #3, reference antibody #1, and reference antibody #2 are able to promote human macrophage survival and proliferation (FIG. 11A). However, ATV: TREM2#3 shows stronger potency for cell survival with reduced overall cytokine signature relative to reference antibodies #1 and #2 (FIGS. 11B, 11C, and 12).

ATV:TREM2 is Able to Reduce Triglyceride Species Levels after Challenge

Anti-TREM2 antibodies were evaluated by lipid storage assay (using 10 µM oleic acid challenge) as described in Example 4. The results for ATV:TREM2 #3, reference antibody #1, and reference antibody #2 are provided in FIGS. 13A-13E.

Figure 13A:
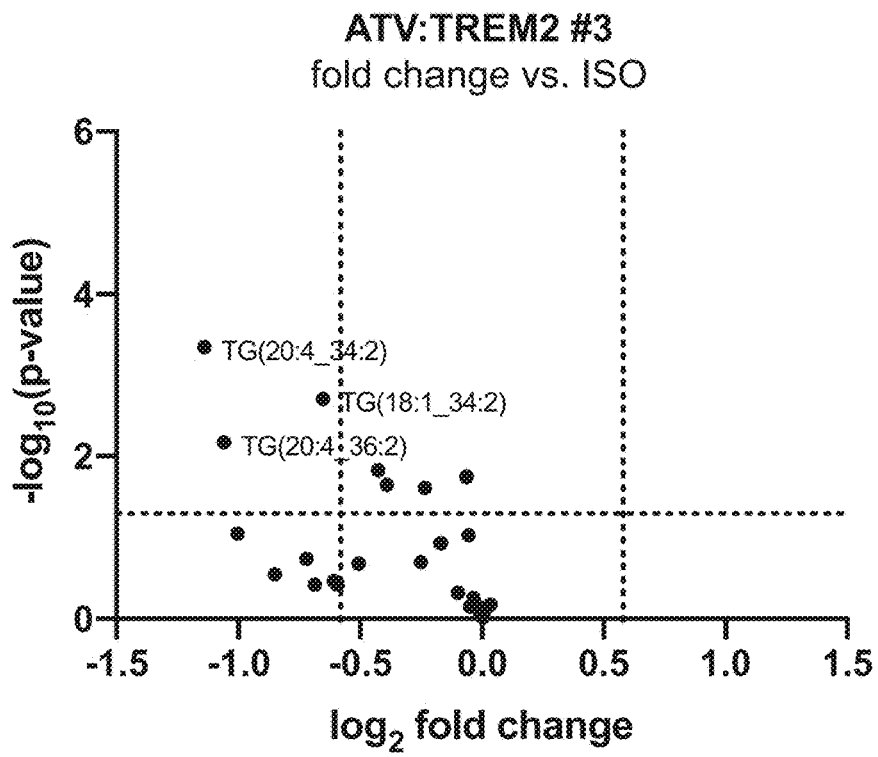
Figure 13B:
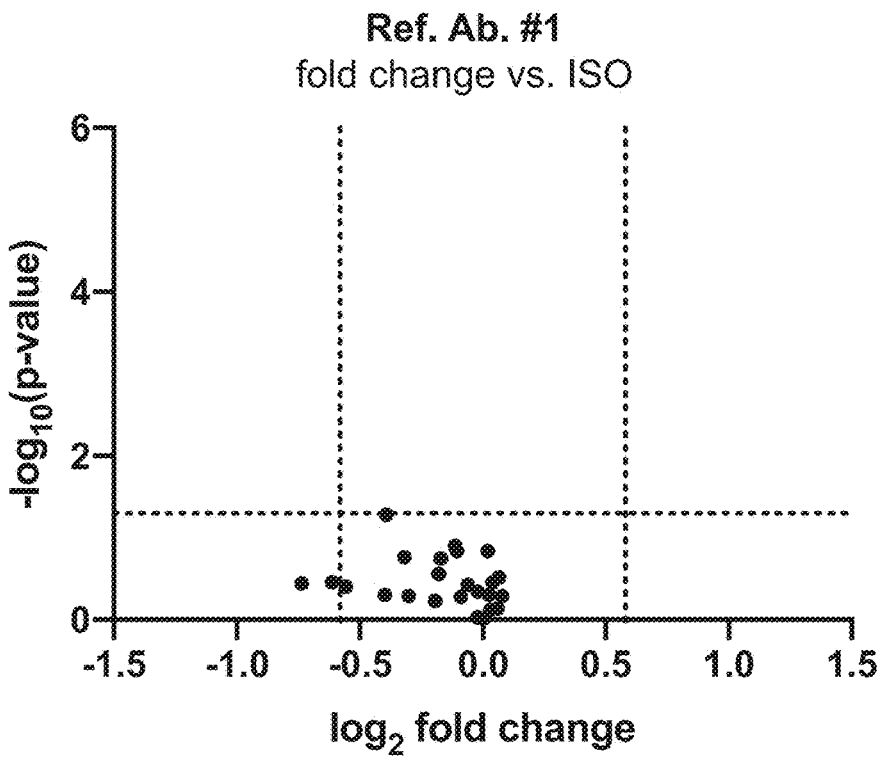
Figure 13D:
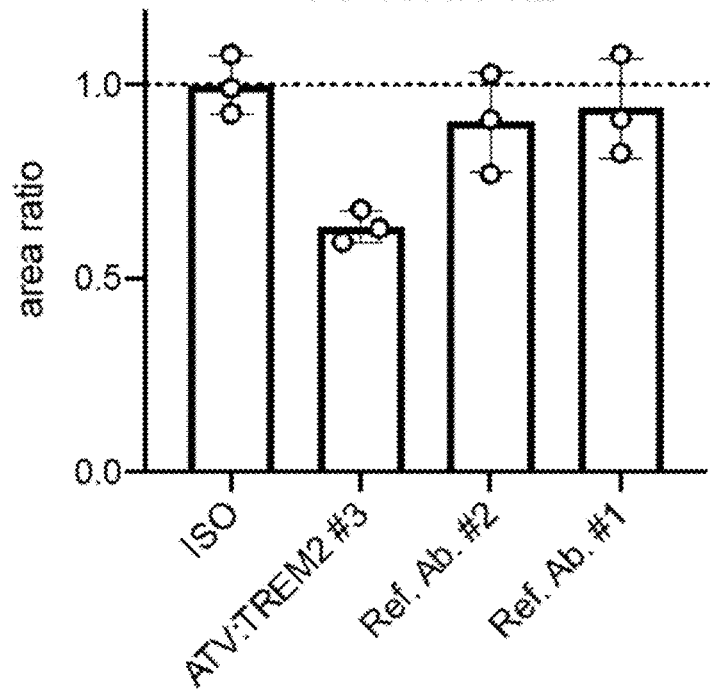
FIGS. 13D and 13E include bar graphs showing the change in levels of representative triglyceride species in iPSC-derived microglial cells treated with anti-TREM2 antibodies.
Figure 13E:
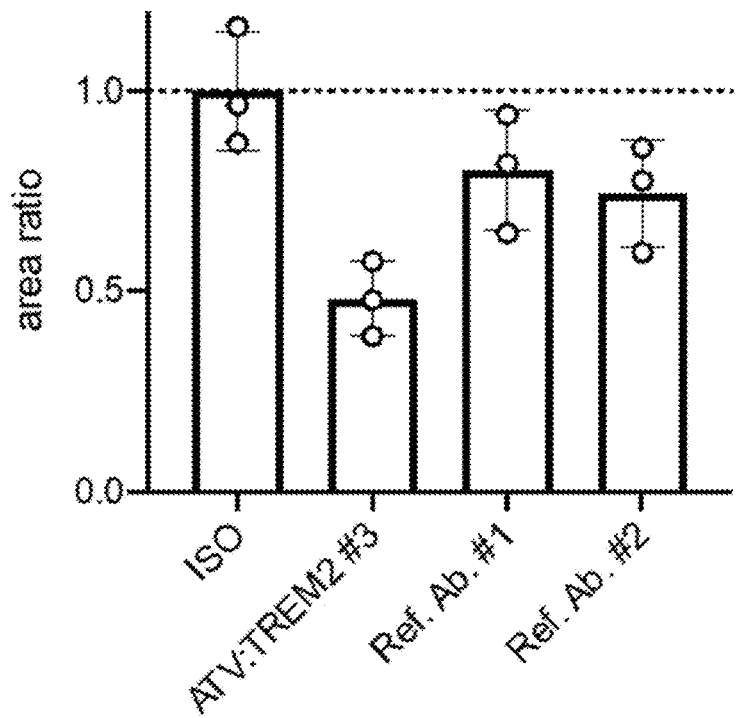

FIGS. 13A-13C illustrate volcano plots with cut-offs of p<0.05 and fold change >1.5 for triglyceride species in iPSC-derived microglial cells ("iMG") as quantified by LCMS. The data is normalized to the isotype control for each antibody. As shown in FIGS. 13A-13C, ATV:TREM2 #3 is able to modulate triglyceride (TG) species post-oleic acid dosing, while the reference antibodies did not significantly change levels of TG species after oleic acid challenge. FIGS. 13D and 13E illustrate bar graphs of representative TG species measurement, with data normalized to isotype control for ATV:TREM2 #3.

ATV:TREM2 is Able Modulate TREM2 Levels In Vitro

To assess how anti-TREM2 antibodies impact TREM2 levels in iPSC-derived microglial cells ("iMG"), iMG were incubated with ATV:TREM2 #3 or reference antibody #1 for 72 hours at various concentrations, followed by measurement of TREM2 levels in iMG cell lysate and cell culture medium. TREM2 was measured as follows. Briefly, MSD small spot streptavidin plates (Meso Scale Discovery) were coated with biotinylated goat anti-hTREM2 polyclonal antibody (R&D Systems, BAF1828) at room temperature for 1 hour. The plates were then blocked with MSD Block A buffer (Meso Scale Discovery) for 1 hour at room temperature. Samples and standards were prepared/diluted with assay buffer (25% MSD Block A buffer in TBST), and 30 µL of samples and standards was loaded into the plate after blocking. After 1 hour of incubation at room temperature, the plates were washed with TBST and followed by binding the primary antibody (ATV:TREM2 #3) for 1-hour at room temperature. Afterwards, diluted sulfo-tagged goat anti-human IgG (Southern Biotech, 2049-01) was added to the plates, and incubated for one hour at room temperature. After washing with TBST, the MSD plates were developed using 2×MSD read buffer T, followed by detection using an MSD Sector plate reader. MSD values were converted to absolute quantities of TREM2 by fitting a standard curve using Meso Scale Discovery software (Discovery Workbench).

Figure 14A:
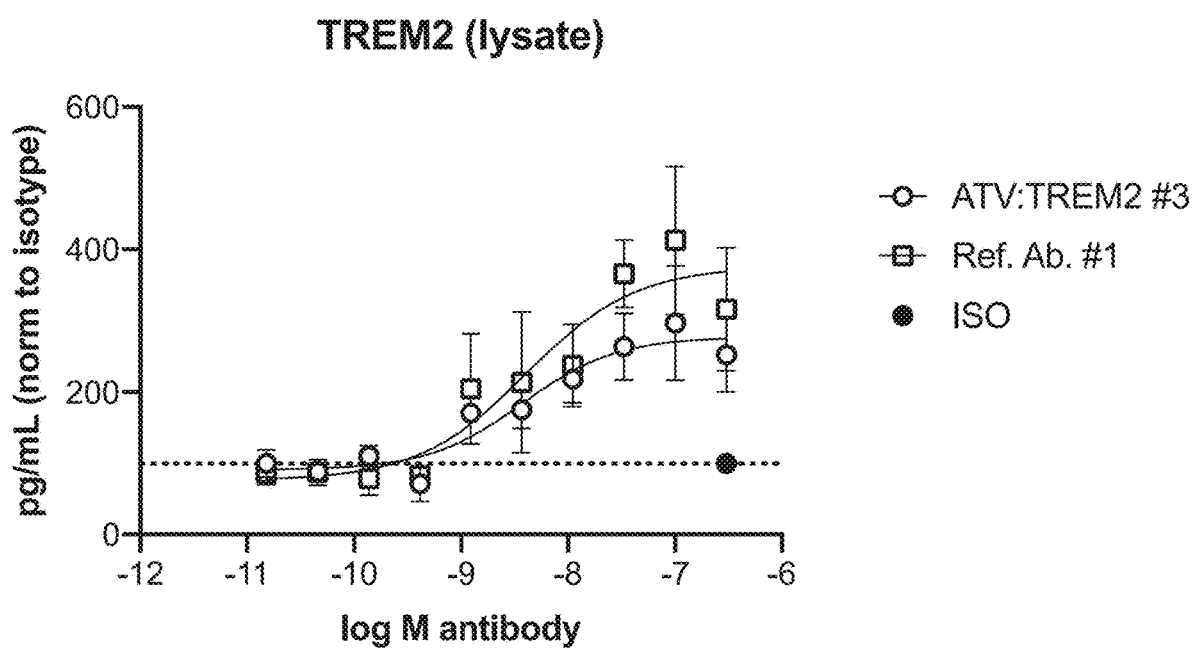
FIG. 14A is a plot of TREM2 level as a function of antibody concentration in the cell lysate of iPSC-derived microglial cells treated with anti-TREM2 antibodies.
Figure 14B:
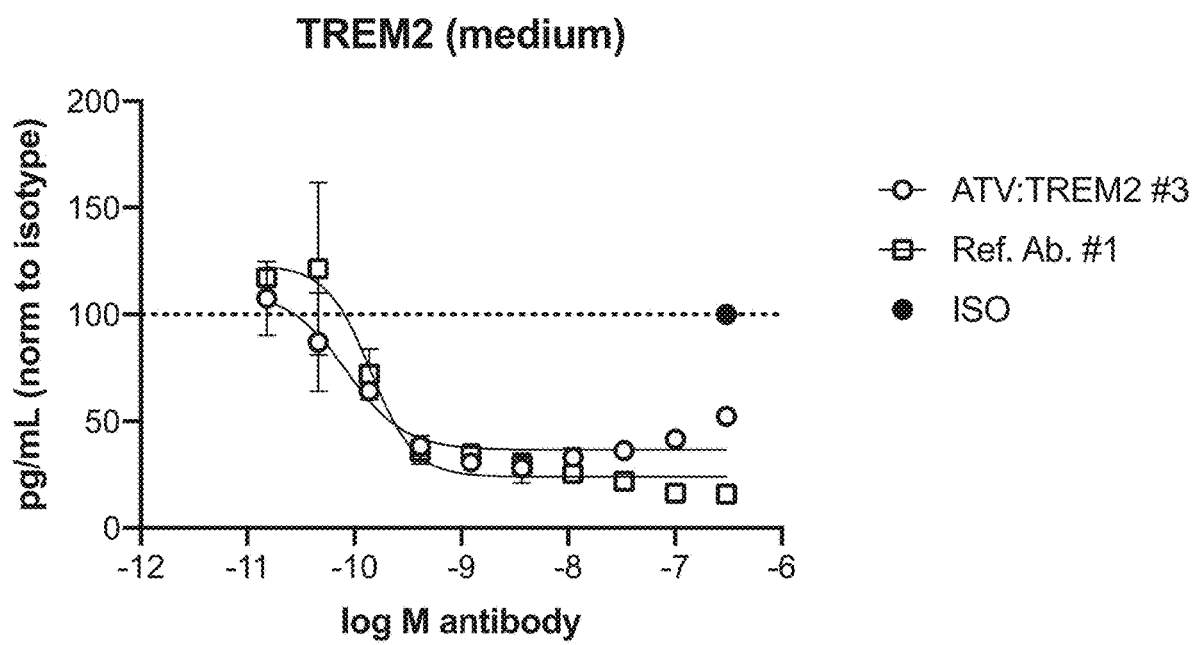
FIG. 14B is a plot of TREM2 level as a function of antibody concentration in the cell culture media of iPSC-derived microglial cells treated with anti-TREM2 antibodies.

FIGS. 14A and 14B show plots of TREM2 levels as a function of antibody concentration in iMG cell lysates and cell culture media after incubation with anti-TREM2 antibodies. TREM2 levels for each antibody are normalized to their specific isotype control. In FIGS. 14A and 14B, "ISO" represents isotype control for ATV:TREM2 #3. As illustrated in FIG. 14A, the levels of total TREM2 increased with increasing amounts of antibody in the cell lysates of iMG treated with ATV:TREM2 #3 and reference antibody #1. In contrast, the levels of soluble TREM2 decreased with increasing amounts of antibody in the cell culture media of the antibody-treated cells.

ATV:TREM2 Exhibits a Superior Pharmokinetic Profile in Non-Human Primates

The pharmacokinetic (PK) properties of anti-TREM2 antibodies were studied in non-human primates. Briefly, young adult/adult male cynomolgus monkeys ranging in age from 36 to 53 months were intravenously administered a single dose of 30 mg/kg test article (Table 6, n=5 per cohort). CSF samples were collected at 24, 168, and 336 hours post-dose.

Figure 15:
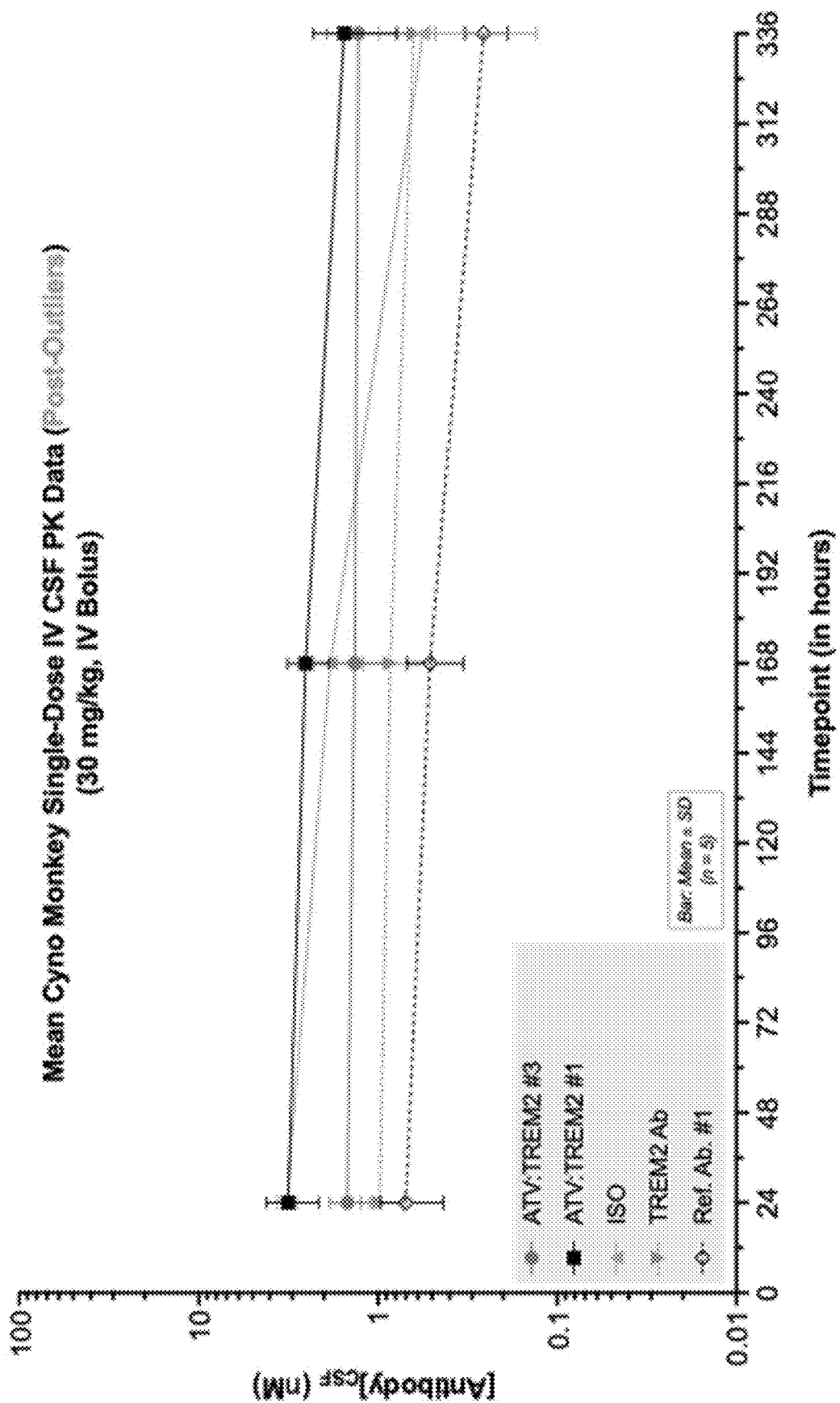
FIG. 15 is a plot illustrating the pharmacokinetic profile of anti-TREM2 antibodies dosed in cynomolgus monkeys.

The results are illustrated in Table 6 and FIG. 15. Table 6 shows the PK values of anti-TREM2 antibodies in the cerebrospinal fluid (CSF) of non-human primates. The PK values of ATV:TREM2 variants show that these antibodies have a higher exposure in CSF relative to TREM2 Ab (lacking binding capacity for transferrin receptor; heavy and light chain sequences represented by SEQ ID NOs: 83 and 54, respectively) and reference antibody #1.

TABLE 6

CSF pharmacokinetic profiles of anti-TREM2 antibodies in non-human primates

| Test Article | Dose (mg/kg) | $C_{max}$ (nM) | $T_{max}$ (hr) | $AUC_{0-last}$ (nM * hr) |
|---|---|---|---|---|
| ATV:TREM2 #1 | 30 | 3.17 | 24 | 822.59 |
| ATV:TREM2 #3 | 30 | 1.49 | 24 | 461.79 |
| ISO* | 30 | 3.23 | 24 | 618.90 |
| TREM2 Ab | 30 | 0.98 | 24 | 280.38 |
| Reference antibody #1 | 30 | 0.70 | 24 | 166.69 |

*Isotype control for ATV:TREM2 #1

FIG. 15 illustrates the PK profiles for anti-TREM2 antibodies in the CSF of dosed non-human primates. As illustrated in FIG. 15 and Table 6, ATV:TREM2 shows at least a 2-fold increase in CSF PK compared to reference antibody #1.

Example 9. ATV:TREM2 Properties in a Humanized TREM2 Mouse

To investigate the effects of ATV:TREM2 in vivo, we generated a BAC transgenic mouse that expresses human TREM2. These mice were crossed to a human transferrin receptor knock-in mouse described in U.S. Pat. No. 10,143,187 to allow for characterization of the ATV:TREM2 molecules described herein.

Generation of Human TREM2 BAC Transgenic Model

To investigate the effects of ATV:TREM2 in vivo, we generated several transgenic mouse lines expressing the human TREM2 by using modified BAC DNA CTD-2210D2 (ThermoFisher Scientific; Cat. No. 96012). In the original BAC DNA CTD-2210D2, the human TREM2 coding region and its regulatory elements are flanked by two other TREM-like genes, TREML1 and TREML2. To avoid interference from these TREM-like genes, we abolished their expression by deleting exon 1 from TREML1 and exon 3 from TREML2. This engineered BAC CTD-2210D2 DNA construct was injected into the pronucleus of fertilized mouse eggs from C57BL/6J mice. Two independent founder lines (termed TB36 and TB45) were obtained and were shown to have germline transmission.

To characterize and compare these two transgenic lines, hemizygous transgenic animals and wild type non-transgenic litter mate controls were used for analysis. Human TREM2 copy number was determined using qPCR analysis of tail genomic DNA. Human TREM2 mRNA and protein levels were measured in brains, liver, lung, and spleen by qRT-PCR and anMSD assay. Human TREML1 and TREML2 mRNA were analyzed in brain-sorted microglia by qRT-PCR. Surface TREM2 expression was quantified by FACS in bone marrow derived macrophages (BMDM). Human TREM2 function was assessed by the in vitro BMDM survival assay.

Human TREML1 and TREML2 were undetectable in either TB36 or TB45, showing successful deletion of these genes. qPCR analysis showed that there are two and one copies of human TREM2 transgenes in TB36 and TB45, respectively, with corresponding higher human TREM2 expression in TB36 relative to TB45 in brains and peripheral tissues. The in vitro survival assay showed that human TREM2 agonist antibodies trigger stronger responses in TB36 line than in TB45 line.

Based on this ex vivo and in vitro characterization, we selected TB36 for the following breeding and in vivo studies. The hemizygous TB36 mice were further backcrossed to C57BL/6J for three rounds and then bred with hTfR KI mice (described in U.S. Pat. No. 10,143,187) to generate human TREM2 BAC hemizygous; hTfR KI homozygous mice for in vivo studies.

Pharmacokinetics and Pharmacodynamics Responses with ATV:TREM2 in TB36/hTfR KI Mice To determine whether ATV:TREM2 can trigger microglia response in vivo, a single dose of ATV:TREM2 #3 or a corresponding isotype control (ATV:RSV) (100 mg/kg) was intravenously administered to TB36/hTfR KI mice at day 0, and mice were sacrificed at day 1 or day 4 post-dose for ex vivo analysis. At the time of sacrifice, animals were anesthetized by intraperitoneal injection of 2.5% Avertin. Terminal blood was collected through the cardiac puncture in an EDTA tube with slow inversion (10 times) and was then centrifuged at 15,350 g for 7 minutes at 4° C. Plasma (top layer) was transferred to a 1.5-ml Eppendorf tube and stored at −80° C. until measurement. After blood collection, CSF samples were collected by pre-pulled glass capillary tubes from the cisterna *magna* and then transferred to 0.5 mL Protein LoBind Eppendorf tubes for centrifugation at 12,700 rpm for 7 minutes at 4° C. The supernatants of CSF samples were snap frozen on dry ice and stored at −80° C. until measurement. The animals were then perfused with cold PBS, and brains were dissected out, and the two hemispheres were separated. Right hemi-brains were immersion fixed in 4% paraformaldehyde at 4° C. for 24 hours and then transferred to a phosphate buffered saline (PBS) solution with 0.1% sodium azide for storage until ready for 30% sucrose processing and sectioning. Left hemi-brains were cut into two pieces and snap frozen in two tubes for the PK measurement and other target engagement/cytokines analyses, respectively.

Plasma and brain levels of human IgG were evaluated at 1 day and 4 days post-dose and are shown in Table 7 below.

TABLE 7

Plasma and Brain pharmacokinetic profiles of in TB36/hTfR-KI mice

| TB36 * hTfR-KI | Plasma | | Brain | |
|---|---|---|---|---|
| | ATV:RSV [hIgG] uM | ATV:188-14 [hIgG] uM | ATV:RSV [hIgG] nM | ATV:188-14 [hIgG] nM |
| 24 hours | 2.96 ± 0.17 | 1.78 ± 0.073 | 34.1 ± 3.2 | 24.4 ± 1.6 |
| 96 hours | 0.401 ± 0.074 | 0.29 ± 0.013 | 13.8 ± 1.8 | 6.67 ± 1.0 |

Effect of ATV:TREM2 on Microglial Proliferation

Four doses of 5-Ethynyl-2'-deoxyuridine (EdU, 80 mg/kg), a thymidine analog that can be incorporated into newly synthesized DNA, were intraperitoneally administered to the mice at day 0, day 1, day 2 and day 3 after the treatment of ATV:TREM2 #3 or ATV:RSV at day 0.

Figure 16A:
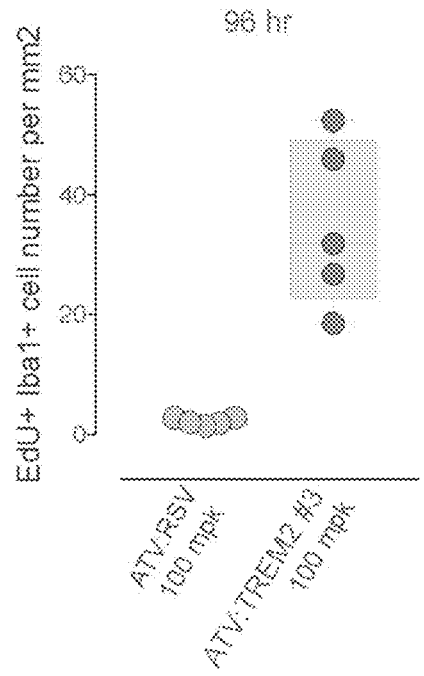
FIGS. 16A and 16B are plots showing EdU$^+$Iba$^+$ cells per mm$^2$ (FIG. 16A) and relative Iba$^+$ area (FIG. 16B) in brains of TB36/hTfR KI mice treated with either ATV:TREM2 or ATV:RSV.
Figure 16B:
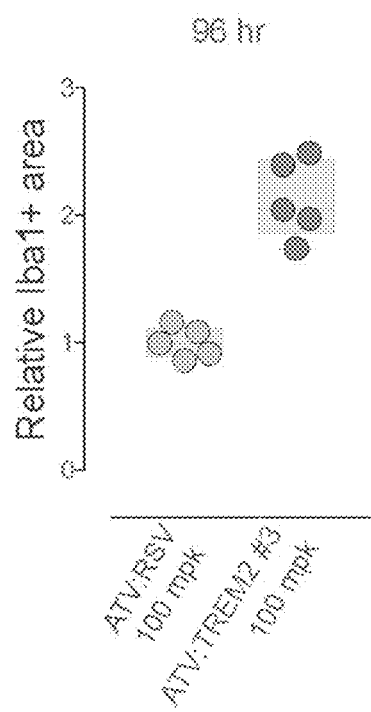

For detection of proliferating microglia (EdU+Iba1+), the brain sections at day 4 post-dose were treated with Click-iT EdU-imaging kits (ThermoFisher Scientific, C10637) followed by Iba1 immunostaining. EdU-Iba1 staining showed that ATV:TREM2 dramatically increases newborn microglia number (EdU+Iba1+; FIG. 16A) and total microglial coverage area (Iba1+area; FIG. 16B) in the brains compared to the isotype control, thus demonstrating that ATV:TREM2 significantly increases microglial proliferation as compared to the control.

Figure 17A:
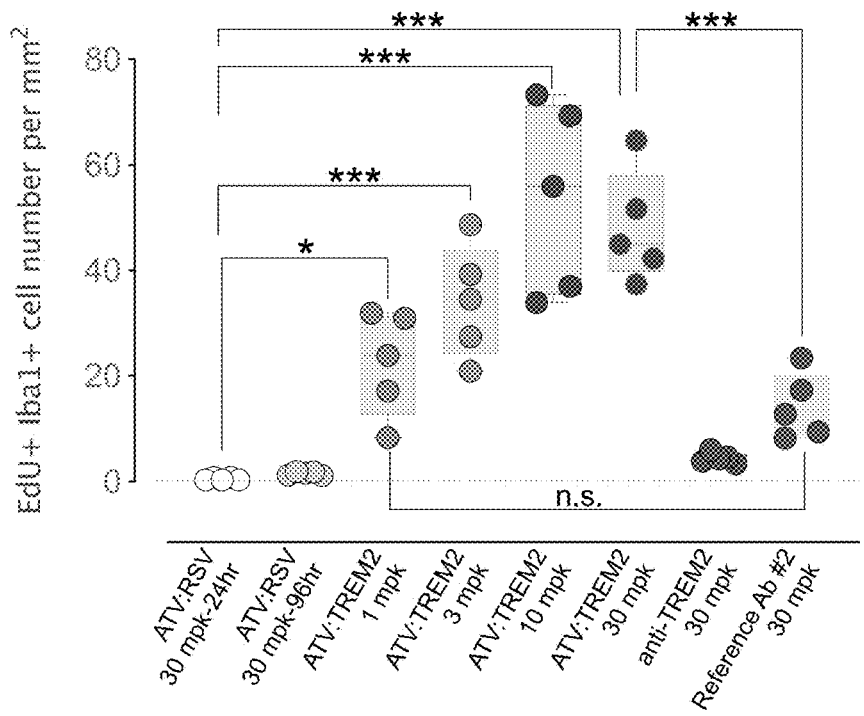
FIGS. 17A and 17B are plots showing EdU$^+$Iba$^+$ cells per mm$^2$ (FIG. 17A) and relative Iba$^+$ area (FIG. 17B) in brains of TB36/hTfR KI mice treated with either ATV:TREM2, a corresponding TREM2 antibody, reference antibody #2, or ATV:RSV. Graphs display mean±SEM and p values: one way ANOVA with Tukey's multiple comparison test; * p≤0.05,  p≤0.01, * p≤0.001, **** p≤0.0001.
Figure 17B:
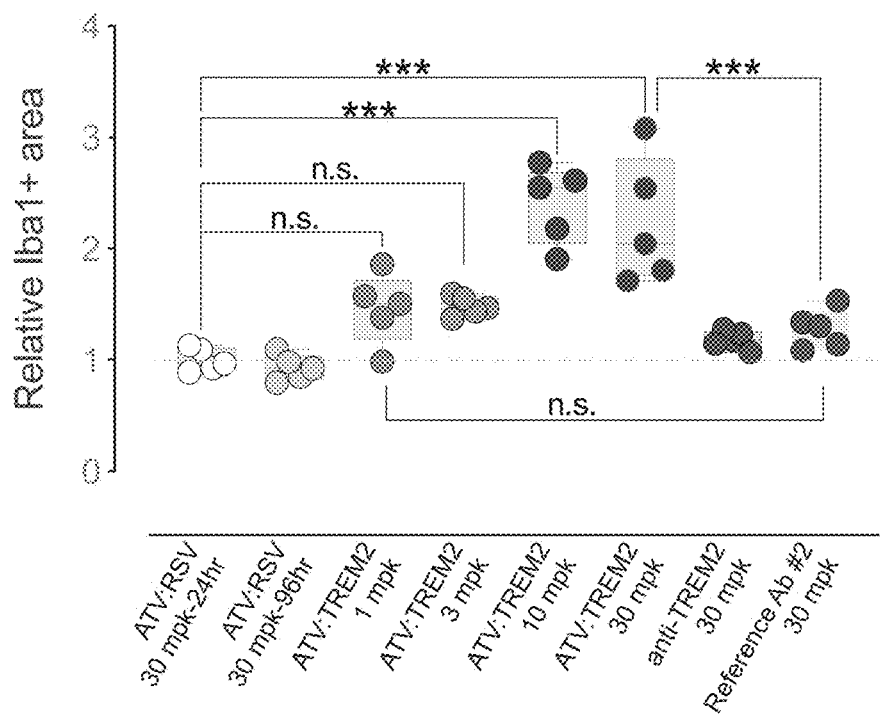

ATV:TREM2 is Dramatically More Potent for Microglial Proliferation, Compared to Non-ATV TREM2 Antibodies in Mouse Model To determine the lowest effective dosage of ATV:TREM2 and to compare to non-ATV TREM2 antibodies, a single dose of ATV:TREM2 #3 (1, 3, 10, 30 mg/kg) or a corresponding TREM2 reference antibody ("TREM2 Ab;" 30 mg/kg), reference antibody #2 (30 mg/kg) or isotype control (ATV:RSV; 30 mg/kg) were intravenously administered to TB36/hTfR KI mice at day 0. To measure microglial proliferation, mice were IP administrated with EdU at day 0, day 1, day 2 and day 3 after antibody treatment. Mice were taken down at day 1 and day 4 for analysis. EdU-Iba1 double staining show's dosage-dependent increase of new born microglia from 1 mg/kg to 10 mg/kg of the ATV:TREM2-dosed animals at day 4, with 10 mg/kg ATV:TREM2 showing the maximum effect on microglial proliferation (FIGS. 17A and 17B). Furthermore, the effect of 1 mg/kg ATV:

TREM2 on microglial proliferation is slightly higher (not statistically significant) than either anti-TREM2 or reference antibody #2, despite 30-fold higher dosing.

ATV:TREM2 Transiently Increases Brain Cytokine Levels in TB36/hTfR KI Mice

Figure 18A:
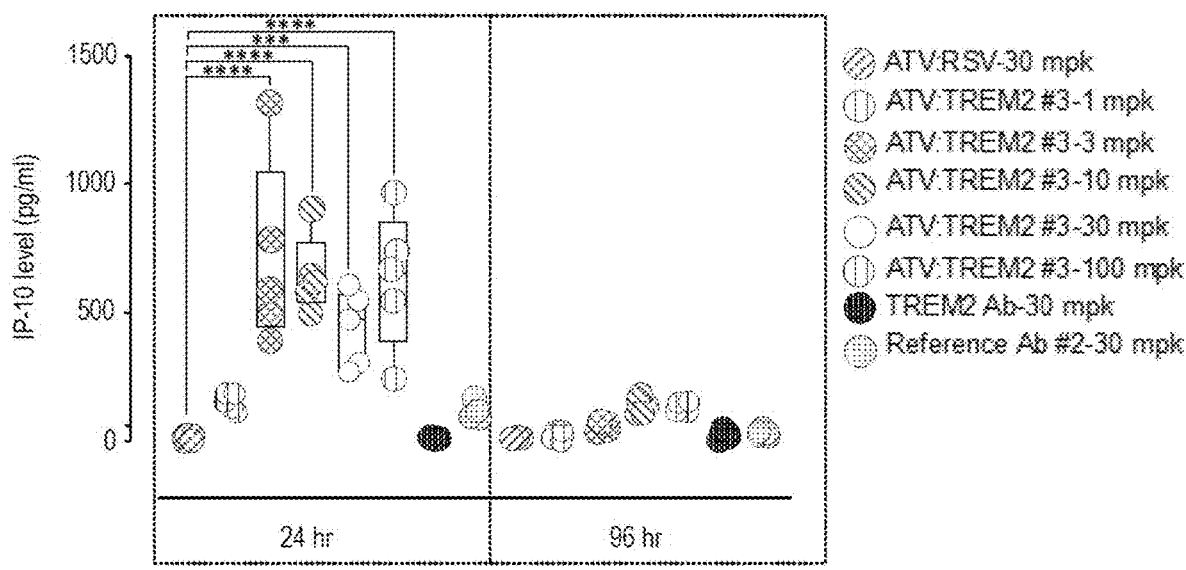
FIGS. 18A and 18B are plots showing cytokines IP-10 (FIG. 18A) and MCP-5 (FIG. 18B) levels in brains of TB36/hTfR KI mice treated with either ATV:TREM2, a corresponding TREM2 antibody, reference antibody #2, or ATV:RSV. Graphs display mean values across experimental replicates±SEM. Graphs display mean±SEM and p values: one-way ANOVA with Tukey's multiple comparison test;  p≤0.01, * p≤0.001, **** p≤0.0001.
Figure 18B:
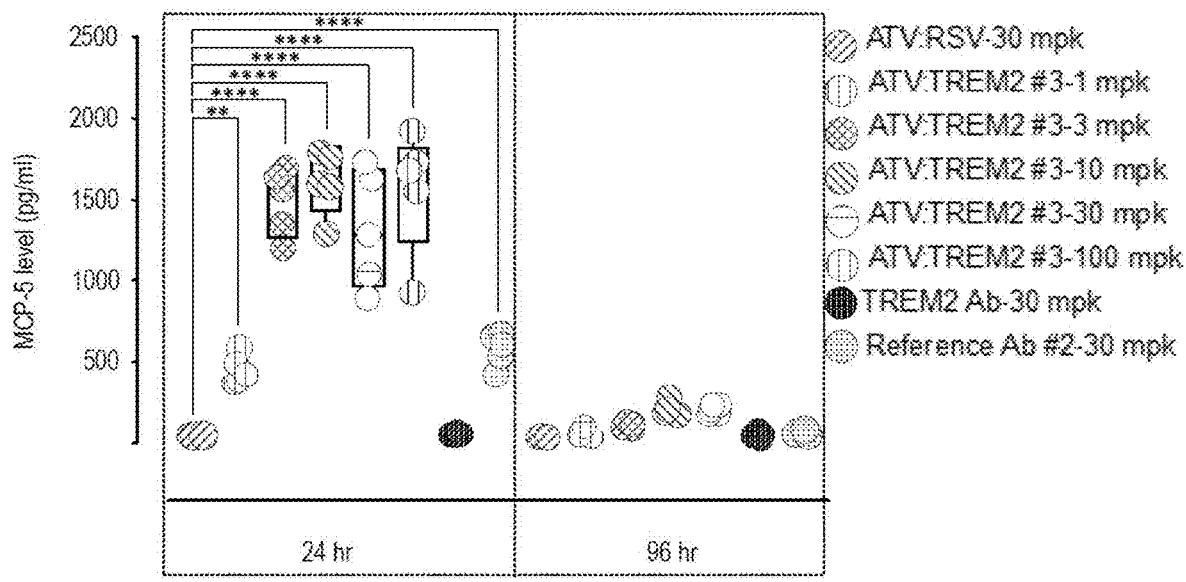

To determine the effect of ATV:TREM2 on cytokine (e.g., chemokine) levels, cytokine levels were measured in terminal plasma and brain lysates (prepared by Cell Signaling lysis buffer #9803) of TB36/hTfR KI mice using the Mouse Cytokine Array/Chemokine Array 44-Plex (MD44). We found that treatment with ATV:TREM2 #3 did not change the cytokine levels measured in the plasma, but acutely increased some cytokine levels (e.g., IP-10 and MCP-5) measured in the brain at 24-hr post-dose, and these cytokine levels were restored to the baseline level at 96-hr post-dose. ATV:TREM2 #3 at 3 mg/kg had maximum effect on brain cytokine levels (FIGS. 18A and 18B).

ATV:TREM2 Increases Brain CSF1R Level in TB36/hTfR KI Mice

Figure 19:
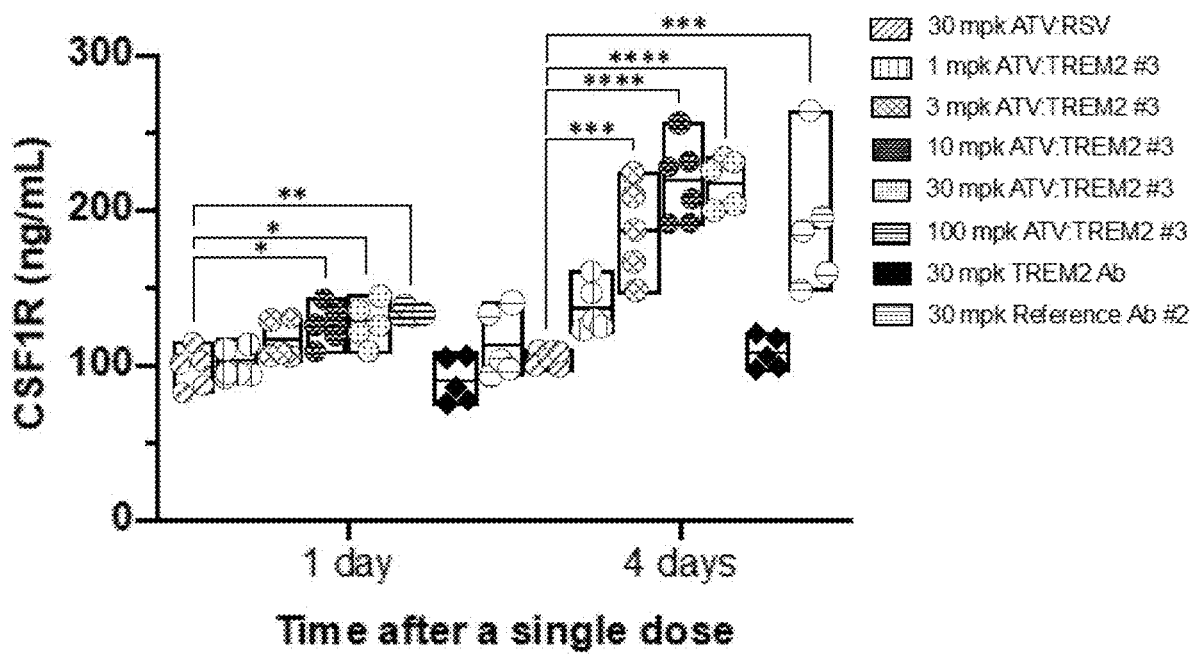
FIG. 19 is a plot showing glial marker CSF1R level in brains of TB36/hTfR KI mice treated with either ATV: TREM2, a corresponding TREM2 antibody, reference antibody #2, or ATV:RSV. Graphs display mean±SEM and p values: one-way ANOVA with Tukey's multiple comparison test; * p≤0.05,  p≤0.01, * p≤0.001, **** p≤0.0001.

To determine the effect of ATV:TREM2 on the level of glial marker CSF1R, CSF1R protein level was measured in brain lysates (prepared by Cell Signaling lysis buffer #9803) of TB36/hTfR KI mice using a commercial ELISA kit (Abcam ab240681). We found that increasing doses of ATV:TREM2 #3 resulted in an increased CSF1R protein level at 1 day after treatment and 4 days after treatment (FIG. 19).

Plasma PK Profile of ATV:TREM2

Figure 20:
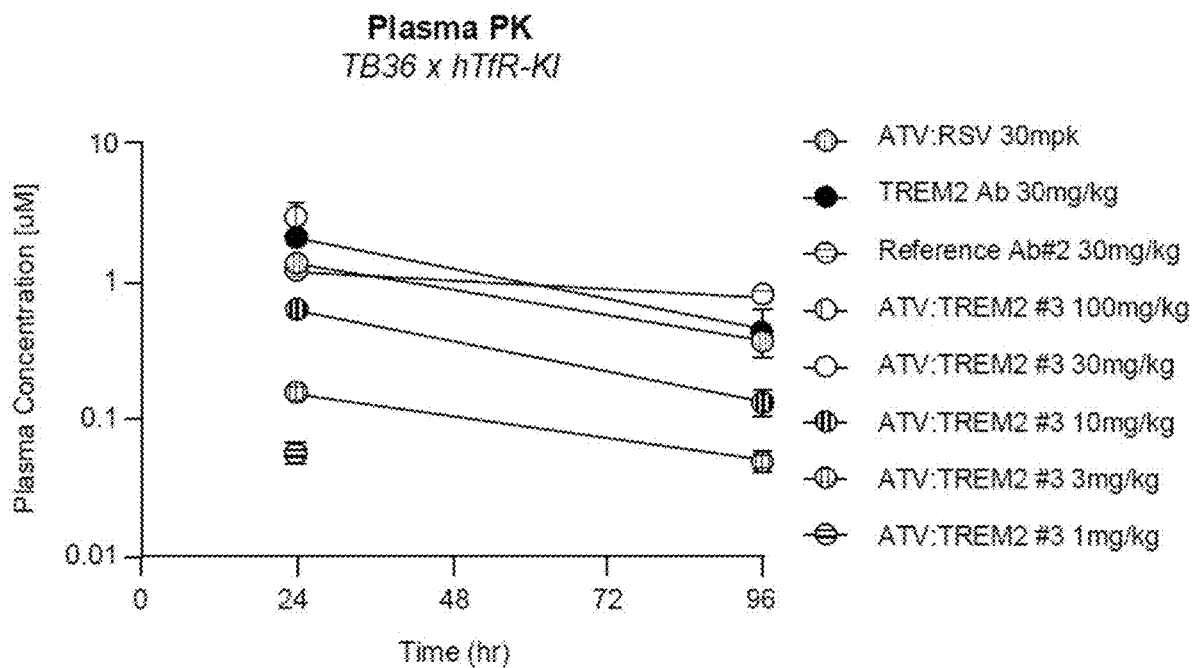
FIG. 20 is a plot showing the plasma PK profile of either ATV:TREM2, a corresponding TREM2 antibody, reference antibody #2, or ATV:RSV in TB36/hTfR KI mice.

Proportional increases in plasma PK were observed with doses of ATV:TREM2 #3 ranging from 1 mg/kg to 100 mg/kg. At 24 hours, the plasma concentrations of matched doses of 30 mg/kg of ATV:TREM2 #3, reference antibody #2, and TREM2 Ab were not significantly different. Reference antibody #2 appeared to have a lower clearance compared to ATV:TREM2 #3 and TREM2 Ab at the same dose (FIG. 20).

Brain PK Profile of ATV:TREM2

Figure 21:
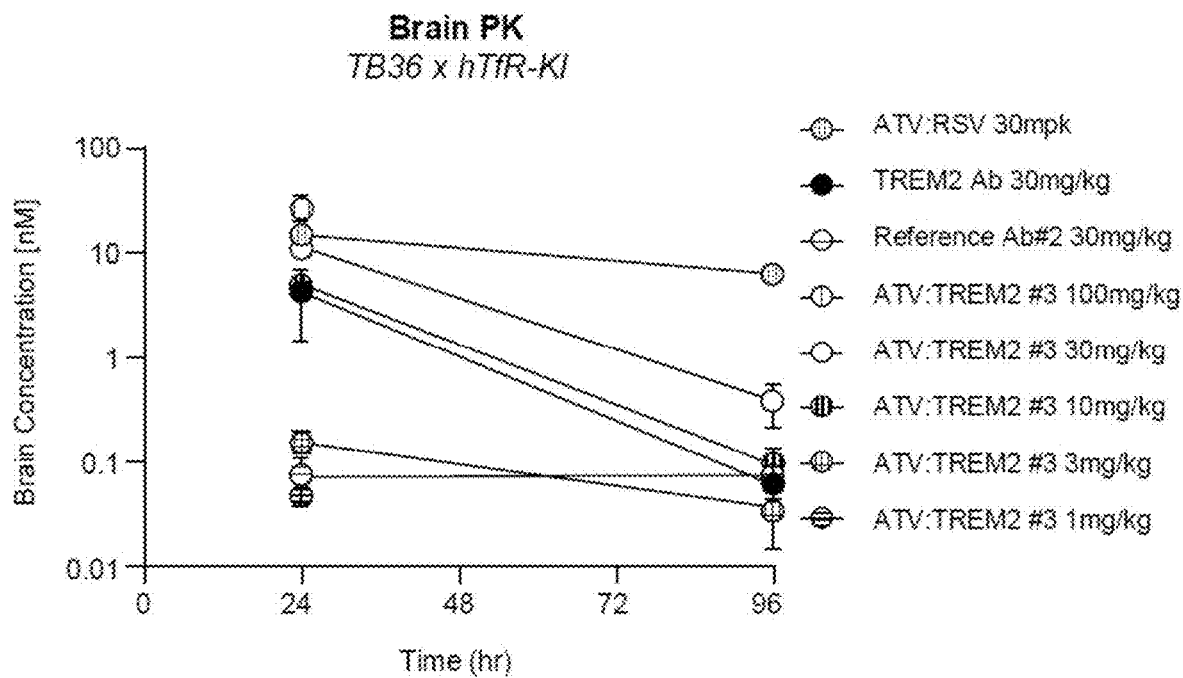
FIG. 21 is a plot showing the brain PK profile of either ATV:TREM2, a corresponding TREM2 antibody, reference antibody #2, or ATV:RSV in TB36/hTfR KI mice.

At 24 hours, the brain concentration of 10 mg/kg of ATV:TREM2 #3 was similar to TREM2 Ab at 30 mg/kg, and the brain concentration of 1-3 mg/kg of ATV:TREM2 #3 was similar to reference antibody #2 at 30 mg/kg. More than proportional increases were observed at doses of 3 mg/kg to 10 mg/kg of ATV:TREM2 #3, and proportional increases were observed at other doses. At 96 hours, the brain concentration of 10 mg/kg of ATV:TREM2 #3 was similar to TREM2 Ab and the reference antibody #2 at 30 mg/kg (FIG. 21). Overall, brain uptake of ATV:TREM2 #3 is more efficient than TREM2 Ab and reference antibody #2.

TABLE 8

Informal Sequence Listing

| SEQ ID NO | Sequence | Description |
| --- | --- | --- |
| 1 | MEPLRLLILLFVTELSGAHNTTVFQGVAGQSLQVSCPYDSMKH WGRRKAWCRQLGEKGPCQRVVSTHNLWLLSFLRRWNGSTAIT DDTLGGTLTITLRNLQPHDAGLYQCQSLHGSEADTLRKVLVEVL ADPLDHRDAGDLWFPGESESFEDAHVEHSISRSLLEGEIPFPPTSI LLLLACIFLIKILAASALWAAAWHGQKPGTHPPSELDCGHDPGY QLQTLPGLRDT | Human TREM2 protein |
| 2 | EVKLLDSGGGLVQAGGSLRLSCAGSGFTFTDFYMSWIRQPPGKA PEWLGVIRNKANGYTAGYNPSVKGRFTISRDNTQNILYLQMNTL RAEDTAIYYCARLSYGFDYWGQGVMVTVSS | CL0020306 $V_H$ |
| 3 | DIVMTQGALPNPVPSGESASITCQSSKSLLHSNGKTYLNWYLQR PGQSPQLLIYWMSTRASGVSDRFSGSGSGTDFTLKISSVEAEDVG VYYCQQFLEFPFTFGSGTKLEIK | CL0020306 $V_L$ |
| 4 | GFTFTDFYMS | CL0020306 CDR-H1; CL0020164 CDR-H1; CDR-H1 for CL0020188 and variants CL0020188-1, CL0020188-2, CL0020188-3, CL0020188-4, CL0020188-5, CL0020188-6, CL0020188-7, and CL0020188-8 |
| 5 | VIRNKANGYTAGYNPSVKG | CL0020306 CDR-H2; CDR-H2 for CL0020188 and variants CL0020188-1, CL0020188-2, CL0020188-3, and CL0020188-4 |
| 6 | ARLSYGFDY | CL0020306 CDR-H3 |
| 7 | QSSKSLLHSNGKTYLN | CL0020306 CDR-L1; CL0020164 CDR-L1; CL0020307 CDR-L1; CL0020307-1 CDR-L1; CDR-L1 for CL0020188 and variants CL0020188-1, CL0020188-2, CL0020188-5, and CL0020188-6 |

TABLE 8-continued

Informal Sequence Listing

| SEQ ID NO | Sequence | Description |
|---|---|---|
| 8 | WMSTRAS | CL0020306 CDR-L2; CL0020307 CDR-L2; CL0020307-1 CDR-L2; CL0020164 CDR-L2; CDR-L2 for CL0020188 and variants CL0020188-1, CL0020188-2, CL0020188-3, CL0020188-4, CL0020188-5, CL0020188-6, CL0020188-7, and CL0020188-8 |
| 9 | QQFLEFPFT | CL0020306 CDR-L3; CL0020307 CDR-L3; CL0020307-1 CDR-L3 |
| 10 | EVKLLESGGGLVQPGGSLRLSCAASGFTFTNFYMSWIRQPPGRAPEWLGVIRNRPNGYTTDYNPSVKGRFTISRDNTQNILYLQMSTLRADDTAFYYCTRLTYGFDYWGQGVMVTVSS | CL0020307 V$_H$ |
| 11 | DIVMTQGALPNPVPSGESASITCQSSKSLLHSNGKTYLNWYLQRPGQSPQLLIYWMSTRASGVSDRFSGSGSGTDFTLKISSVEAEVVGVYYCQQFLEFPFTFGSGTKLEIK | CL0020307 V$_L$ |
| 12 | GFTFTNFYMS | CL0020307 CDR-H1 |
| 13 | VIRNRPNGYTTDYNPSVKG | CL0020307 CDR-H2 |
| 14 | TRLTYGFDY | CL0020307 CDR-H3 |
| 15 | EVKLLDSGGGLVQAGGSLRLSCAGSGFTFTDFYMSWIRQPPGKAPEWLGVIRNKANGYTAGYNPSVKGRFTISRDNTQNILYLQMNTLRAEDTAIYYCARLTYGFDYWGQGVMVTVSS | CL0020188 V$_H$ |
| 16 | DIVMTQGALPNPVPSGESASITCQSSKSLLHSNGKTYLNWYLQRPGQSPQLLIYWMSTRASGVSDRFSGSGSGTDFTLKISSVEAEDVGVYYCQQFLEYPFTFGSGTKLEIK | CL0020188 V$_L$ |
| 17 | ARLTYGFDY | CDR-H3 for CL0020188 and variants CL0020188-1, CL0020188-2, CL0020188-3, CL0020188-4, CL0020188-5, CL0020188-6, CL0020188-7, and CL0020188-8; CL0020164 CDR-H3 |
| 18 | QQFLEYPFT | CDR-L3 for CL0020188 and variants CL0020188-1, CL0020188-2, CL0020188-3, CL0020188-4, CL0020188-5, CL0020188-6, CL0020188-7, and CL0020188-8 |
| 19 | EVQLVESGGGLVQPGGSLRLSCAASGFTFTDFYMSWVRQAPGKGLEWVSVIRNKANGYTAGYNPSVKGRFTISRDNSKNTLYLQMNSLRAEDTAVYYCARLTYGFDYWGQGTLVTVSS | CL0020188-1 V$_H$; CL0020188-3 V$_H$ |
| 20 | DIVMTQTPLSLPVTPGEPASISCQSSKSLLHSNGKTYLNWYLQKPGQSPQLLIYWMSTRASGVPDRFSGSGSGTDFTLKISRVEAEDVGVYYCQQFLEYPFTFGQGTKVEIK | CL0020188-1 V$_L$; CL0020188-2 V$_L$; CL0020188-5 V$_L$; CL0020188-6 V$_L$ |
| 21 | EVQLVESGGGLVQPGGSLRLSCAGSGFTFTDFYMSWVRQAPGKGLEWVSVIRNKANGYTAGYNPSVKGRFTISRDNSKNTLYLQMNSLRAEDTAVYYCARLTYGFDYWGQGTLVTVSS | CL0020188-2 V$_H$; CL0020188-4 V$_H$ |
| 22 | DIVMTQTPLSLPVTPGEPASISCQSSKSLLHSTGKTYLNWYLQKPGQSPQLLIYWMSTRASGVPDRFSGSGSGTDFTLKISRVEAEDVGVYYCQQFLEYPFTFGQGTKVEIK | CL0020188-3 V$_L$; CL0020188-4 V$_L$; CL0020188-7 V$_L$; CL0020188-8 V$_L$ |
| 23 | QSSKSLLHSTGKTYLN | CDR-L1 for variants CL0020188-3, CL0020188-4, CL0020188-7, and CL0020188-8 |

TABLE 8-continued

Informal Sequence Listing

| SEQ ID NO | Sequence | Description |
|---|---|---|
| 24 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSS | CL0020188-5 $V_H$; CL0020188-7 $V_H$ |
| 25 | VIRNKANAYTAGYNPSVKG | CDR-H2 for variants CL0020188-5, CL0020188-6, CL0020188-7, and CL0020188-8 |
| 26 | EVQLVESGGGLVQPGGSLRLSCAGSGFTFTDFYMSWVRQAPGK GPEWLSVIRNKANAYTAGYNPSVKGRFTISRDNSKNTLYLQMN SLRAEDTAVYYCARLTYGFDYWGQGTLVTVSS | CL0020188-6 $V_H$; CL0020188-8 $V_H$ |
| 27 | DIVMTQSPDSLAVSLGERATINCQSSKSLLHSNGKTYLNWYQQK PGQPPKLLIYWMSTRASGVPDRFSGSGSGTDFTLTISSLQAEDVA VYYCQQFLEFPFTFGQGTKVEIK | CL0020307-1 $V_L$ |
| 28 | G-F-T-F-T-$\alpha_6$-F-Y-M-S, wherein $\alpha_6$ is D or N | CDR-H1 consensus sequence |
| 29 | V-I-R-N-$\beta_5$-$\beta_6$-N-$\beta_8$-Y-T-$\beta_{11}$-$\beta_{12}$-Y-N-P-S-V-K-G, wherein $\beta_5$ is K or R; $\beta_6$ is A or P; $\beta_8$ is G or A; $\beta_{11}$ is A or T; and $\beta_{12}$ is G or D | CDR-H2 consensus sequence |
| 30 | $\gamma_1$-R-L-$\gamma_4$-Y-G-F-D-Y, wherein $\gamma_1$ is A or T; and $\gamma_4$ is T or S | CDR-H3 consensus sequence |
| 31 | Q-S-S-K-S-L-L-H-S-$\delta_{10}$-G-K-T-Y-L-N, wherein $\delta_{10}$ is N or T | CDR-L1 consensus sequence |
| 32 | Q-Q-F-L-E-$\phi_6$-P-F-T, wherein $\phi_6$ is Y or F | CDR-L3 consensus sequence |
| 33 | 000 | |
| 34 | GGGGS | Linker sequence |
| 35 | HHHHHH | 6X-His tag |
| 36 | ASTKGPSVFPLAPSSKSTSGGTAALGCLVKDYFPEPVTVSWNSG ALTSGVHTFPAVLQSSGLYSLSSVVTVPSSSLGTQTYICNVNHKP SNTKVDKKVEPKSCDKTHTCPPCP | Heavy chain constant domain 1 (CH1) |
| 37 | RTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC | light chain constant domain (CL) |
| 38 | APELLGGPSVFLFPPKPKDTLMISRTPEVTCVVVDVSHEDPEVKF NVVYVDGVEVHNAKTKPREEQYNSTYRVVSVLTVLHQDWLNG KEYKCKVSNKALPAPIEKTISKAKGQPREPQVYTLPPSRDELTKN QVSLTCLVKGFYPSDIAVEWESNGQPENNYKTTPPVLDSDGSFF LYSKLTVDKSRWQQGNVFSCSVMHEALHNHYTQKSLSLSPGK | Wild-type human Fc sequence positions 231-447 EU index numbering |
| 39 | APEAAGGPSVFLFPPKPKDTLMISRTPEVTCVVVDVSHEDPEVKF NVVYVDGVEVHNAKTKPREEQYNSTYRVVSVLTVLHQDWLNG KEYKCKVSNKALPAPIEKTISKAKGQPREPQVYTLPPSRDELTKN QVSLSCAVKGFYPSDIAVEWESNGQPENNYKTTPPVLDSDGSFF LVSKLTVDKSRWQQGNVFSCSVLHEALHSHYTQKSLSLSPGK | Fc polypeptide with hole, LALA, and LS mutations |
| 40 | APELLGGPSVFLFPPKPKDTLMISRTPEVTCVVVDVSHEDPEVKF NVVYVDGVEVHNAKTKPREEQYNSTYRVVSVLTVLHQDWLNG KEYKCKVSNKALPAPIEKTISKAKGQPREPQVYTLPPSRDELTKN QVSLTCLVKGFYPSDIAVWWESYG1EWSSYKTTPPVLDSDGSFF LYSKLTVTKEEWQQGFVFSCSVMHEALHNHYTQKSLSLSPGK | Clone 35.21 |
| 41 | APEAAGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSRDELTKN QVSLWCLVKGFYPSDIAVWWESYGTEWSSYKTTPPVLDSDGSF FLYSKLTVTKEEWQQGFVFSCSVLHEALHSHYTQKSLSLSPGK | Clone CH3C.35.21 Fc polypeptide with knob, LALA, and LS mutations |
| 42 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP | anti-TREM2/CH35.21 heavy chain with knob, LALA and LS mutations |

TABLE 8-continued

Informal Sequence Listing

| SEQ ID NO | Sequence | Description |
|---|---|---|
| | KSCDKTHTCPPCPAPEAAGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VYTLPPSRDELTKNQVSLWCLVKGFYPSDIAVWWESYGTEWSS YKTTPPVLDSDGSFFLYSKLTVTKEEWQQGFVFSCSVLHEALHS HYTQKSLSLSPGK | |
| 43 | APELLGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSRDELTKN QVSLTCLVKGFYPSDIAVEWESFGTEWSNYKTTPPVLDSDGSFF LYSKLTVSKEEWQQGFVFSCSVMHEALHNHYTQKSLSLSPGK | Clone CH3C.35.23.1.1 |
| 44 | APEAAGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSRDELTKN QVSLWCLVKGFYPSDIAVEWESFGIEWSNYKTTPPVLDSDGSFF LYSKLTVSKEEWQQGFVFSCSVLHEALHSHYTQKSLSLSPGK | Clone CH3C.35.23.1.1 Fc polypeptide with knob, LALA, and LS mutations |
| 45 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPEAAGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VYTLPPSRDELTKNQVSLWCLVKGFYPSDIAVEWESFGIEWSNY KTTPPVLDSDGSFFLYSKLTVSKEEWQQGFVFSCSVLHEALHSH YTQKSLSLSPGK | anti-TREM2/CH35.23.1.1 heavy chain with knob, LALA and LS mutations |
| 46 | APELLGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSRDELTKN QVSLTCLVKGFYPSDIAVEWESYGTEWVNYKTTPPVLDSDGSFF LYSKLTVTKEEWQQGFVFSCSVMHEALHNHYTQKSLSLSPGK | Clone CH3C.35.23.3 |
| 47 | APEAAGGPSVFLFPPKPKDTLMISRTPEVTCVVVDVSHEDPEVKF NVVYVDGVEVHNAKTKPREEQYNSTYRVVSVLTVLHQDWLNG KEYKCKVSNKALPAPIEKTISKAKGQPREPQVYTLPPSRDELTKN QVSLWCLVKGFYPSDIAVEWESYGTEWVNYKTTPPVLDSDGSF FLYSKLTVTKEEWQQGFVFSCSVLHEALHSHYTQKSLSLSPGK | CH3C.35.23.3 Fc polypeptide with knob, LALA, and LS mutations |
| 48 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPEAAGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VYTLPPSRDELTKNQVSLWCLVKGFYPSDIAVEWESYGTEWVN YKTTPPVLDSDGSFFLYSKLTVTKEEWQQGFVFSCSVLHEALHS HYTQKSLSLSPGK | anti-TREM2/CH35.23.3 heavy chain with knob, LALA and LS mutations |
| 49 | APELLGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSRDELTKN QVSLTCLVKGFYPSDIAVEWESYGTEWSNYKTTPPVLDSDGSFF LYSKLTVSKEEWQQGFVFSCSVMHEALHNHYTQKSLSLSPGK | Clone CH3C.35.23.4 |
| 50 | APEAAGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSRDELTKN QVSLWCLVKGFYPSDIAVEWESYGTEWSNYKTTPPVLDSDGSFF LYSKLTVSKEEWQQGFVFSCSVLHEALHSHYTQKSLSLSPGK | CH3C.35.23.4 Fc polypeptide with knob, LALA, and LS mutations |
| 51 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPEAAGGPSVFLFPPKPKDTLMISRTPEVTCV VVDVSHEDPEVKFNWYVDGVEVHNAKTKPREEQYNSTYRVVS | anti-TREM2/CH35.23.4 heavy chain with knob, LALA and LS mutations |

TABLE 8-continued

Informal Sequence Listing

| SEQ ID NO | Sequence | Description |
|---|---|---|
| | VLTVLHQDWLNGKEYKCKVSNKALPAPIEKTISKAKGQPREPQ VYTLPPSRDELTKNQVSLWCLVKGFYPSDIAVEWESYGTEWSN YKTTPPVLDSDGSFFLYSKLTVSKEEWQQGFVFSCSVLHEALHS HYTQKSLSLSPGK | |
| 52 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPELLGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VYTLPPSRDELTKNQVSLSCAVKGFYPSDIAVEWESNGQPENNY KTTPPVLDSDGSFFLVSKLTVDKSRWQQGNVFSCSVLHEALHSH YTQKSLSLSPGK | anti-TREM2 heavy chain with hole and LS mutations |
| 53 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPEAAGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VYTLPPSRDELTKNQVSLSCAVKGFYPSDIAVEWESNGQPENNY KTTPPVLDSDGSFFLVSKLTVDKSRWQQGNVFSCSVLHEALHSH YTQKSLSLSPGK | anti-TREM2 heavy chain with hole, LALA and LS mutations |
| 54 | DIVMTQTPLSLPVTPGEPASISCQSSKSLLHSTGKTYLNWYLQKP GQSPQLLIYWMSTRASGVPDRFSGSGSGTDFTLKISRVEAEDVG VYYCQQFLEYPFTFGQGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC | anti-TREM2 light chain |
| 55 | NSVIIVDKNGRLVYLVENPGGYVAYSKAATVTGKLVHANFGTK KDFEDLYTPVNGSIVIVRAGKITFAEKVANAESLNAIGVLIYMDQ TKFPIVNAELSFFGHAHLGTGDPYTPGFPSFNHTQFPPSRSSGLPN IPVQTISRAAAEKLFGNMEGDCPSDWKTDSTCRMVTSESKNVKL TVS | Human TfR apical domain |
| 56 | GGGGSGGGGS | Linker |
| 57 | DKTHTCPPCP | Portion of human IgG1 hinge sequence |
| 58 | YxTEWSS | CH3 motif (TfR-binding) |
| 59 | TxxExxxxF | CH3 motif (TfR-binding) |
| 60 | MMDQARSAFSNLFGGEPLSYTRFSLARQVDGDNSHVEMKLGV DEEENTDNNTKANGTKPKRCGGNICYGTIAVIIFFLIGFMIGYLG YCKGVEPKIECERLAGIESPAREEPEEDFPAAPRLYWDDLKRKL SEKLDTTDFTSTIKLLNENLYVPREAGSQKDENLALYIENQFREF KLSKVWRDQHFVKIQVKDSAQNSVIIVDKNGGLVYLVENPGGY VAYSKAATVTGKLVHANFGTKKDFEDLDSPVNGSIVIVRAGKIT FAEKVANAESLNAIGVLIYMDQTKFPIVKADLSFFGHAHLGTGD PYTPGFPSFNHTQFPPSQSSGLPNIPVQTISRAAAEKLFGNMEGDC PSDWKTDSTCKMVTSENKSVKLTVSNVLKETKILNIFGVIKGFV EPDHYVVVGAQRDAWGPGAAKSSVGTALLLKLAQMFSDMVLK DGFQPSRSIIFASWSAGDFGSVGAIEWLEGYLSSLHLKAFTYINL DKAVLGTSNFKVSASPLLYTLIEKTMQDVKHPVTGRSLYQDSN WASKVEKLTLDNAAFPFLAYSGIPAVSFCFCEDTDYPYLGTTMD TYKELVERIPELNKVARAAAEVAGQFVIKLTHDIELNLDYERYN SQLLLFLRDLNQYRADVKEMGLSLQWLYSARGDFFRATSRLTT DFRNAEKRDKFVMKKLNDRVMRVEYYFLSPYVSPKESPFRHVF WGSGSHTLSALLESLKLRRQNNSAFNETLFRNQLALATWTIQGA ANALSGDVWDIDNEF | Cyno TfR |
| 61 | APELLGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSRDELTKN QVSLSCAVKGFYPSDIAVEWESNGQPENNYKTTPPVLDSDGSFF LVSKLTVDKSRWQQGNVFSCSVLHEALHSHYTQKSLSLSPGK | Fc polypeptide with hole and LS mutations |

TABLE 8-continued

Informal Sequence Listing

| SEQ ID NO | Sequence | Description |
|---|---|---|
| 62 | MMDQARSAFSNLFGGEPLSYTRFSLARQVDGDNSHVEMKLAV DEEENADNNTKANVTKPKRCSGSICYGTIAVIVFFLIGFMIGYLG YCKGVEPKIECERLAGIESPVREEPGEDFPAARRLYWDDLKRK LSEKLDSTDFTGTIKLLNENSYVPREAGSQKDENLALYVENQFR EFKLSKVWRDQHFVKIQVKDSAQNSVIIVDKNGRLVYLVENPG GYVAYSKAATVTGKLVHANFGTKKDFEDLYTPVNGSIVIVRAG KITFAEKVANAESLNAIGVLIYMDQTKFPIVNAELSFFGHAHLGT GDPYTPGFPSFNHTQFPPPSRSSGLPNIPVQTISRAAAEKLFGNMEG DCPSDWKTDSTCRMVTSESKNVKLTVSNVLKEIKILNIFGVIKGF VEPDHYVVVGAQRDAWGPGAAKSGVGTALLLKLAQMFSDMV LKDGFQPSRSIIFASWSAGDFGSVGATEWLEGYLSSLHLKAFTYI NLDKAVLGTSNFKVSASPLLYTLIEKTMQNVKHPVTGQFLYQDS NVVASKVEKLTLDNAAFPFLAYSGIPAVSFCFCEDTDYPYLGTTM DTYKELIERIPELNKVARAAAEVAGQFVIKLTHDVELNLDYERY NSQLLSFVRDLNQYRADIKEMGLSLQWLYSARGDFFRATSRLTT DFGNAEKTDRFVMKKLNDRVMRVEYHFLSPYVSPKESPFRHVF WGSGSHTLPALLENLKLRKQNNGAFNETLFRNQLALATWTIQG AANALSGDVWDIDNEF | Human transferrin receptor protein 1 (TFR1) |
| 63 | APEAAGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSRDELTKN QVSLSCAVKGFYPSDIAVEWESNGQPENNYKTTPPVLDSDGSFF LVSKLTVDKSRWQQGNVFSCSVLHEALHSHYTQKSLSLSPG | Fc polypeptide with hole, LALA, and LS mutations, truncated |
| 64 | APEAAGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSRDELTKN QVSLWCLVKGFYPSDIAVWWESYGTEWSSYKTTPPVLDSDGSF FLYSKLTVTKEEWQQGFVFSCSVLHEALHSHYTQKSLSLSPG | Clone CH3C.35.21 Fc polypeptide with knob, LALA, and LS mutations, truncated |
| 65 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPEAAGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VYTLPPSRDELTKNQVSLWCLVKGFYPSDIAVWWESYGTEWSS YKTTPPVLDSDGSFFLYSKLTVTKEEWQQGFVFSCSVLHEALHS HYTQKSLSLSPG | anti-TREM2/CH35.21 heavy chain with knob, LALA and LS mutations, truncated |
| 66 | APEAAGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSRDELTKN QVSLWCLVKGFYPSDIAVEWESFGIEWSNYKTTPPVLDSDGSFF LYSKLTVSKEEWQQGFVFSCSVLHEALHSHYTQKSLSLSPG | Clone CH3C.35.23.1.1 Fc polypeptide with knob, LALA, and LS mutations, truncated |
| 67 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPEAAGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VYTLPPSRDELTKNQVSLWCLVKGFYPSDIAVEWESFGIEWSNY KTTPPVLDSDGSFFLYSKLTVSKEEWQQGFVFSCSVLHEALHSH YTQKSLSLSPG | anti-TREM2/CH35.23.1.1 heavy chain with knob, LALA and LS mutations, truncated |
| 68 | APEAAGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSRDELTKN QVSLWCLVKGFYPSDIAVEWESYGTEWVNYKTTPPVLDSDGSF FLYSKLTVTKEEWQQGFVFSCSVLHEALHSHYTQKSLSLSPG | CH3C.35.23.3 Fc polypeptide with knob, LALA, and LS mutations, truncated |
| 69 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPEAAGGPSVFLFPPKPKDTLMISRTPEVTCV VVDVSHEDPEVKFNWYVDGVEVHNAKTKPREEQYNSTYRVVS | anti-TREM2/CH35.23.3 heavy chain with knob, LALA and LS mutations, truncated |

TABLE 8-continued

Informal Sequence Listing

| SEQ ID NO | Sequence | Description |
|---|---|---|
| | VLTVLHQDWLNGKEYKCKVSNKALPAPIEKTISKAKGQPREPQ VYTLPPSRDELTKNQVSLWCLVKGFYPSDIAVEWESYGTEWVN YKTTPPVLDSDGSFFLYSKLTVTKEEWQQGFVFSCSVLHEALHS HYTQKSLSLSPG | |
| 70 | APEAAGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSRDELTKN QVSLWCLVKGFYPSDIAVEWESYGTEWSNYKTTPPVLDSDGSFF LYSKLTVSKEEWQQGFVFSCSVLHEALHSHYTQKSLSLSPG | CH3C.35.23.4 Fc polypeptide with knob, LALA, and LS mutations, truncated |
| 71 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPEAAGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VYTLPPSRDELTKNQVSLWCLVKGFYPSDIAVEWESYGTEWSN YKTTPPVLDSDGSFFLYSKLTVSKEEWQQGFVFSCSVLHEALHS HYTQKSLSLSPG | anti-TREM2/CH35.23.4 heavy chain with knob, LALA and LS mutations, truncated |
| 72 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPELLGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VYTLPPSRDELTKNQVSLSCAVKGFYPSDIAVEWESNGQPENNY KTTPPVLDSDGSFFLVSKLTVDKSRWQQGNVFSCSVLHEALHSH YTQKSLSLSPG | anti-TREM2 heavy chain with hole and LS mutations, truncated |
| 73 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPEAAGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VYTLPPSRDELTKNQVSLSCAVKGFYPSDIAVEWESNGQPENNY KTTPPVLDSDGSFFLVSKLTVDKSRWQQGNVFSCSVLHEALHSH YTQKSLSLSPG | anti-TREM2 heavy chain with hole, LALA and LS mutations, truncated |
| 74 | QVQLVQSGAEVKKPGASVKVSCKASGYAFSSQWMNWVRQAP GQRLEWIGRIYPGGGDTNYAGKFQGRVTITADTSASTAYMELSS LRSEDTAVYYCARLLRNQPGESYAMDYWGQGTLVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNTK VDKKVEPKSCDKTHTCPPCPAPELLGGPSVFLFPPKPKDTLMISR TPEVTCVVVDVSHEDPEVKFNWYVDGVEVHNAKTKPREEQYN STYRVVSVLTVLHQDWLNGKEYKCKVSNKALPAPIEKTISKAK GQPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPGK | Reference antibody #1 heavy chain |
| 75 | DVVMTQSPDSLAVSLGERATINCRSSQSLVHSNRYTYLHWYQQ KPGQSPKLLIYKVSNRFSGVPDRFSGSGSGTDFTLKISRVEAEDV GVYYCSQSTRVPYTFGQGTKLEIKRTVAAPSVFIFPPSDEQLKSG TASVVCLLNNFYPREAKVQWKVDNALQSGNSQESVTEQDSKDS TYSLSSTLTLSKADYEKHKVYACEVTHQGLSSPVTKSFNRGEC | Reference antibody #1 and #2 light chain |
| 76 | QVQLVQSGAEVKKPGASVKVSCKASGYAFSSQWMNWVRQAP GQRLEWIGRIYPGGGDTNYAGKFQGRVTITADTSASTAYMELSS LRSEDTAVYYCARLLRNQPGESYAMDYWGQGTLVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNTK VDKKVEPKSCDKTHTCPPCPAPELLGGPSVFLFPPKPKDTLMISR TPEVTCVVVDVSHEDPEVKFNWYVDGVEVHNAKTKPREEQYN STYRVVSVLTVLHQDWLNGKEYKCKVSNKALPASIEKTISKAK GQPREPQVYTLPPSRDELTKNQVSLTCLVKGFYPSDIAVEWESN | Reference antibody #2 heavy chain |

TABLE 8-continued

Informal Sequence Listing

| SEQ ID NO | Sequence | Description |
|---|---|---|
| | GQPENNYKTTPPVLDSDGSFFLYSKLTVDKSRWQQGNVFSCSV MHGALHNHYTQKSLSLSPGK | |
| 77 | QVQLQESGPGLVKPSETLSLTCAVSGYSITSDYAWNWIRQPPGK GLEWIGYMSYSGSTRYNPSLRSRVTISVDTSKNQFSLKLSSVTAA DTAVYYCARGWPLAYWGQGTLVTVSSASTKGPSVFPLAPSSKS TSGGTAALGCLVKDYFPEPVTVSWNSGALTSGVHTFPAVLQSSG LYSLSSVVTVPSSSLGTQTYICNVNHKPSNTKVDKKVEPKSCDK THTCPPCPAPELLGGPSVFLFPPKPKDTLMISRTPEVTCVVVDVS HEDPEVKFNWYVDGVEVHNAKTKPREEQYNSTYRVVSVLTVL HQDWLNGKEYKCKVSNKALPAPIEKTISKAKGQPREPQVYTLPP SRDELTKNQVSLTCLVKGFYPSDIAVEWESNGQPENNYKTTPPV LDSDGSFFLYSKLTVDKSRWQQGNVFSCSVMHEALHNHYTQKS LSLSPGK | Isotype control for reference antibodies #1 and #2, heavy chain |
| 78 | EIVMTQSPATLSLSPGERATLSCSASSSVSYMYWYQQKPGQAPR LLIYDTSNLASGIPARFSGSGSGTDFTLTISSLQPEDFAVYYCQQW SSYPPITFGQGTKVEIKRTVAAPSVFIFPPSDEQLKSGTASVVCLL NNFYPREAKVQWKVDNALQSGNSQESVTEQDSKDSTYSLSSTL TLSKADYEKHKVYACEVTHQGLSSPVTKSFNRGEC | Isotype control for reference antibodies #1 and #2, light chain |
| 79 | QVTLRESGPALVKPTQTLTLTCTFSGFSLSTSGMSVGWIRQPPGK ALEWLADIWWDDKKDYNPSLKSRLTISKDTSKNQVVLKVTNM EPADTATYYCARSMITNWYFDVWGAGTTVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKKV EPKSCDKTHTCPPCPAPEAAGGPSVFLFPPKPKDTLMISRTPEVT CVVVDVSHEDPEVKFNWYVDGVEVHNAKTKPREEQYNSTYRV VSVLTVLHQDWLNGKEYKCKVSNKALPAPIEKTISKAKGQPREP QVYTLPPSRDELTKNQVSLWCLVKGFYPSDIAVWWESYGTEWS SYKTTPPVLDSDGSFFLYSKLTVTKEEWQQGFVFSCSVMHEALH NHYTQKSLSLSPGK | Isotype control for ATV:TREM2 #1, heavy chain with knob, LALA |
| 80 | QVTLRESGPALVKPTQTLTLTCTFSGFSLSTSGMSVGWIRQPPGK ALEWLADIWWDDKKDYNPSLKSRLTISKDTSKNQVVLKVTNM EPADTATYYCARSMITNWYFDVWGAGTTVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKKV EPKSCDKTHTCPPCPAPEAAGGPSVFLFPPKPKDTLMISRTPEVT CVVVDVSHEDPEVKFNWYVDGVEVHNAKTKPREEQYNSTYRV VSVLTVLHQDWLNGKEYKCKVSNKALPAPIEKTISKAKGQPREP QVYTLPPSRDELTKNQVSLWCLVKGFYPSDIAVEWESYGTEWV NYKTTPPVLDSDGSFFLYSKLTVTKEEWQQGFVFSCSVMHEALH NHYTQKSLSLSPGK | Isotype control for ATV:TREM2 #3, heavy chain with knob, LALA |
| 81 | QVTLRESGPALVKPTQTLTLTCTFSGFSLSTSGMSVGWIRQPPGK ALEWLADIWWDDKKDYNPSLKSRLTISKDTSKNQVVLKVTNM EPADTATYYCARSMITNWYFDVWGAGTTVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKKV EPKSCDKTHTCPPCPAPEAAGGPSVFLFPPKPKDTLMISRTPEVT CVVVDVSHEDPEVKFNWYVDGVEVHNAKTKPREEQYNSTYRV VSVLTVLHQDWLNGKEYKCKVSNKALPAPIEKTISKAKGQPREP QVYTLPPSRDELTKNQVSLSCAVKGFYPSDIAVEWESNGQPENN YKTTPPVLDSDGSFFLVSKLTVDKSRWQQGNVFSCSVMHEALH NHYTQKSLSLSPGK | Isotype control for ATV:TREM#1 and #3, heavy chain with hole, LALA |
| 82 | DIQMTQSPSTLSASVGDRVTITCKCQLSVGYMHWYQQKPGKAP KLLIYDTSKLASGVPSRFSGSGSGTEFTLTISSLQPDDFATYYCFQ GSGYPFTFGGGTKLEIKRTVAAPSVFIFPPSDEQLKSGTASVVCLL NNFYPREAKVQWKVDNALQSGNSQESVTEQDSKDSTYSLSSTL TLSKADYEKHKVYACEVTHQGLSSPVTKSFNRGEC | Isotype control for ATV:TREM2 #1 and #3, light chain |
| 83 | EVQLVESGGGLVQPGGSLRLSCAASGFTFTDFYMSWVRQAPGK GLEWVSVIRNKANAYTAGYNPSVKGRFTISRDNSKNTLYLQMN SLRAEDTAVYYCARLTYGFDYWGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPEAAGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHN HYTQKSLSLSPGK | anti-TREM2 heavy chain with LALA mutations |

TABLE 8-continued

Informal Sequence Listing

| SEQ ID NO | Sequence | Description |
|---|---|---|
| 84 | APELLGGPSVFLFPPKPKDTLMISRTPEVTCVVVDVSHEDPEVKF NVVYVDGVEVHNAKTKPREEQYNSTYRVVSVLTVLHQDWLNG KEYKCKVSNKALPAPIEKTISKAKGQPREPQVYTLPPSRDELTKN QVSLSCAVKGFYPSDIAVEWESNGQPENNYKTTPPVLDSDGSFF LVSKLTVDKSRWQQGNVFSCSVLHEALHSHYTQKSLSLSPG | Fc polypeptide with hole and LS mutations, truncated |

What is claimed is:

1. An isolated antibody that specifically binds to a human triggering receptor expressed on myeloid cells 2 (TREM2), wherein the antibody comprises:
   (a) a variable region comprising:
   i. a CDR-H1 sequence comprising the sequence of G-F-T-F-T-$α_6$-F-Y-M-S (SEQ ID NO:28), wherein $α_6$ is D or N;
   ii. a CDR-H2 sequence comprising the sequence of V-I-R-N-$β_5$-$β_6$-N-$β_8$-Y-T-$β_{11}$-$β_{12}$-Y-N-P-S-V-K-G (SEQ ID NO:29), wherein $β_5$ is K or R; $β_6$ is A or P; $β_8$ is G or A; $β_{11}$ is A or T; and $β_{12}$ is G or D;
   iii. a CDR-H3 sequence comprising the sequence of $γ_1$-R-L-$γ_4$-Y-G-F-D-Y (SEQ ID NO:30), wherein $γ_1$ is A or T; and $γ_4$ is T or S;
   iv. a CDR-L1 sequence comprising the sequence of Q-S-S-K-S-L-L-H-S-$δ_{10}$-G-K-T-Y-L-N (SEQ ID NO:31), wherein $δ_{10}$ is N or T;
   v. a CDR-L2 sequence comprising the sequence WMSTRAS (SEQ ID NO:8); and
   vi. a CDR-L3 sequence comprising the sequence of Q-Q-F-L-E-$φ_6$-P-F-T (SEQ ID NO:32), wherein $φ_6$ is Y or F;
   (b) a first Fc polypeptide that specifically binds to human transferrin receptor 1 and comprises a sequence having at least 90% sequence identity to SEQ ID NO:49; and
   (c) a second Fc polypeptide.

2. The antibody of claim 1, wherein:

i. the CDR-H1 sequence is selected from the group consisting of SEQ ID NOS:4 and 12;

ii. the CDR-H2 sequence is selected from the group consisting of SEQ ID NOS:5, 13, and 25;
iii. the CDR-H3 sequence is selected from the group consisting of SEQ ID NOS:6, 14, and 17;
iv. the CDR-L1 sequence is selected from the group consisting of SEQ ID NOS:7 and 23;
v. the CDR-L2 sequence comprises the sequence WMSTRAS (SEQ ID NO:8); and
vi. the CDR-L3 sequence is selected from the group consisting of SEQ ID NOS:9 and 18.

3. The antibody of claim 1, wherein the variable region comprises a CDR-H1 comprising the amino acid sequence of SEQ ID NO:4, a CDR-H2 comprising the amino acid sequence of SEQ ID NO:25, a CDR-H3 comprising the amino acid sequence of SEQ ID NO: 17, a CDR-L1 comprising the amino acid sequence of SEQ ID NO:23, a CDR-L2 comprising the amino acid sequence of SEQ ID NO:8, and a CDR-L3 comprising the amino acid sequence of SEQ ID NO: 18.

4. The antibody of claim 1, wherein the variable region comprises a $V_H$ sequence that has at least 85% sequence identity to SEQ ID NO:24 and a $V_L$ sequence has at least 85% sequence identity to SEQ ID NO:22.

5. The antibody of claim 1, wherein the first Fc polypeptide comprises: Trp, Leu, or Glu at position 380; Tyr or Phe at position 384; Thr at position 386; Glu at position 387; Trp at position 388; Ser, Ala, or Val at position 389; Ser or Asn at position 390; Thr or Ser at position 413; Glu or Ser at position 415; Glu at position 416; and Phe at position 421, according to EU numbering.

6. The antibody of claim 5, wherein:
(a) the first Fc polypeptide has a T366W substitution and the second Fc polypeptide has T366S, L368A, and Y407V substitutions, according to EU numbering;
(b) the first Fc polypeptide and/or the second Fc polypeptide comprises amino acid substitutions of Ala at position 234 and Ala at position 235, according to EU numbering; and/or
(c) the first Fc polypeptide and/or the second Fc polypeptide comprises amino acid substitutions of Leu at position 428 and Ser at position 434, according to EU numbering.

7. The antibody of claim 1, wherein the first Fc polypeptide comprises the sequence of SEQ ID NO:41 or 64, and the second Fc polypeptide comprises the sequence of SEQ ID NO:39 or 63.

8. The antibody of claim 7, comprising:
(i) a first heavy chain (HC) comprising a $V_H$ comprising SEQ ID NO:24 and the first Fc polypeptide comprising SEQ ID NO:41 or 64;
(ii) a second heavy chain (HC) comprising a $V_H$ comprising SEQ ID NO:24 and the second Fc polypeptide comprising SEQ ID NO:39 or 63; and
(iii) two light chains each comprising a $V_L$ comprising SEQ ID NO:22.

9. The antibody of claim 8, comprising:
(i) a first heavy chain (HC) that comprises or consists of the amino acid sequence set forth in SEQ ID NO:42 or 65;
(ii) a second HC that comprises or consists of the amino acid sequence set forth in SEQ ID NO:53 or 73; and
(iii) a first and a second light chain (LC) that each comprises or consists of the amino acid sequence set forth in SEQ ID NO:54.

10. The antibody of claim 1, wherein the first Fc polypeptide comprises the sequence of SEQ ID NO:44 or 66, and the second Fc polypeptide comprises the sequence of SEQ ID NO:39 or 63.

11. The antibody of claim 10, comprising:
(i) a first heavy chain (HC) comprising a $V_H$ comprising SEQ ID NO:24 and the first Fc polypeptide comprising SEQ ID NO:44 or 66;
(ii) a second heavy chain (HC) comprising a $V_H$ comprising SEQ ID NO:24 and the second Fc polypeptide comprising SEQ ID NO:39 or 63; and
(iii) two light chains each comprising a $V_L$ comprising SEQ ID NO:22.

12. The antibody of claim 11, comprising:
(i) a first heavy chain (HC) that comprises or consists of the amino acid sequence set forth in SEQ ID NO:45 or 67;
(ii) a second HC that comprises or consists of the amino acid sequence set forth in SEQ ID NO:53 or 73; and
(iii) a first and a second light chain (LC) that each comprises or consists of the amino acid sequence set forth in SEQ ID NO:54.

13. The antibody of claim 1, wherein the first Fc polypeptide comprises the sequence of SEQ ID NO:47 or 68, and the second Fc polypeptide comprises the sequence of SEQ ID NO:39 or 63.

14. The antibody of claim 13, comprising:
(i) a first heavy chain (HC) comprising a $V_H$ comprising SEQ ID NO:24 and the first Fc polypeptide comprising SEQ ID NO:47 or 68;
(ii) a second heavy chain (HC) comprising a $V_H$ comprising SEQ ID NO:24 and the second Fc polypeptide comprising SEQ ID NO:39 or 63; and
(iii) two light chains each comprising a $V_L$ comprising SEQ ID NO:22.

15. The antibody of claim 14, comprising:
(i) a first heavy chain (HC) that comprises or consists of the amino acid sequence set forth in SEQ ID NO:48 or 69;
(ii) a second HC that comprises or consists of the amino acid sequence set forth in SEQ ID NO:53 or 73; and
(iii) a first and a second light chain (LC) that each comprises or consists of the amino acid sequence set forth in SEQ ID NO:54.

16. The antibody of claim 1, wherein the first Fc polypeptide comprises the sequence of SEQ ID NO:47 or 68, and the second Fc polypeptide comprises the sequence of SEQ ID NO:61 or 84.

17. The antibody of claim 16, comprising:
(i) a first heavy chain (HC) comprising a $V_H$ comprising SEQ ID NO:24 and the first Fc polypeptide comprising SEQ ID NO:47 or 68;
(ii) a second heavy chain (HC) comprising a $V_H$ comprising SEQ ID NO:24 and the second Fc polypeptide comprising SEQ ID NO:61 or 84; and
(iii) two light chains each comprising a $V_L$ comprising SEQ ID NO:22.

18. The antibody of claim 17, comprising:
(i) a first heavy chain (HC) that comprises or consists of the amino acid sequence set forth in SEQ ID NO:48 or 69;
(ii) a second HC that comprises or consists of the amino acid sequence set forth in SEQ ID NO:52 or 72; and
(iii) a first and a second light chain (LC) that each comprises or consists of the amino acid sequence set forth in SEQ ID NO:54.

19. The antibody of claim 1, wherein the first Fc polypeptide comprises the sequence of SEQ ID NO:50 or 70, and the second Fc polypeptide comprises the sequence of SEQ ID NO:39 or 63.

20. The antibody of claim 19, comprising:
(i) a first heavy chain (HC) comprising a $V_H$ comprising SEQ ID NO:24 and the first Fc polypeptide comprising SEQ ID NO:50 or 70;
(ii) a second heavy chain (HC) comprising a $V_H$ comprising SEQ ID NO:24 and the second Fc polypeptide comprising SEQ ID NO:39 or 63; and
(iii) two light chains each comprising a $V_L$ comprising SEQ ID NO:22.

21. The antibody of claim 20, comprising:
(i) a first heavy chain (HC) that comprises or consists of the amino acid sequence set forth in SEQ ID NO:51 or 71;
(ii) a second HC that comprises or consists of the amino acid sequence set forth in SEQ ID NO:53 or 73; and
(iii) a first and a second light chain (LC) that each comprises or consists of the amino acid sequence set forth in SEQ ID NO:54.

22. An isolated antibody that specifically binds to a human triggering receptor expressed on myeloid cells 2 (TREM2), wherein the antibody comprises:
(i) a first heavy chain (HC) comprising a $V_H$ comprising SEQ ID NO:24 and a first Fc polypeptide comprising SEQ ID NO:47;
(ii) a second heavy chain (HC) comprising a $V_H$ comprising SEQ ID NO:24 and a second Fc polypeptide comprising SEQ ID NO:39; and
(iii) two light chains each comprising a $V_L$ comprising SEQ ID NO:22.

23. The antibody of claim 22, comprising:
(i) a first heavy chain (HC) that consists of the amino acid sequence set forth in SEQ ID NO:48;
(ii) a second HC that consists of the amino acid sequence set forth in SEQ ID NO:53; and
(iii) a first and a second light chain (LC) that each consists of the amino acid sequence set forth in SEQ ID NO:54.

24. An isolated antibody that specifically binds to a human triggering receptor expressed on myeloid cells 2 (TREM2), wherein the antibody comprises:
(i) a first heavy chain (HC) comprising a $V_H$ comprising SEQ ID NO:24 and a first Fc polypeptide comprising SEQ ID NO:68;
(ii) a second heavy chain (HC) comprising a $V_H$ comprising SEQ ID NO:24 and a second Fc polypeptide comprising SEQ ID NO:63; and
(iii) two light chains each comprising a $V_L$ comprising SEQ ID NO:22.

25. The antibody of claim 24, comprising:
(i) a first heavy chain (HC) that consists of the amino acid sequence set forth in SEQ ID NO:69;
(ii) a second HC that consists of the amino acid sequence set forth in SEQ ID NO:73; and
(iii) a first and a second light chain (LC) that each consists of the amino acid sequence set forth in SEQ ID NO:54.

26. A pharmaceutical composition comprising the isolated antibody of claim 1 and a pharmaceutically acceptable carrier.

27. An isolated polynucleotide comprising:
(a) a nucleotide sequence encoding the antibody of claim 1; or
(b) a nucleotide sequence encoding SEQ ID NOS:42, 53, and 54; or
(c) a nucleotide sequence encoding SEQ ID NOS:45, 53, and 54; or
(d) a nucleotide sequence encoding SEQ ID NOS:48, 53, and 54; or
(e) a nucleotide sequence encoding SEQ ID NOS:48, 52, and 54; or
(f) a nucleotide sequence encoding SEQ ID NOS:51, 53, and 54.

28. A vector or host cell comprising the polynucleotide of claim 27.

29. A method of expressing an antibody that specifically binds to a human triggering receptor expressed on myeloid cells 2 (TREM2), comprising: culturing the host cell of claim 28 under conditions suitable for expression of the antibody.

30. An isolated antibody that specifically binds to a human triggering receptor expressed on myeloid cells 2 (TREM2), wherein the antibody comprises:
(a) a variable region comprising:
  i. a CDR-H1 sequence comprising the sequence of G-F-T-F-T-$\alpha_6$-F-Y-M-S(SEQ ID NO:28), wherein $\alpha_6$ is D or N;
  ii. a CDR-H2 sequence comprising the sequence of V-I-R-N-$\beta_5$-$\beta_6$-N-$\beta_8$-Y-T-$\beta_{11}$-$\beta_{12}$-Y-N-P-S-V-K-G (SEQ ID NO:29), wherein $\beta_5$ is K or R; $\beta_6$ is A or P; $\beta_8$ is G or A; $\beta_{11}$ is A or T; and $\beta_{12}$ is G or D;
  iii. a CDR-H3 sequence comprising the sequence of $\gamma_1$-R-L-$\gamma_4$-Y-G-F-D-Y (SEQ ID NO:30), wherein $\gamma_1$ is A or T; and $\gamma_4$ is T or S;
  iv. a CDR-L1 sequence comprising the sequence of Q-S-S-K-S-L-L-H-S-$\delta_{10}$-G-K-T-Y-L-N(SEQ ID NO:31), wherein $\delta_{10}$ is N or T;
  v. a CDR-L2 sequence comprising the sequence WMSTRAS (SEQ ID NO:8); and
  vi. a CDR-L3 sequence comprising the sequence of Q-Q-F-L-E-$\phi_6$-P-F-T (SEQ ID NO:32), wherein $\phi_6$ is Y or F;
(b) a first Fc polypeptide that specifically binds to human transferrin receptor 1 and comprises: Trp, Leu, or Glu at position 380; Tyr or Phe at position 384; Thr at position 386; Glu at position 387; Trp at position 388; Ser, Ala, or Val at position 389; Ser or Asn at position 390; Thr or Ser at position 413; Glu or Ser at position 415; Glu at position 416; and Phe at position 421, according to EU numbering; and
(c) a second Fc polypeptide.

31. The antibody of claim 30, wherein:
(a) the first Fc polypeptide has a T366W substitution and the second Fc polypeptide has T366S, L368A, and Y407V substitutions, according to EU numbering;
(b) the first Fc polypeptide and/or the second Fc polypeptide comprises amino acid substitutions of Ala at position 234 and Ala at position 235, according to EU numbering; and/or
(c) the first Fc polypeptide and/or the second Fc polypeptide comprises amino acid substitutions of Leu at position 428 and Ser at position 434, according to EU numbering.

\* \* \* \* \*

SEQUENCE LISTING

<160> NUMBER OF SEQ ID NOS: 84

<210> SEQ ID NO 1
<211> LENGTH: 230
<212> TYPE: PRT
<213> ORGANISM: Homo sapiens

<400> SEQUENCE: 1

```
Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
    210                 215                 220

Pro Gly Leu Arg Asp Thr
225                 230
```

<210> SEQ ID NO 2
<211> LENGTH: 118
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 2

Glu Val Lys Leu Leu Asp Ser Gly Gly Gly Leu Val Gln Ala Gly Gly
1               5                   10                  15

Ser Leu Arg Leu Ser Cys Ala Gly Ser Gly Phe Thr Phe Thr Asp Phe
            20                  25                  30

Tyr Met Ser Trp Ile Arg Gln Pro Pro Gly Lys Ala Pro Glu Trp Leu
        35                  40                  45

Gly Val Ile Arg Asn Lys Ala Asn Gly Tyr Thr Ala Gly Tyr Asn Pro
    50                  55                  60

Ser Val Lys Gly Arg Phe Thr Ile Ser Arg Asp Asn Thr Gln Asn Ile
65                  70                  75                  80

Leu Tyr Leu Gln Met Asn Thr Leu Arg Ala Glu Asp Thr Ala Ile Tyr
                85                  90                  95

Tyr Cys Ala Arg Leu Ser Tyr Gly Phe Asp Tyr Trp Gly Gln Gly Val
            100                 105                 110

Met Val Thr Val Ser Ser
        115

<210> SEQ ID NO 3
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Asp Ile Val Met Thr Gln Gly Ala Leu Pro Asn Pro Val Pro Ser Gly
1               5                   10                  15

Glu Ser Ala Ser Ile Thr Cys Gln Ser Ser Lys Ser Leu Leu His Ser
            20                  25                  30

Asn Gly Lys Thr Tyr Leu Asn Trp Tyr Leu Gln Arg Pro Gly Gln Ser
        35                  40                  45

Pro Gln Leu Leu Ile Tyr Trp Met Ser Thr Arg Ala Ser Gly Val Ser
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Val Gly Val Tyr Tyr Cys Gln Gln Phe
                85                  90                  95

Leu Glu Phe Pro Phe Thr Phe Gly Ser Gly Thr Lys Leu Glu Ile Lys
            100                 105                 110

<210> SEQ ID NO 4
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Phe Thr Phe Thr Asp Phe Tyr Met Ser
1               5                   10
```

```
<210> SEQ ID NO 5
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Val Ile Arg Asn Lys Ala Asn Gly Tyr Thr Ala Gly Tyr Asn Pro Ser
1               5                   10                  15

Val Lys Gly

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ala Arg Leu Ser Tyr Gly Phe Asp Tyr
1               5

<210> SEQ ID NO 7
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gln Ser Ser Lys Ser Leu Leu His Ser Asn Gly Lys Thr Tyr Leu Asn
1               5                   10                  15

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Trp Met Ser Thr Arg Ala Ser
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gln Gln Phe Leu Glu Phe Pro Phe Thr
1               5
```

-continued

```
<210> SEQ ID NO 10
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Val Lys Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Phe
            20                  25                  30

Tyr Met Ser Trp Ile Arg Gln Pro Pro Gly Arg Ala Pro Glu Trp Leu
        35                  40                  45

Gly Val Ile Arg Asn Arg Pro Asn Gly Tyr Thr Thr Asp Tyr Asn Pro
    50                  55                  60

Ser Val Lys Gly Arg Phe Thr Ile Ser Arg Asp Asn Thr Gln Asn Ile
65                  70                  75                  80

Leu Tyr Leu Gln Met Ser Thr Leu Arg Ala Asp Asp Thr Ala Phe Tyr
                85                  90                  95

Tyr Cys Thr Arg Leu Thr Tyr Gly Phe Asp Tyr Trp Gly Gln Gly Val
            100                 105                 110

Met Val Thr Val Ser Ser
        115

<210> SEQ ID NO 11
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Ile Val Met Thr Gln Gly Ala Leu Pro Asn Pro Val Pro Ser Gly
1               5                   10                  15

Glu Ser Ala Ser Ile Thr Cys Gln Ser Ser Lys Ser Leu Leu His Ser
            20                  25                  30

Asn Gly Lys Thr Tyr Leu Asn Trp Tyr Leu Gln Arg Pro Gly Gln Ser
        35                  40                  45

Pro Gln Leu Leu Ile Tyr Trp Met Ser Thr Arg Ala Ser Gly Val Ser
    50                  55                  60

Asp Arg Phe Ser Gly Ser Gly Ser Gly Thr Asp Phe Thr Leu Lys Ile
65                  70                  75                  80

Ser Ser Val Glu Ala Glu Val Val Gly Val Tyr Tyr Cys Gln Gln Phe
                85                  90                  95

Leu Glu Phe Pro Phe Thr Phe Gly Ser Gly Thr Lys Leu Glu Ile Lys
            100                 105                 110

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 12

Gly Phe Thr Phe Thr Asn Phe Tyr Met Ser
1               5                   10

<210> SEQ ID NO 13
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Val Ile Arg Asn Arg Pro Asn Gly Tyr Thr Thr Asp Tyr Asn Pro Ser
1               5                   10                  15

Val Lys Gly

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Thr Arg Leu Thr Tyr Gly Phe Asp Tyr
1               5

<210> SEQ ID NO 15
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Val Lys Leu Leu Asp Ser Gly Gly Gly Leu Val Gln Ala Gly Gly
1               5                   10                  15

Ser Leu Arg Leu Ser Cys Ala Gly Ser Gly Phe Thr Phe Thr Asp Phe
            20                  25                  30

Tyr Met Ser Trp Ile Arg Gln Pro Pro Gly Lys Ala Pro Glu Trp Leu
        35                  40                  45

Gly Val Ile Arg Asn Lys Ala Asn Gly Tyr Thr Ala Gly Tyr Asn Pro
    50                  55                  60

Ser Val Lys Gly Arg Phe Thr Ile Ser Arg Asp Asn Thr Gln Asn Ile
65                  70                  75                  80

Leu Tyr Leu Gln Met Asn Thr Leu Arg Ala Glu Asp Thr Ala Ile Tyr
                85                  90                  95

Tyr Cys Ala Arg Leu Thr Tyr Gly Phe Asp Tyr Trp Gly Gln Gly Val
            100                 105                 110

Met Val Thr Val Ser Ser
        115

<210> SEQ ID NO 16
<211> LENGTH: 112
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 16

Asp Ile Val Met Thr Gln Gly Ala Leu Pro Asn Pro Val Pro Ser Gly
1               5                   10                  15

Glu Ser Ala Ser Ile Thr Cys Gln Ser Ser Lys Ser Leu Leu His Ser
            20                  25                  30

Asn Gly Lys Thr Tyr Leu Asn Trp Tyr Leu Gln Arg Pro Gly Gln Ser
        35                  40                  45

Pro Gln Leu Leu Ile Tyr Trp Met Ser Thr Arg Ala Ser Gly Val Ser
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Val Gly Val Tyr Tyr Cys Gln Gln Phe
                85                  90                  95

Leu Glu Tyr Pro Phe Thr Phe Gly Ser Gly Thr Lys Leu Glu Ile Lys
            100                 105                 110

<210> SEQ ID NO 17
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ala Arg Leu Thr Tyr Gly Phe Asp Tyr
1               5

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gln Gln Phe Leu Glu Tyr Pro Phe Thr
1               5

<210> SEQ ID NO 19
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45
```

```
Ser Val Ile Arg Asn Lys Ala Asn Gly Tyr Thr Ala Gly Tyr Asn Pro
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Leu Thr Tyr Gly Phe Asp Tyr Trp Gly Gln Gly Thr
            100                 105                 110

Leu Val Thr Val Ser Ser
            115
```

<210> SEQ ID NO 20
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

```
Asp Ile Val Met Thr Gln Thr Pro Leu Ser Leu Pro Val Thr Pro Gly
 1               5                  10                  15

Glu Pro Ala Ser Ile Ser Cys Gln Ser Ser Lys Ser Leu Leu His Ser
                 20                  25                  30

Asn Gly Lys Thr Tyr Leu Asn Trp Tyr Leu Gln Lys Pro Gly Gln Ser
             35                  40                  45

Pro Gln Leu Leu Ile Tyr Trp Met Ser Thr Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Phe
                 85                  90                  95

Leu Glu Tyr Pro Phe Thr Phe Gly Gln Gly Thr Lys Val Glu Ile Lys
            100                 105                 110
```

<210> SEQ ID NO 21
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

```
Glu Val Gln Leu Val Glu Ser Gly Gly Gly Leu Val Gln Pro Gly Gly
 1               5                  10                  15

Ser Leu Arg Leu Ser Cys Ala Gly Ser Gly Phe Thr Phe Thr Asp Phe
                 20                  25                  30

Tyr Met Ser Trp Val Arg Gln Ala Pro Gly Lys Gly Leu Glu Trp Val
             35                  40                  45

Ser Val Ile Arg Asn Lys Ala Asn Gly Tyr Thr Ala Gly Tyr Asn Pro
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95
```

```
Tyr Cys Ala Arg Leu Thr Tyr Gly Phe Asp Tyr Trp Gly Gln Gly Thr
                100                 105                 110

Leu Val Thr Val Ser Ser
        115
```

<210> SEQ ID NO 22
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

```
Asp Ile Val Met Thr Gln Thr Pro Leu Ser Leu Pro Val Thr Pro Gly
1               5                   10                  15

Glu Pro Ala Ser Ile Ser Cys Gln Ser Ser Lys Ser Leu Leu His Ser
                20                  25                  30

Thr Gly Lys Thr Tyr Leu Asn Trp Tyr Leu Gln Lys Pro Gly Gln Ser
            35                  40                  45

Pro Gln Leu Leu Ile Tyr Trp Met Ser Thr Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Phe
                85                  90                  95

Leu Glu Tyr Pro Phe Thr Phe Gly Gln Gly Thr Lys Val Glu Ile Lys
                100                 105                 110
```

<210> SEQ ID NO 23
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 23

```
Gln Ser Ser Lys Ser Leu Leu His Ser Thr Gly Lys Thr Tyr Leu Asn
1               5                   10                  15
```

<210> SEQ ID NO 24
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
                20                  25                  30

Tyr Met Ser Trp Val Arg Gln Ala Pro Gly Lys Gly Leu Glu Trp Val
            35                  40                  45

Ser Val Ile Arg Asn Lys Ala Asn Ala Tyr Thr Ala Gly Tyr Asn Pro
        50                  55                  60
```

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser
        115

<210> SEQ ID NO 25
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Val Ile Arg Asn Lys Ala Asn Ala Tyr Thr Ala Gly Tyr Asn Pro Ser
1               5                   10                  15

Val Lys Gly

<210> SEQ ID NO 26
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Ser Trp Val Arg Gln Ala Pro Gly Lys Gly Pro Glu Trp Leu
        35                  40                  45

Ser Val Ile Arg Asn Lys Ala Asn Ala Tyr Thr Ala Gly Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser
        115

<210> SEQ ID NO 27
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Asp Ile Val Met Thr Gln Ser Pro Asp Ser Leu Ala Val Ser Leu Gly
1               5                   10                  15

Glu Arg Ala Thr Ile Asn Cys Gln Ser Ser Lys Ser Leu Leu His Ser
            20                  25                  30

Asn Gly Lys Thr Tyr Leu Asn Trp Tyr Gln Gln Lys Pro Gly Gln Pro
        35                  40                  45

Pro Lys Leu Leu Ile Tyr Trp Met Ser Thr Arg Ala Ser Gly Val Pro
    50                  55                  60

Asp Arg Phe Ser Gly Ser Gly Ser Gly Thr Asp Phe Thr Leu Thr Ile
65              70                  75                  80

Ser Ser Leu Gln Ala Glu Asp Val Ala Val Tyr Tyr Cys Gln Gln Phe
                85                  90                  95

Leu Glu Phe Pro Phe Thr Phe Gly Gln Gly Thr Lys Val Glu Ile Lys
            100                 105                 110

<210> SEQ ID NO 28
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="Asn"
<220> FEATURE:
<221> NAME/KEY: SITE
<222> LOCATION: (1)..(10)
<223> OTHER INFORMATION: /note="Variant residues given in the sequence
      have no preference with respect to those in the annotations
      for variant positions"

<400> SEQUENCE: 28

Gly Phe Thr Phe Thr Asp Phe Tyr Met Ser
1               5                   10

<210> SEQ ID NO 29
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: VARIANT
<222> LOCATION: (6)..(6)
<223> OTHER INFORMATION: /replace="Pro"
<220> FEATURE:
<221> NAME/KEY: VARIANT
<222> LOCATION: (8)..(8)
<223> OTHER INFORMATION: /replace="Ala"
<220> FEATURE:
<221> NAME/KEY: VARIANT
<222> LOCATION: (11)..(11)
<223> OTHER INFORMATION: /replace="Thr"
<220> FEATURE:
<221> NAME/KEY: VARIANT
<222> LOCATION: (12)..(12)
<223> OTHER INFORMATION: /replace="Asp"

```
<220> FEATURE:
<221> NAME/KEY: SITE
<222> LOCATION: (1)..(19)
<223> OTHER INFORMATION: /note="Variant residues given in the sequence
      have no preference with respect to those in the annotations
      for variant positions"

<400> SEQUENCE: 29

Val Ile Arg Asn Lys Ala Asn Gly Tyr Thr Ala Gly Tyr Asn Pro Ser
1               5                   10                  15

Val Lys Gly

<210> SEQ ID NO 30
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Thr"
<220> FEATURE:
<221> NAME/KEY: VARIANT
<222> LOCATION: (4)..(4)
<223> OTHER INFORMATION: /replace="Ser"
<220> FEATURE:
<221> NAME/KEY: SITE
<222> LOCATION: (1)..(9)
<223> OTHER INFORMATION: /note="Variant residues given in the sequence
      have no preference with respect to those in the annotations
      for variant positions"

<400> SEQUENCE: 30

Ala Arg Leu Thr Tyr Gly Phe Asp Tyr
1               5

<210> SEQ ID NO 31
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (10)..(10)
<223> OTHER INFORMATION: /replace="Thr"
<220> FEATURE:
<221> NAME/KEY: SITE
<222> LOCATION: (1)..(16)
<223> OTHER INFORMATION: /note="Variant residues given in the sequence
      have no preference with respect to those in the annotations
      for variant positions"

<400> SEQUENCE: 31

Gln Ser Ser Lys Ser Leu Leu His Ser Asn Gly Lys Thr Tyr Leu Asn
1               5                   10                  15

<210> SEQ ID NO 32
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: VARIANT
<222> LOCATION: (6)..(6)
<223> OTHER INFORMATION: /replace="Phe"
<220> FEATURE:
<221> NAME/KEY: SITE
<222> LOCATION: (1)..(9)
<223> OTHER INFORMATION: /note="Variant residues given in the sequence
      have no preference with respect to those in the annotations
      for variant positions"

<400> SEQUENCE: 32

Gln Gln Phe Leu Glu Tyr Pro Phe Thr
1               5

<210> SEQ ID NO 33

<400> SEQUENCE: 33

000

<210> SEQ ID NO 34
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Gly Gly Gly Ser
1               5

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 35

His His His His His His
1               5

<210> SEQ ID NO 36
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro

<210> SEQ ID NO 37
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 38
<211> LENGTH: 217
<212> TYPE: PRT
<213> ORGANISM: Homo sapiens

<400> SEQUENCE: 38

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
        180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 39
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Val Ser Lys Leu Thr Val Asp Lys Ser Arg Trp Gln Gln Gly Asn Val
        180                 185                 190

Phe Ser Cys Ser Val Leu His Glu Ala Leu His Ser His Tyr Thr Gln
        195                 200                 205

Lys Ser Leu Ser Leu Ser Pro Gly Lys
    210                 215

<210> SEQ ID NO 40
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 41
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 41

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125
```

```
Thr Lys Asn Gln Val Ser Leu Trp Cys Leu Val Lys Gly Phe Tyr Pro
        130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
                180                 185                 190

Phe Ser Cys Ser Val Leu His Glu Ala Leu His Ser His Tyr Thr Gln
                195                 200                 205

Lys Ser Leu Ser Leu Ser Pro Gly Lys
        210                 215

<210> SEQ ID NO 42
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
                20                  25                  30

Tyr Met Ser Trp Val Arg Gln Ala Pro Gly Lys Gly Leu Glu Trp Val
            35                  40                  45

Ser Val Ile Arg Asn Lys Ala Asn Ala Tyr Thr Ala Gly Tyr Asn Pro
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Trp Cys
        355                 360                 365

Leu Val Lys Gly Phe Tyr Pro Ser Asp Ile Ala Val Trp Trp Glu Ser
    370                 375                 380

Tyr Gly Thr Glu Trp Ser Ser Tyr Lys Thr Thr Pro Pro Val Leu Asp
385                 390                 395                 400

Ser Asp Gly Ser Phe Phe Leu Tyr Ser Lys Leu Thr Val Thr Lys Glu
                405                 410                 415

Glu Trp Gln Gln Gly Phe Val Phe Ser Cys Ser Val Leu His Glu Ala
            420                 425                 430

Leu His Ser His Tyr Thr Gln Lys Ser Leu Ser Leu Ser Pro Gly Lys
        435                 440                 445

<210> SEQ ID NO 43
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Phe Gly Thr Glu Trp Ser Asn
145                 150                 155                 160
```

Tyr Lys Thr Thr Pro Pro Val Leu Asp Ser Asp Gly Ser Phe Phe Leu
            165                 170                 175

Tyr Ser Lys Leu Thr Val Ser Lys Glu Glu Trp Gln Gln Gly Phe Val
        180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 44
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Phe Gly Thr Glu Trp Ser Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Ser Lys Glu Glu Trp Gln Gln Gly Phe Val
        180                 185                 190

Phe Ser Cys Ser Val Leu His Glu Ala Leu His Ser His Tyr Thr Gln
        195                 200                 205

Lys Ser Leu Ser Leu Ser Pro Gly Lys
    210                 215

<210> SEQ ID NO 45
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

```
<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Ser Val Ile Arg Asn Lys Ala Asn Ala Tyr Thr Ala Gly Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Phe Gly Thr Glu Trp Ser Asn Tyr Lys Thr Thr Pro Pro Val Leu Asp
385                 390                 395                 400

Ser Asp Gly Ser Phe Phe Leu Tyr Ser Lys Leu Thr Val Ser Lys Glu
                405                 410                 415
```

```
Glu Trp Gln Gln Gly Phe Val Phe Ser Cys Ser Val Leu His Glu Ala
                420                 425                 430

Leu His Ser His Tyr Thr Gln Lys Ser Leu Ser Leu Ser Pro Gly Lys
            435                 440                 445

<210> SEQ ID NO 46
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 47
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

Val Val Asp Val Ser His Glu Asp Pro Glu Val Lys Phe Asn Trp Tyr
                35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Leu His Glu Ala Leu His Ser His Tyr Thr Gln
        195                 200                 205

Lys Ser Leu Ser Leu Ser Pro Gly Lys
    210                 215

<210> SEQ ID NO 48
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Ser Val Ile Arg Asn Lys Ala Asn Ala Tyr Thr Ala Gly Tyr Asn Pro
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Tyr Gly Thr Glu Trp Val Asn Tyr Lys Thr Thr Pro Pro Val Leu Asp
385                 390                 395                 400

Ser Asp Gly Ser Phe Phe Leu Tyr Ser Lys Leu Thr Val Thr Lys Glu
                405                 410                 415

Glu Trp Gln Gln Gly Phe Val Phe Ser Cys Ser Val Leu His Glu Ala
            420                 425                 430

Leu His Ser His Tyr Thr Gln Lys Ser Leu Ser Leu Ser Pro Gly Lys
        435                 440                 445

<210> SEQ ID NO 49
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Glu Trp Gln Gln Gly Phe Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 50
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
        130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Glu Trp Gln Gln Gly Phe Val
            180                 185                 190

Phe Ser Cys Ser Val Leu His Glu Ala Leu His Ser His Tyr Thr Gln
            195                 200                 205

Lys Ser Leu Ser Leu Ser Pro Gly Lys
    210                 215

<210> SEQ ID NO 51
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Ser Val Ile Arg Asn Lys Ala Asn Ala Tyr Thr Ala Gly Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

```
Lys Cys Lys Val Ser Asn Lys Ala Leu Pro Ala Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Trp Cys
            355                 360                 365

Leu Val Lys Gly Phe Tyr Pro Ser Asp Ile Ala Val Glu Trp Glu Ser
370                 375                 380

Tyr Gly Thr Glu Trp Ser Asn Tyr Lys Thr Thr Pro Pro Val Leu Asp
385                 390                 395                 400

Ser Asp Gly Ser Phe Phe Leu Tyr Ser Lys Leu Thr Val Ser Lys Glu
            405                 410                 415

Glu Trp Gln Gln Gly Phe Val Phe Ser Cys Ser Val Leu His Glu Ala
            420                 425                 430

Leu His Ser His Tyr Thr Gln Lys Ser Leu Ser Leu Ser Pro Gly Lys
            435                 440                 445

<210> SEQ ID NO 52
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Ser Val Ile Arg Asn Lys Ala Asn Ala Tyr Thr Ala Gly Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220
```

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Leu His Glu Ala
            420                 425                 430

Leu His Ser His Tyr Thr Gln Lys Ser Leu Ser Leu Ser Pro Gly Lys
        435                 440                 445

<210> SEQ ID NO 53
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Ser Val Ile Arg Asn Lys Ala Asn Ala Tyr Thr Ala Gly Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Arg Leu Thr Tyr Gly Phe Asp Tyr Trp Gly Gln Gly Thr
        100                 105                 110

Leu Val Thr Val Ser Ser Ala Ser Thr Lys Gly Pro Ser Val Phe Pro
    115                 120                 125
```

```
Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Leu His Glu Ala
            420                 425                 430

Leu His Ser His Tyr Thr Gln Lys Ser Leu Ser Leu Ser Pro Gly Lys
            435                 440                 445
```

<210> SEQ ID NO 54
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

```
Asp Ile Val Met Thr Gln Thr Pro Leu Ser Leu Pro Val Thr Pro Gly
1               5                   10                  15

Glu Pro Ala Ser Ile Ser Cys Gln Ser Ser Lys Ser Leu Leu His Ser
            20                  25                  30
```

```
Thr Gly Lys Thr Tyr Leu Asn Trp Tyr Leu Gln Lys Pro Gly Gln Ser
         35                  40                  45
Pro Gln Leu Leu Ile Tyr Trp Met Ser Thr Arg Ala Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Gln Gln Phe
                 85                  90                  95
Leu Glu Tyr Pro Phe Thr Phe Gly Gln Gly Thr Lys Val Glu Ile Lys
             100                 105                 110
Arg Thr Val Ala Ala Pro Ser Val Phe Ile Phe Pro Pro Ser Asp Glu
         115                 120                 125
Gln Leu Lys Ser Gly Thr Ala Ser Val Val Cys Leu Leu Asn Asn Phe
     130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                 165                 170                 175
Thr Tyr Ser Leu Ser Ser Thr Leu Thr Leu Ser Lys Ala Asp Tyr Glu
             180                 185                 190
Lys His Lys Val Tyr Ala Cys Glu Val Thr His Gln Gly Leu Ser Ser
         195                 200                 205
Pro Val Thr Lys Ser Phe Asn Arg Gly Glu Cys
     210                 215

<210> SEQ ID NO 55
<211> LENGTH: 181
<212> TYPE: PRT
<213> ORGANISM: Homo sapiens

<400> SEQUENCE: 55

Asn Ser Val Ile Ile Val Asp Lys Asn Gly Arg Leu Val Tyr Leu Val
 1               5                  10                  15
Glu Asn Pro Gly Gly Tyr Val Ala Tyr Ser Lys Ala Ala Thr Val Thr
             20                  25                  30
Gly Lys Leu Val His Ala Asn Phe Gly Thr Lys Lys Asp Phe Glu Asp
         35                  40                  45
Leu Tyr Thr Pro Val Asn Gly Ser Ile Val Ile Val Arg Ala Gly Lys
     50                  55                  60
Ile Thr Phe Ala Glu Lys Val Ala Asn Ala Glu Ser Leu Asn Ala Ile
 65                  70                  75                  80
Gly Val Leu Ile Tyr Met Asp Gln Thr Lys Phe Pro Ile Val Asn Ala
                 85                  90                  95
Glu Leu Ser Phe Phe Gly His Ala His Leu Gly Thr Gly Asp Pro Tyr
             100                 105                 110
Thr Pro Gly Phe Pro Ser Phe Asn His Thr Gln Phe Pro Pro Ser Arg
         115                 120                 125
Ser Ser Gly Leu Pro Asn Ile Pro Val Gln Thr Ile Ser Arg Ala Ala
     130                 135                 140
Ala Glu Lys Leu Phe Gly Asn Met Glu Gly Asp Cys Pro Ser Asp Trp
145                 150                 155                 160
Lys Thr Asp Ser Thr Cys Arg Met Val Thr Ser Glu Ser Lys Asn Val
                 165                 170                 175
Lys Leu Thr Val Ser
             180
```

```
<210> SEQ ID NO 56
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gly Gly Gly Gly Ser Gly Gly Gly Gly Ser
1               5                   10

<210> SEQ ID NO 57
<211> LENGTH: 10
<212> TYPE: PRT
<213> ORGANISM: Homo sapiens

<400> SEQUENCE: 57

Asp Lys Thr His Thr Cys Pro Pro Cys Pro
1               5                   10

<210> SEQ ID NO 58
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid

<400> SEQUENCE: 58

Tyr Xaa Thr Glu Trp Ser Ser
1               5

<210> SEQ ID NO 59
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid

<400> SEQUENCE: 59

Thr Xaa Xaa Glu Xaa Xaa Xaa Xaa Phe
1               5

<210> SEQ ID NO 60
<211> LENGTH: 760
<212> TYPE: PRT
<213> ORGANISM: Macaca fascicularis
```

<400> SEQUENCE: 60

```
Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Gly Val Asp Glu Glu Asn Thr
        35                  40                  45

Asp Asn Asn Thr Lys Ala Asn Gly Thr Lys Pro Lys Arg Cys Gly Gly
50                  55                  60

Asn Ile Cys Tyr Gly Thr Ile Ala Val Ile Ile Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Ala Arg Glu Glu Pro
            100                 105                 110

Glu Glu Asp Phe Pro Ala Ala Pro Arg Leu Tyr Trp Asp Asp Leu Lys
            115                 120                 125

Arg Lys Leu Ser Glu Lys Leu Asp Thr Thr Asp Phe Thr Ser Thr Ile
130                 135                 140

Lys Leu Leu Asn Glu Asn Leu Tyr Val Pro Arg Glu Ala Gly Ser Gln
145                 150                 155                 160

Lys Asp Glu Asn Leu Ala Leu Tyr Ile Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Gly
            195                 200                 205

Leu Val Tyr Leu Val Glu Asn Pro Gly Gly Tyr Val Ala Tyr Ser Lys
210                 215                 220

Ala Ala Thr Val Thr Gly Lys Leu Val His Ala Asn Phe Gly Thr Lys
225                 230                 235                 240

Lys Asp Phe Glu Asp Leu Asp Ser Pro Val Asn Gly Ser Ile Val Ile
            245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
            275                 280                 285

Pro Ile Val Lys Ala Asp Leu Ser Phe Phe Gly His Ala His Leu Gly
290                 295                 300

Thr Gly Asp Pro Tyr Thr Pro Gly Phe Pro Ser Phe Asn His Thr Gln
305                 310                 315                 320

Phe Pro Pro Ser Gln Ser Ser Gly Leu Pro Asn Ile Pro Val Gln Thr
            325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Lys Met Val Thr Ser
            355                 360                 365

Glu Asn Lys Ser Val Lys Leu Thr Val Ser Asn Val Leu Lys Glu Thr
370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415
```

```
Ala Lys Ser Ser Val Gly Thr Ala Leu Leu Lys Leu Ala Gln Met
            420                 425                 430

Phe Ser Asp Met Val Leu Lys Asp Gly Phe Gln Pro Ser Arg Ser Ile
            435                 440                 445

Ile Phe Ala Ser Trp Ser Ala Gly Asp Phe Gly Ser Val Gly Ala Thr
            450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asp
                500                 505                 510

Val Lys His Pro Val Thr Gly Arg Ser Leu Tyr Gln Asp Ser Asn Trp
            515                 520                 525

Ala Ser Lys Val Glu Lys Leu Thr Leu Asp Asn Ala Ala Phe Pro Phe
            530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Val Glu Arg Ile Pro Glu Leu Asn Lys Val Arg Ala Ala Ala Glu
            580                 585                 590

Val Ala Gly Gln Phe Val Ile Lys Leu Thr His Asp Thr Glu Leu Asn
            595                 600                 605

Leu Asp Tyr Glu Arg Tyr Asn Ser Gln Leu Leu Phe Leu Arg Asp
            610                 615                 620

Leu Asn Gln Tyr Arg Ala Asp Val Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Arg Asn Ala Glu Lys Arg Asp Lys Phe Val Met Lys
            660                 665                 670

Lys Leu Asn Asp Arg Val Met Arg Val Glu Tyr Tyr Phe Leu Ser Pro
            675                 680                 685

Tyr Val Ser Pro Lys Glu Ser Pro Phe Arg His Val Phe Trp Gly Ser
            690                 695                 700

Gly Ser His Thr Leu Ser Ala Leu Leu Glu Ser Leu Lys Leu Arg Arg
705                 710                 715                 720

Gln Asn Asn Ser Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
            755                 760

<210> SEQ ID NO 61
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 61

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Leu His Glu Ala Leu His Ser His Tyr Thr Gln
        195                 200                 205

Lys Ser Leu Ser Leu Ser Pro Gly Lys
    210                 215

<210> SEQ ID NO 62
<211> LENGTH: 760
<212> TYPE: PRT
<213> ORGANISM: Homo sapiens

<400> SEQUENCE: 62

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140
```

-continued

```
Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560
```

```
Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
                660                 665                 670

Lys Leu Asn Asp Arg Val Met Arg Val Glu Tyr His Phe Leu Ser Pro
            675                 680                 685

Tyr Val Ser Pro Lys Glu Ser Pro Phe Arg His Val Phe Trp Gly Ser
        690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
                740                 745                 750

Val Trp Asp Ile Asp Asn Glu Phe
            755                 760

<210> SEQ ID NO 63
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140
```

```
Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Leu His Glu Ala Leu His Ser His Tyr Thr Gln
        195                 200                 205

Lys Ser Leu Ser Leu Ser Pro Gly
    210                 215
```

<210> SEQ ID NO 64
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
130                 135                 140

Ser Asp Ile Ala Val Trp Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Leu His Glu Ala Leu His Ser His Tyr Thr Gln
        195                 200                 205

Lys Ser Leu Ser Leu Ser Pro Gly
    210                 215
```

<210> SEQ ID NO 65
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

-continued

```
<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Ser Val Ile Arg Asn Lys Ala Asn Ala Tyr Thr Ala Gly Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Trp Cys
        355                 360                 365

Leu Val Lys Gly Phe Tyr Pro Ser Asp Ile Ala Val Trp Trp Glu Ser
    370                 375                 380

Tyr Gly Thr Glu Trp Ser Ser Tyr Lys Thr Thr Pro Pro Val Leu Asp
385                 390                 395                 400

Ser Asp Gly Ser Phe Phe Leu Tyr Ser Lys Leu Thr Val Thr Lys Glu
                405                 410                 415
```

```
Glu Trp Gln Gln Gly Phe Val Phe Ser Cys Ser Val Leu His Glu Ala
                420                 425                 430

Leu His Ser His Tyr Thr Gln Lys Ser Leu Ser Leu Ser Pro Gly
            435                 440                 445

<210> SEQ ID NO 66
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Phe Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Glu Trp Gln Gln Gly Phe Val
            180                 185                 190

Phe Ser Cys Ser Val Leu His Glu Ala Leu His Ser His Tyr Thr Gln
        195                 200                 205

Lys Ser Leu Ser Leu Ser Pro Gly
    210                 215

<210> SEQ ID NO 67
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30
```

```
Tyr Met Ser Trp Val Arg Gln Ala Pro Gly Lys Gly Leu Glu Trp Val
         35                  40                  45
Ser Val Ile Arg Asn Lys Ala Asn Ala Tyr Thr Ala Gly Tyr Asn Pro
 50                  55                  60
Ser Val Lys Gly Arg Phe Thr Ile Ser Arg Asp Asn Ser Lys Asn Thr
 65                  70                  75                  80
Leu Tyr Leu Gln Met Asn Ser Leu Arg Ala Glu Asp Thr Ala Val Tyr
                 85                  90                  95
Tyr Cys Ala Arg Leu Thr Tyr Gly Phe Asp Tyr Trp Gly Gln Gly Thr
                100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Ala Ala Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Trp Cys
        355                 360                 365
Leu Val Lys Gly Phe Tyr Pro Ser Asp Ile Ala Val Glu Trp Glu Ser
    370                 375                 380
Phe Gly Thr Glu Trp Ser Asn Tyr Lys Thr Thr Pro Pro Val Leu Asp
385                 390                 395                 400
Ser Asp Gly Ser Phe Phe Leu Tyr Ser Lys Leu Thr Val Ser Lys Glu
                405                 410                 415
Glu Trp Gln Gln Gly Phe Val Phe Ser Cys Ser Val Leu His Glu Ala
                420                 425                 430
Leu His Ser His Tyr Thr Gln Lys Ser Leu Ser Leu Ser Pro Gly
        435                 440                 445
```

-continued

```
<210> SEQ ID NO 68
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Val Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Leu His Glu Ala Leu His Ser His Tyr Thr Gln
        195                 200                 205

Lys Ser Leu Ser Leu Ser Pro Gly
    210                 215

<210> SEQ ID NO 69
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Ser Val Ile Arg Asn Lys Ala Asn Ala Tyr Thr Ala Gly Tyr Asn Pro
    50                  55                  60

Ser Val Lys Gly Arg Phe Thr Ile Ser Arg Asp Asn Ser Lys Asn Thr
65                  70                  75                  80
```

```
Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Tyr Gly Thr Glu Trp Val Asn Tyr Lys Thr Thr Pro Pro Val Leu Asp
385                 390                 395                 400

Ser Asp Gly Ser Phe Phe Leu Tyr Ser Lys Leu Thr Val Thr Lys Glu
                405                 410                 415

Glu Trp Gln Gln Gly Phe Val Phe Ser Cys Ser Val Leu His Glu Ala
            420                 425                 430

Leu His Ser His Tyr Thr Gln Lys Ser Leu Ser Leu Ser Pro Gly
        435                 440                 445

<210> SEQ ID NO 70
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 70

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Tyr Gly Thr Glu Trp Ser Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Ser Lys Glu Glu Trp Gln Gln Gly Phe Val
            180                 185                 190

Phe Ser Cys Ser Val Leu His Glu Ala Leu His Ser His Tyr Thr Gln
        195                 200                 205

Lys Ser Leu Ser Leu Ser Pro Gly
    210                 215
```

<210> SEQ ID NO 71
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Ser Trp Val Arg Gln Ala Pro Gly Lys Gly Leu Glu Trp Val
        35                  40                  45

Ser Val Ile Arg Asn Lys Ala Asn Ala Tyr Thr Ala Gly Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Leu Thr Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Trp Cys
            355                 360                 365

Leu Val Lys Gly Phe Tyr Pro Ser Asp Ile Ala Val Glu Trp Glu Ser
    370                 375                 380

Tyr Gly Thr Glu Trp Ser Asn Tyr Lys Thr Thr Pro Pro Val Leu Asp
385                 390                 395                 400

Ser Asp Gly Ser Phe Phe Leu Tyr Ser Lys Leu Thr Val Ser Lys Glu
                405                 410                 415

Glu Trp Gln Gln Gly Phe Val Phe Ser Cys Ser Val Leu His Glu Ala
                420                 425                 430

Leu His Ser His Tyr Thr Gln Lys Ser Leu Ser Leu Ser Pro Gly
            435                 440                 445

<210> SEQ ID NO 72
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30
```

```
Tyr Met Ser Trp Val Arg Gln Ala Pro Gly Lys Gly Leu Glu Trp Val
         35                  40                  45

Ser Val Ile Arg Asn Lys Ala Asn Ala Tyr Thr Ala Gly Tyr Asn Pro
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Leu Thr Tyr Gly Phe Asp Tyr Trp Gly Gln Gly Thr
             100                 105                 110

Leu Val Thr Val Ser Ser Ala Ser Thr Lys Gly Pro Ser Val Phe Pro
         115                 120                 125

Leu Ala Pro Ser Ser Lys Ser Thr Ser Gly Gly Thr Ala Ala Leu Gly
 130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                 165                 170                 175

Ser Ser Gly Leu Tyr Ser Leu Ser Ser Val Val Thr Val Pro Ser Ser
             180                 185                 190

Ser Leu Gly Thr Gln Thr Tyr Ile Cys Asn Val Asn His Lys Pro Ser
         195                 200                 205

Asn Thr Lys Val Asp Lys Lys Val Glu Pro Lys Ser Cys Asp Lys Thr
 210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                 245                 250                 255

Thr Pro Glu Val Thr Cys Val Val Val Asp Val Ser His Glu Asp Pro
             260                 265                 270

Glu Val Lys Phe Asn Trp Tyr Val Asp Gly Val Glu Val His Asn Ala
         275                 280                 285

Lys Thr Lys Pro Arg Glu Glu Gln Tyr Asn Ser Thr Tyr Arg Val Val
 290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                 325                 330                 335

Ile Ser Lys Ala Lys Gly Gln Pro Arg Glu Pro Gln Val Tyr Thr Leu
             340                 345                 350

Pro Pro Ser Arg Asp Glu Leu Thr Lys Asn Gln Val Ser Leu Ser Cys
         355                 360                 365

Ala Val Lys Gly Phe Tyr Pro Ser Asp Ile Ala Val Glu Trp Glu Ser
 370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                 405                 410                 415

Arg Trp Gln Gln Gly Asn Val Phe Ser Cys Ser Val Leu His Glu Ala
             420                 425                 430

Leu His Ser His Tyr Thr Gln Lys Ser Leu Ser Leu Ser Pro Gly
         435                 440                 445
```

```
<210> SEQ ID NO 73
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Phe
             20                  25                  30

Tyr Met Ser Trp Val Arg Gln Ala Pro Gly Lys Gly Leu Glu Trp Val
         35                  40                  45

Ser Val Ile Arg Asn Lys Ala Asn Ala Tyr Thr Ala Gly Tyr Asn Pro
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Leu Thr Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Ser Cys
        355                 360                 365
```

```
Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Leu His Glu Ala
                420                 425                 430

Leu His Ser His Tyr Thr Gln Lys Ser Leu Ser Leu Ser Pro Gly
                435                 440                 445

<210> SEQ ID NO 74
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Gln
            20                  25                  30

Trp Met Asn Trp Val Arg Gln Ala Pro Gly Gln Arg Leu Glu Trp Ile
        35                  40                  45

Gly Arg Ile Tyr Pro Gly Gly Asp Thr Asn Tyr Ala Gly Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270
```

```
Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 75
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Asp Val Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30

Asn Arg Tyr Thr Tyr Leu His Trp Tyr Gln Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215
```

<210> SEQ ID NO 76
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Gln
            20                  25                  30

Trp Met Asn Trp Val Arg Gln Ala Pro Gly Gln Arg Leu Glu Trp Ile
        35                  40                  45

Gly Arg Ile Tyr Pro Gly Gly Asp Thr Asn Tyr Ala Gly Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Leu Leu Arg Asn Gln Pro Gly Glu Ser Tyr Ala Met Asp Tyr
        100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
        275                 280                 285
```

-continued

```
Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Gly Ala Leu His Asn His Tyr Thr Gln Lys Ser Leu Ser
        435                 440                 445

Leu Ser Pro Gly Lys
        450

<210> SEQ ID NO 77
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Met Ser Tyr Ser Gly Ser Thr Arg Tyr Asn Pro Ser Leu
    50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Trp Pro Leu Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Val Thr Val Pro Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Asp Glu Leu Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
    435                 440                 445

<210> SEQ ID NO 78
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Glu Ile Val Met Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Gln Pro Glu
65                  70                  75                  80
```

Asp Phe Ala Val Tyr Tyr Cys Gln Gln Trp Ser Ser Tyr Pro Pro Ile
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 79
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Glu Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

-continued

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Trp Cys Leu Val Lys Gly Phe Tyr Pro Ser Asp Ile Ala Val Trp Trp
370                 375                 380

Glu Ser Tyr Gly Thr Glu Trp Ser Ser Tyr Lys Thr Thr Pro Pro Val
385                 390                 395                 400

Leu Asp Ser Asp Gly Ser Phe Phe Leu Tyr Ser Lys Leu Thr Val Thr
                405                 410                 415

Lys Glu Glu Trp Gln Gln Gly Phe Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 80
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Glu Pro Ala Asp Thr Ala Thr Tyr Tyr
                85                  90                  95
```

```
Cys Ala Arg Ser Met Ile Thr Asn Trp Tyr Phe Asp Val Trp Gly Ala
                100                 105                 110
Gly Thr Thr Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Trp Cys Leu Val Lys Gly Phe Tyr Pro Ser Asp Ile Ala Val Glu Trp
370                 375                 380
Glu Ser Tyr Gly Thr Glu Trp Val Asn Tyr Lys Thr Thr Pro Pro Val
385                 390                 395                 400
Leu Asp Ser Asp Gly Ser Phe Phe Leu Tyr Ser Lys Leu Thr Val Thr
                405                 410                 415
Lys Glu Glu Trp Gln Gln Gly Phe Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 81
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 81

```
Gln Val Thr Leu Arg Glu Ser Gly Pro Ala Leu Val Lys Pro Thr Gln
1               5                   10                  15
Thr Leu Thr Leu Thr Cys Thr Phe Ser Gly Phe Ser Leu Ser Thr Ser
            20                  25                  30
Gly Met Ser Val Gly Trp Ile Arg Gln Pro Pro Gly Lys Ala Leu Glu
        35                  40                  45
Trp Leu Ala Asp Ile Trp Trp Asp Asp Lys Lys Asp Tyr Asn Pro Ser
    50                  55                  60
Leu Lys Ser Arg Leu Thr Ile Ser Lys Asp Thr Ser Lys Asn Gln Val
65                  70                  75                  80
Val Leu Lys Val Thr Asn Met Glu Pro Ala Asp Thr Ala Thr Tyr Tyr
                85                  90                  95
Cys Ala Arg Ser Met Ile Thr Asn Trp Tyr Phe Asp Val Trp Gly Ala
            100                 105                 110
Gly Thr Thr Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Ser Cys Ala Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Lys Leu Thr Val Asp
                405                 410                 415
```

-continued

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 82
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 83
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 83

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Phe
             20                  25                  30

Tyr Met Ser Trp Val Arg Gln Ala Pro Gly Lys Gly Leu Glu Trp Val
         35                  40                  45

Ser Val Ile Arg Asn Lys Ala Asn Ala Tyr Thr Ala Gly Tyr Asn Pro
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Leu Thr Tyr Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 84
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Leu His Glu Ala Leu His Ser His Tyr Thr Gln
        195                 200                 205

Lys Ser Leu Ser Leu Ser Pro Gly
    210                 215
```